US011898206B2

(12) United States Patent
Wong et al.

(10) Patent No.: US 11,898,206 B2
(45) Date of Patent: Feb. 13, 2024

(54) SYSTEMS AND METHODS FOR CLONOTYPE SCREENING

(71) Applicant: 10X Genomics, Inc., Pleasanton, CA (US)

(72) Inventors: Alexander Y. Wong, San Francisco, CA (US); Jeffrey Mellen, Martinez, CA (US); Kevin Wu, San Francisco, CA (US); Paul Ryvkin, San Jose, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 216 days.

(21) Appl. No.: 15/984,324

(22) Filed: May 19, 2018

(65) Prior Publication Data
US 2018/0371545 A1    Dec. 27, 2018

Related U.S. Application Data

(60) Provisional application No. 62/582,866, filed on Nov. 7, 2017, provisional application No. 62/508,947, filed on May 19, 2017.

(51) Int. Cl.
| C07K 14/725 | (2006.01) |
| G16B 45/00 | (2019.01) |
| G16B 40/30 | (2019.01) |
| G16B 30/00 | (2019.01) |
| C12Q 1/686 | (2018.01) |
| G16B 30/10 | (2019.01) |
| C12Q 1/6881 | (2018.01) |
| C07K 16/28 | (2006.01) |
| C12Q 1/6883 | (2018.01) |
| C12Q 1/6806 | (2018.01) |

(52) U.S. Cl.
CPC ........ *C12Q 1/6881* (2013.01); *C07K 14/7051* (2013.01); *C07K 16/2809* (2013.01); *G16B 30/00* (2019.02); *G16B 40/30* (2019.02); *G16B 45/00* (2019.02); *C07K 2317/565* (2013.01); *C12Q 1/686* (2013.01); *C12Q 1/6806* (2013.01); *C12Q 1/6883* (2013.01); *C12Q 2600/156* (2013.01); *C12Q 2600/158* (2013.01); *C12Q 2600/16* (2013.01); *G16B 30/10* (2019.02)

(58) Field of Classification Search
None
See application file for complete search history.

(56) References Cited

U.S. PATENT DOCUMENTS

| 5,149,625 | A | 9/1992 | Church et al. |
| 5,202,231 | A | 4/1993 | Drmanac et al. |
| 5,413,924 | A | 5/1995 | Kosak et al. |
| 5,436,130 | A | 7/1995 | Mathies et al. |
| 5,512,131 | A | 4/1996 | Kumar et al. |
| 5,587,128 | A | 12/1996 | Wilding et al. |
| 5,605,793 | A | 2/1997 | Stemmer |
| 5,618,711 | A | 4/1997 | Gelfand et al. |
| 5,695,940 | A | 12/1997 | Drmanac et al. |
| 5,736,330 | A | 4/1998 | Fulton |
| 5,834,197 | A | 11/1998 | Parton |
| 5,851,769 | A | 12/1998 | Gray et al. |
| 5,856,174 | A | 1/1999 | Lipshutz et al. |
| 5,958,703 | A | 9/1999 | Dower et al. |
| 5,994,056 | A | 11/1999 | Higuchi |
| 6,046,003 | A | 4/2000 | Mandecki |
| 6,051,377 | A | 4/2000 | Mandecki |
| 6,057,107 | A | 5/2000 | Fulton |
| 6,103,537 | A | 8/2000 | Ullman et al. |
| 6,143,496 | A | 11/2000 | Brown et al. |
| 6,172,218 | B1 | 1/2001 | Brenner |
| 6,297,006 | B1 | 10/2001 | Drmanac et al. |
| 6,297,017 | B1 | 10/2001 | Thompson |
| 6,327,410 | B1 | 12/2001 | Walt et al. |
| 6,355,198 | B1 | 3/2002 | Kim et al. |
| 6,361,950 | B1 | 3/2002 | Mandecki |
| 6,372,813 | B1 | 4/2002 | Johnson et al. |

(Continued)

FOREIGN PATENT DOCUMENTS

| EP | 0249007 A2 | 12/1987 |
| EP | 0637996 B1 | 7/1997 |

(Continued)

OTHER PUBLICATIONS

Usoskin et al. Nature Neuroscience Nov. 2014, vol. 18, No. 1, pp. 145-153.*
Ross et al z Genome Biology (2016) 17:69 DOI 10.1186/s13059-016-0929-9.*
Schmidt et al Pharmaceuticals 2016, 9, 33; doi:10.3390/ph9020033.*

(Continued)

*Primary Examiner* — Joseph Woitach

(57) ABSTRACT

Methods for screening clonotypes are provided. Data representing a plurality of cells from a single subject is obtained. The data represents a plurality of clonotypes. The data includes a plurality of contigs for each respective clonotype in the plurality of clonotypes. Each respective contig in the plurality of contigs comprises (i) an indication of chain type for the respective contig and (ii) a contig sequence of an mRNA of the respective cell. There is determined, using the data, for each respective clonotype in the plurality of clonotypes, a number of the plurality of cells that represent the respective clonotype. In some instances, more than one cell in the plurality of cells have the same clonotype in the plurality of clonotypes. In some instances, the plurality of clonotypes comprises 25 clonotypes and where the plurality of cells includes at least one cell for each clonotype in the plurality of clonotypes.

14 Claims, 51 Drawing Sheets

(56) References Cited

U.S. PATENT DOCUMENTS

| | | |
|---|---|---|
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,871,444 B2 | 10/2014 | Griffiths et al. |
| 8,889,083 B2 | 11/2014 | Ismagilov et al. |
| 9,012,370 B2 | 4/2015 | Hong |
| 9,017,948 B2 | 4/2015 | Agresti et al. |
| 9,029,083 B2 | 5/2015 | Griffiths et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,694,361 B2 | 7/2017 | Bharadwaj et al. |
| 9,695,468 B2 | 7/2017 | Hindson et al. |
| 9,824,068 B2 | 11/2017 | Wong |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kum |
| 2009/0264299 A1 | 10/2009 | Drmanac et al. |

(56) References Cited

U.S. PATENT DOCUMENTS

| | | |
|---|---|---|
| 2009/0286687 A1 | 11/2009 | Dressman et al. |
| 2010/0021973 A1 | 1/2010 | Makarov et al. |
| 2010/0021984 A1 | 1/2010 | F. et al. |
| 2010/0022414 A1 | 1/2010 | Link et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0210479 A1 | 8/2010 | Griffiths et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |
| 2013/0274117 A1 | 10/2013 | Church et al. |
| 2013/0311106 A1 | 11/2013 | White et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Rooyen et al. |
| 2014/0206554 A1 | 7/2014 | Hindson et al. |
| 2014/0214334 A1 | 7/2014 | Plattner et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0220532 A1 | 8/2015 | Wong |
| 2015/0224466 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0232291 A1 | 8/2016 | Kyriazopoulou-Panagiotopoulou et al. |
| 2016/0289760 A1 | 10/2016 | Suzuki et al. |
| 2016/0304860 A1 | 10/2016 | Hindson et al. |
| 2016/0350478 A1 | 12/2016 | Chin et al. |
| 2017/0235876 A1 | 8/2017 | Jaffe et al. |
| 2018/0196781 A1 | 7/2018 | Wong |
| 2018/0225416 A1 | 8/2018 | Wong et al. |
| 2018/0265928 A1 | 9/2018 | Schnall-Levin et al. |

FOREIGN PATENT DOCUMENTS

| | | |
|---|---|---|
| EP | 1019496 B1 | 9/2004 |
| EP | 1482036 B1 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| GB | 2485850 A | 5/2012 |
| JP | 5949832 A | 3/1984 |
| JP | 2006507921 A | 3/2006 |
| JP | 2006289250 A | 10/2006 |
| JP | 2007268350 A | 10/2007 |
| JP | 2009208074 | 9/2009 |
| RU | 2321638 C2 | 4/2008 |
| WO | 1996029629 A2 | 9/1996 |
| WO | 1996041011 A1 | 12/1996 |
| WO | 1999009217 A1 | 2/1999 |
| WO | 1999052708 A1 | 10/1999 |
| WO | 2000008212 A1 | 2/2000 |
| WO | 2000026412 A1 | 5/2000 |
| WO | 2001014589 A2 | 3/2001 |
| WO | 2001089787 A2 | 11/2001 |
| WO | 2002031203 A2 | 4/2002 |
| WO | 2002086148 A1 | 10/2002 |
| WO | 2004002627 A2 | 1/2004 |
| WO | 2004010106 A2 | 1/2004 |
| WO | 2004069849 A2 | 8/2004 |
| WO | 2004091763 A2 | 10/2004 |
| WO | 2004102204 A1 | 11/2004 |
| WO | 2004103565 A2 | 12/2004 |
| WO | 2004105734 A1 | 12/2004 |
| WO | 2005002730 A1 | 1/2005 |
| WO | 2005021151 A1 | 3/2005 |
| WO | 2005023331 A2 | 3/2005 |
| WO | 2005040406 A1 | 5/2005 |
| WO | 2005049787 A9 | 6/2005 |
| WO | 2005082098 A2 | 9/2005 |
| WO | 2006030993 A1 | 3/2006 |
| WO | 2006078841 A1 | 7/2006 |

(56) References Cited

FOREIGN PATENT DOCUMENTS

| WO | 2006096571 A2 | 9/2006 |
|---|---|---|
| WO | 2007001448 A2 | 1/2007 |
| WO | 2007002490 A2 | 1/2007 |
| WO | 2007024840 A2 | 3/2007 |
| WO | 2007081385 A2 | 7/2007 |
| WO | 2007081387 A1 | 7/2007 |
| WO | 2007089541 A2 | 8/2007 |
| WO | 2007114794 A1 | 10/2007 |
| WO | 2007121489 A2 | 10/2007 |
| WO | 2007133710 A2 | 11/2007 |
| WO | 2007138178 A2 | 12/2007 |
| WO | 2007140015 A2 | 12/2007 |
| WO | 2007149432 A2 | 12/2007 |
| WO | 2008021123 A1 | 2/2008 |
| WO | 2008091792 A2 | 7/2008 |
| WO | 2008102057 A1 | 8/2008 |
| WO | 2008109176 A2 | 9/2008 |
| WO | 2008121342 A2 | 10/2008 |
| WO | 2008134153 A1 | 11/2008 |
| WO | 2007139766 A3 | 12/2008 |
| WO | 2009005680 A1 | 1/2009 |
| WO | 2009011808 A1 | 1/2009 |
| WO | 2009023821 A1 | 2/2009 |
| WO | 2009061372 A1 | 5/2009 |
| WO | 2009085215 A1 | 7/2009 |
| WO | 2010004018 A2 | 1/2010 |
| WO | 2010033200 A2 | 3/2010 |
| WO | 2010115154 A1 | 10/2010 |
| WO | 2010127304 A2 | 11/2010 |
| WO | 2010148039 A2 | 12/2010 |
| WO | 2010151776 A2 | 12/2010 |
| WO | 2011047870 A1 | 4/2011 |
| WO | 2011056546 A1 | 5/2011 |
| WO | 2011066476 A1 | 6/2011 |
| WO | 2011074960 A1 | 6/2011 |
| WO | 2012012037 A1 | 1/2012 |
| WO | 2012048341 A1 | 4/2012 |
| WO | 2012055929 A1 | 5/2012 |
| WO | 2012061832 A1 | 5/2012 |
| WO | 2012100216 A2 | 7/2012 |
| WO | 2012083225 A3 | 8/2012 |
| WO | 2012106546 A2 | 8/2012 |
| WO | 2012112804 A1 | 8/2012 |
| WO | 2012116331 A2 | 8/2012 |
| WO | 2012142531 A2 | 10/2012 |
| WO | 2012142611 A2 | 10/2012 |
| WO | 2012149042 A2 | 11/2012 |
| WO | 2012166425 A2 | 12/2012 |
| WO | 2013035114 A1 | 3/2013 |
| WO | 2013055955 A1 | 4/2013 |
| WO | 2013123125 A1 | 8/2013 |
| WO | 2013177220 A1 | 11/2013 |
| WO | 2014028537 A1 | 2/2014 |
| WO | 2014093676 A1 | 6/2014 |
| WO | 2015002908 A1 | 1/2015 |
| WO | 2015157567 A1 | 10/2015 |
| WO | 2015200891 A1 | 12/2015 |
| WO | 2016130578 A1 | 8/2016 |

OTHER PUBLICATIONS

"bedtools: General Usage," http://bedtools.readthedocs.io/en/latest/content/generalusage.html; Retrieved from the Internet Jul. 8, 2016.

"SSH Tunnel—Local and Remote Port Forwarding Explained With Examples," Trackets Blog, http://blog.trackets.com/2014/05/17/ssh-tunnel-local-and-remote-port-forwarding-explained with-examples.html; Retrieved from the Internet Jul. 7, 2016.

Abate et al., Valve-based flow focusing for drop formation. Appl Phys Lett. 2009;94. 3 pages.

Abate, A.R et al. "Beating Poisson encapsulation statistics using close-packed ordering" Lab on a Chip (Sep. 21, 2009) 9(18):2628-2631.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Agresti, et al. Selection of ribozymes that catalyse multiple-turnover Diels-Alder cycloadditions by using in vitro compartmentalization. Proc Natl Acad Sci U S A. Nov. 8, 2005;102(45): 16170-5. Epub Oct. 31, 2005.

Aitman, et al. Copy number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Biol., 329: 196-205 (2006).

Akselband, "Rapid mycobacteria drug susceptibility testing using gel microdrop (GMD) growth assay and flow cytometry", J. Microbiol. Methods, 62:181-197 (2005).

Anna et al., "Formation of dispersions using 'flow focusing' in microchannels", Appln. Phys. Letts. 82:3 364 (2003).

Attia, U.M et al., "Micro-injection moulding of polymer microfluidic devices" Microfluidics and nanofluidics (2009) 7(1):1-28.

Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.

Bansal et al. "An MCMC algorithm for haplotype assembly from whole-genome sequence data," (2008) Genome Res 18:1336-1346.

Bansal et al. "HapCUT: an efficient and accurate algorithm for the haplotype assembly problem," Bioinformatics (2008) 24:i153-i159.

Baret et al. "Fluorescence-activated droplet sorting (FADS): efficient microfluidic cell sorting based on enzymatic activity" Lab on a Chip (2009) 9(13):1850-1858.

Bentley et al. "Accurate whole human genome sequencing using reversible terminator chemistry," (2008) Nature 456:53-59.

Boone, et al. Plastic advances microfluidic devices. The devices debuted in silicon and glass, but plastic fabrication may make them hugely successful in biotechnology application. Analytical Chemistry. Feb. 2002; 78A-86A.

Braeckmans et al., Scanning the Code. Modern Drug Discovery. 2003:28-32.

Bransky, et al. A microfluidic droplet generator based on a piezoelectric actuator. Lab Chip. Feb. 21, 2009;9(4):516-20. doi: 10.1039/b814810d. Epub Nov. 20, 2008.

Bray, "The JavaScript Object Notation (JSON) Data Interchange Format," Mar. 2014, retrieved from the Internet Feb. 15, 2015; https://tools.ietf.org/html/rfc7159.

Brouzes, E et al., "Droplet microfluidic technology for single-cell high-throughput screening" PNAS (2009) 106(34):14195-14200.

Browning, S.R. et al. "Haplotype Phasing: Existing Methods and New Developments" NaRevGenet (Sep. 16, 2011) 12(10):703-714.

Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.

Carroll, "The selection of high-producing cell lines using flow cytometry and cell sorting", Exp. Op. Bioi. Therp., 4:11 1821-1829 (2004).

Chaudhary "A rapid method of cloning functional variable-region antibody genes in *Escherichia coli* as single-chain immunotoxins" Proc. Nat!. Acad. Sci USA 87: 1066-1070 (Feb. 1990).

Chechetkin et al., Sequencing by hybridization with the generic 6-mer oligonucleotide microarray: an advanced scheme for data processing. J Biomol Struct Dyn. Aug. 2000;I8(1):83-101.

Chen et al. "BreakDancer: an algorithm for high-resolution mapping of genomic structural variation," Nature Methods (2009) 6(9):677-681.

Chen, F. et al. "Chemical transfection of cells in picoliter aqueous droplets in fluorocarbon oil" Anal Chem (2011) 83(22):8816-8820.

Choi et al. "Identification of novel isoforms of the EML4-ALK transforming gene in non-small cell lung cancer," Cancer Res (2008) 68:4971-4976.

Chokkalingam, V et al., "Probing cellular heterogeneity in cytokine-secreting immune cells using droplet-based microfluidics" Lab Chip (2013) 13:4740-4744.

(56) References Cited

OTHER PUBLICATIONS

Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.
Chu, L-Y. et al., "Controllable monodisperse multiple emulsions" Angew. Chem. Int. Ed. (2007) 46:8970-8974.
Clausell-Tormos et al., "Droplet-based microfluidic platforms for the encapsulation and screening of mammalian cells and multicellular organisms", Chem. Biol. 15:427-437 (2008).
Cleary et al. "Joint variant and de novo mutation identification on pedigrees from highthroughput sequencing data," J Comput Biol (2014) 21:405-419.
Cook, et al. Copy-number variations associated with neuropsychiatric conditions. Nature. Oct. 16, 2008;455(7215):919-23. doi: 10.1038/nature07458.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
De Bruin et al., UBS Investment Research. Q-Series?: DNa Sequencing. UBS Securities LLC. Jul. 12, 2007. 15 pages.
Demirci, et al. "Single cell epitaxy by acoustic picolitre droplets" Lab Chip. Sep. 2007; 7(9):1139-45. Epub Jul. 10, 2007.
Doerr, "The smallest bioreactor", Nature Methods, 2:5 326 (2005).
Dowding, et al. "Oil core/polymer shell microcapsules by internal phase separation from emulsion droplets. II: controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, D.J. et al., "Ultrahigh-throughput mammalian single-cell reverse-transcriptase polymerase chain reaction In microfluidic droplets" Anal. Chem. (2013) 85:8016-8021.
Eid et al. "Real-time sequencing form single polymerase molecules," Science (2009) 323:133-138.
Ekblom, R. et al. "A field guide to whole-genome sequencing, assembly and annotation" Evolutionary Apps (Jun. 24, 2014) 7(9):1026-1042.
Esser-Kahn, et al. Triggered release from polymer capsules. Macromolecules. 2011; 44:5539-5553.
Makino, K. et al. "Preparation of hydrogel microcapsules Effects of preparation conditions upon membrane properties" Colloids and Surfaces: B Biointerfaces (1998) 12:97-104.
Marcus. Gene method offers diagnostic hope. The Wall Street Journal. Jul. 11, 2012.
Margulies et al. "Genome sequencing in microfabricated high-density picoliter reactors," Nature (2005) 437:376-380.
Matochko, W.L. et al., "Uniform amplification of phage display libraries in monodisperse emulsions," Methods (2012) 58:18-27.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McCoy, R. et al. "Illumina TruSeq Synthetic Long-Reads Empower De Novo Assembly and Resolve Complex, Highly-Repetitive Transposable Elements" PLOS (2014) 9(9):e1016689.
McKenna et al. "The Genome Analysis Toolkit: A MapReduce framework for anaylzing nextgeneration DNA sequencing data," Genome Research (2010) pp. 1297-1303.
Merriman, et al. Progress in ion torrent semiconductor chip based sequencing. Electrophoresis. Dec. 2012;33(23):3397-3417. doi: 10.1002/elps.201200424.
Microfluidic ChipShop. Microfluidic product catalogue. Mar. 2005.
Microfluidic ChipShop. Microfluidic product catalogue. Oct. 2009.

Miller et al. "Assembly Algorithms for next-generation sequencing data," Genomics, 95 (2010), pp. 315-327.
Mirzabekov, "DNA Sequencing by Hybridization—a Megasequencing Method and A Diagnostic Tool?" Trends in Biotechnology 12(1): 27-32 (1994).
Moore, J.L. et al., "Behavior of capillary valves in centrifugal microfluidic devices prepared by three-dimensional printing" Microfluid Nanofluid (2011) 10:877-888.
Mouritzen et al., Single nucleotide polymorphism genotyping using locked nucleic acid (LNa). Expert Rev Mol Diagn. Jan. 2003;3(1):27-38.
Myllykangas et al. "Efficient targeted resequencing of human germline and cancer genomes by oligonucleotide-selective sequencing," Nat Biotechnol, (2011) 29:1024-1027.
Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.
Navin, N.E. "The first five years of single-cell cancer genomics and beyond" Genome Res. (2015) 25:1499-1507.
Nguyen, et al. In situ hybridization to chromosomes stabilized in gel microdrops. Cytometry. 1995; 21:111-119.
Novak, R. et al., "Single cell multiplex gene detection and sequencing using microfluidicallygenerated agarose emulsions" Angew. Chem. Int. Ed. Engl. (2011) 50(2):390-395.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Pushkarev et al. "Single-molecule sequencing of an individual human genome," Nature Biotech (2009) 17:847-850.
Ritz, A. et al. "Characterization of structural variants with single molecule and hybrid sequencing approaches" Bioinformatics (2014) 30(24):3458-3466.
Ropers. New perspectives for the elucidation of genetic disorders. Am J Hum Genet. Aug. 2007;81(2):199-207. Epub Jun. 29, 2007.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: analysis of the NFI gene. Genet Test. 2006 Spring;10(1):8-17.
Schmitt, "Bead-based multiplex genotyping of human papillomaviruses", J. Clinical Microbiol., 44:2 504-512 (2006).
Sebat, et al. Strong association of de novo copy number mutations with autism. Science. Apr. 20, 2007;316(5823):445-9. Epub Mar. 15, 2007.
Seiffert, S. et al., "Smart microgel capsules from macromolecular precursors" J. Am. Chem. Soc. (2010) 132:6606-6609.

(56) References Cited

OTHER PUBLICATIONS

Shah, "Fabrication of mono disperse thermosensitive microgels and gel capsules in micro fluidic devices", Soft Matter, 4:2303-2309 (2008).

Shendure et al. "Accurate Multiplex Polony Sequencing of an Evolved bacterial Genome" Science (2005) 309:1728-1732.

Shimkus et al. "A chemically cleavable biotinylated nucleotide: Usefulness in the recovery of protein-DNA complexes from avidin affinity columns" PNAS (1985) 82:2593-2597.

Shlien, et al. Copy number variations and cancer. Genome Med. Jun. 16, 2009;1(6):62. doi: 10.1186/gm62.

Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.

Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.

Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.

Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).

Sun et al., Progress in research and application of liquid-phase chip technology. Chinese Journal Experimental Surgery. May 2005;22(5):639-40.

Tawfik, D.S. et al. "Man-made cell-like compartments for molecular evolution" Nature Biotech (Jul. 1998) 16:652-656.

Tewhey et al. "The importance of phase information for human genomics," Nat Rev Genet (2011) 12:215-223.

Tewhey, R. et al., "Microdroplet-based PCR enrichment for large-scale targeted sequencing" Nature Biotech. (2009) 27(11):1025-1031 and Online Methods (11 pages).

The SAM/BAM Format Specificatio Working Group, "Sequence Alignment/ Map Format Specification," Dec. 28, 2014.

Theberge, A.B, et al. Microdropelts in microfluidics: an evolving platform for discoveries in chemsitry and biology. Angew Chem Int Ed Engl. Aug. 9, 2010;49(34):5846-68. doi: 10.1002/anie.200906653.

Tonelli, C. et al., "Perfluoropolyether functional oligomers: unusual reactivity in organic chemistry" J. Fluorine Chem. (2002) 118:107-121.

Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.

Turner, et al. "Methods for genomic partitioning" Annu Rev Genomics Human Genet. (2009) 10:263-284. doi: 10.1146/annurev-genom-082908-150112. Review.

Voskoboynik, A. et al. "The genome sequence of the colonial chordate, Botryllus schlosseri." eLife Jul. 2, 2013, 2:e00569.

Wagner, O et al., "Biocompatible fluorinated polyglycerols for droplet microfluidics as an alternative to PEG-based copolymer surfactants" Lab Chip DOI:10.1039/C5LC00823A. (2015).

Wang et al., Single nucleotide polymorphism discrimination assisted by improved base stacking hybridization using bligonucleotide microarrays. Biotechniques. 2003;35:300-08.

Wang, et al. A novel thermo-induced self-bursting microcapsule with magnetic-targeting property. Chemphyschem. Oct. 5, 2009;10(14):2405-9.

Wang, et al. Digital karyotyping. Proc Natl Acad Sci U S A. Dec. 10, 2002;99(25):16156-61. Epub Dec. 2, 2002.

Weaver, J.C. et al. "Rapid clonal growth measurements at the single-cell level: gel microdroplets and flow cytometry", Biotechnology, 9:873-877 (1991).

Wheeler et al., "Database resources of the National Center for Biotechnology Information," Nucleic Acids Res. (2007) 35 (Database issue): D5-12.

Whitesides, "Soft lithography in biology and biochemistry", Annual Review of Biomedical Engineering, 3:335-373 (2001).

Williams, R. et al. "Amplification of complex gene libraries by emulsion PCR" Nature Methods (Jul. 2006) 3(7):545-550.

Woo, et al. G/C-modified oligodeoxynucleotides with selective complementarity: synthesis and hybridization properties. Nucleic Acids Res. Jul. 1, 1996;24(13):2470-5.

Kia, "Soft lithography", Annual Review of Material Science, 28: 153-184 (1998).

Yamamoto, et al. Chemical modification of Ce(IV)/EDTA-base artificial restriction DNa cutter for versatile manipulation of doulbe-stranded DNa. Nucleic Acids Research. 2007; 35(7):e53.

Zerbino et al. "Velvet: Algorithms for de novo short read assembly using de Bruijn graphs," Genome Research (2008) 18:821-829.

Zerbino, D.R. "Using the Velvet de novo assembler for short-read sequencing technologies" Curr Protoc Bioinformatics (Sep. 1, 2010) 31:11.5:11.5.1-11.5.12.

Zerbino, Daniel, "Velvet Manual—version 1.1," Aug. 15, 2008, pp. 1-22.

Zhang, "Combinatorial marking of cells and organelles with reconstituted fluorescent proteins", Cell, 119:137-144 (Oct. 1, 2004).

Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.

Zhao, J., et al., "Preparation of hemoglobin-loaded Nano-sized particles with porous structure as oxygen carriers," Biomaterials, vol. 28, pp. 1414-1422 (2007).

Zheng, X.Y. et al. "Haplotyping germline and cancer genomes with high-throughput linked-read sequencing" Nature Biotech (Feb. 1, 2016) 34(3):303-311 and Supplemental Material.

Zhu, S. et al., "Synthesis and self-assembly of highly incompatible polybutadienepoly(hexafluoropropoylene oxide) diblock copolymers" J. Polym. Sci. (2005) 43:3685-3694.

Zimmermann et at., Microscale production of hybridomas by hypo-osmolar electrofusion. Human Antibodies Hybridomas. Jan. 1992;3(1 ): 14-8.

Zong, C. et al. "Genome-wide detection of single-nucleotide and copy-number variations of a single human cell" Science. Dec. 21, 2012;338(6114):1622-6. doi: 10.1126/science.1229164.

Freeman et al., "Profiling the T-cell receptor beta-chain repertoire by massively parallel sequencing", Genome Research, Dec. 31, 2009, 9 pages.

Bischof et al., "bcRep: R Package for Comprehensive Analysis of B Cell Receptor Repertoire Data", PLOS One, Aug. 23, 2016, 15 pages.

Fisher, S. et al. "A Scalable, fully automated process for construction of sequence-ready human exome targeted capture libraries" Genome Biology (2011) 2:R1-R15. doi: 10.1186/GB-2011-12-1-r1. Epub Jan. 4, 2011.

Fredrickson, C.K. et al., "Macro-to-micro interfaces for microfluidic devices" Lab Chip (2004) 4:526-533.

Freiberg, et al. "Polymer microspheres for controlled drug release" Int J Pharm. Sep. 10, 2004;282(1-2):1-18.

Fu. A.Y. et al. "A microfabricated fluorescence-activated cell sorter" Nature Biotech (Nov. 1999) 17:1109-1111.

Fulton et al., "Advanced multiplexed analysis with the FlowMetrix system" Clin Chern. Sep. 1997;43(9): 1749-56.

Garstecki, P. et al. "Formation of monodisperse bubbles in a microfluidic flow-focusing device" Appl. Phys. Lett (2004) 85(13):2659-2651. DOI: 10.1063/1.1796526.

Gartner, et al. The Microfluidic Toolbox: examples for fluidic interfaces and standardization concepts. Proc. SPIE 4982, Microfluidics, BioMEMS, and Medical Microsystems, (Jan. 17, 2003); doi: 10.1117/12.479566.

Ghadessy, et al. Directed evolution of polymerase function by compartmentalized self-replication. Proc Natl Acad Sci U S A. Apr. 10, 2001;98(8):4552-7. Epub Mar. 27, 2001.

(56) References Cited

OTHER PUBLICATIONS

Gonzalez, et al. The influence of CCL3L1 gene-containing segmental duplications on HIV-1/AIDS susceptibility. Science. Mar. 4, 2005;307(5714):1434-40. Epub Jan. 6, 2005.
Gordon et al. "Consed: A Graphical Tool for Sequence Finishing," Genome Research (1998) 8:198-202.
Granieri, Lucia "Droplet-based microfluidics and engineering of tissue plasminogen activator for biomedical applications" Ph.D. Thesis, Nov. 13, 2009 (131 pages).
Grasland-Mongrain, E. et al. "Droplet coalescence in microlfuidic devices" Internet Citation, 2003, XP002436104, Retrieved from the Internet: URL:http://www.eleves.ens.fr./home/grasland/rapports/stage4.pdf [retrieved on Jun. 4, 2007].
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" Anal. Chem 77: 1539-1544 (2005).
Heng et al. "Fast and accurate long-read alignment with Burrows-Wheeler transform," Bioinformatics (2010) 25(14):1754-1760.
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Huang et al. "EagleView: A genome assembly viewer for next-generationsequencing technologies," Genome Research (2008) 18:1538-1543.
Huebner, "Quantitative detection of protein expression in single cells using droplet microfluidics", Chern. Commun. 1218-1220 (2007).
Hug, H. et al. "Measurement of the number of molecules of a single mRNA species in a complex mRNA preparation" J Theor Biol. Apr. 21, 2003;221(4):615-24.
Illumina, Inc. An Introduction to Next-Generation Sequencing Technology. Feb. 28, 2012.
Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Kanehisa et al. "KEGG: Kyoto Encyclopedia of Genes and Genomes," Nucleic Acids Research (2000) 28:27-30.
Khomiakov A et al., "Analysis of perfect and mismatched DNA duplexes by a generic hexanucleotide microchip". Mol Bioi (Mosk). Jul.-Aug. 2003;37(4):726-41. Russian. Abstract only.
Kim et al. "HapEdit: an accuracy assessment viewer for haplotype assembly using massively parallel DNA-sequencing technologies," Nucleic Acids Research (2011) pp. 1-5.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functional microgels in microfluidic devices. Angew Chem Int Ed Engl. 2007;46(11):1819-22.
Kim, J et al., "Rapid prototyping of microfluidic systems using a PDMS/polymer tape composite" Lab Chip (2009) 9:1290-1293.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Klein, et al. Droplet barcoding for single-cell transcriptomics applied to embryonic stem cells. Cell. May 21, 2015;161:1187-1201.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip The Royal Soc. of Chern. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Layer et al. "Lumpy: A probabilistic framework for structural variant discovery," Genome Biology (2014) 15(6):R84.
Li, Y., et al., "PEGylated PLGA Nanoparticles as protein carriers: synthesis, preparation and biodistribution in rats," Journal of Controlled Release, vol. 71, pp. 203-211 (2001).
Lippert et al. "Algorithmic strategies for the single nucleotide polymorphism haplotype assembly problem," Brief. Bionform (2002) 3:23-31.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6):703-707 (Jun. 2006).
Lowe, Adam J."Norbornenes and [n]polynorbornanes as molecular scaffolds for anion recognition" Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, D.A. et al., "Injection molded microfluidic chips featuring integrated interconnects" Lab Chip (2006) 6:1346-1354.
Bluthmann et al., 1988, "T-cell-specific deletion of T-cell receptor transgenes allows functional rearrangement of endogenous alpha- and beta-genes," Nature 334, pp. 156-159.
Ganusov et al., 2007, "Do most lymphocytes in humans really reside in the gut?," Trends Immunol, 208(12), pp. 514-518.
Mostovoy et al., 2016, "A hybrid approach for de novo human genome sequence assembly and phasing," Nat. Methods 13, 587-590.
Narasimhan et al., 2016, "Health and population effects of rare gene knockouts in adult humans with related parents," Science 352, pp. 474-477 (2016).
Rudolph et al., 2006, "How TCRs bind MHCs, peptides, and coreceptors," Annu Rev Immunol 24:pp. 419-466, doi:10.1146/annurev.immunol.23.021704.115658.
Uematsu et al., 1988, "In transgenic mice the introduced functional T-cell receptor beta gene prevents expression of endogenous beta genes," Cell 52, pp. 831-841.
Yassai et al., 2009, "A clonotype nomenclature for T-cell receptors," Immunogenetics 61, pp. 493-502.
Yaari and Kleinstein, 2015, "Practical guidelines for B-cell repertoire sequencing analysis," Genome Medicine 7:121.
Matsuda et al., 1998, "The complete nucleotide sequence of the human immunoglobulin heavy chain variable region locus," The Journal of Experimental Medicine. 188 (11): 2151-62, doi: 10.1084/jem.188.11.2151.
Li et al., 2004, "Utilization of Ig heavy chain variable, diversity, and joining gene segments in children with B-lineage acute lymphoblastic

(56) References Cited

OTHER PUBLICATIONS leukemia: implications for the mechanisms of VDJ recombination and for pathogenesis," Blood. 103 (12): 4602-9, doi:10.1182/blood-2003-11-3857.

Chen et al., 2010, "Clustering-based identification of clonally related immunoglobulin gene sequence sets," Immunome Res. 6 Suppl 1:S4.

Hershberg and Prak, 2015, "The analysis of clonal expansion in normal and autoimmune B-cell repertoires," Philos Trans R Soc Lond B Biol Sci. 370(1676).

Zheng, 2017, "Massively parallel digital transcriptional profiling of single cells," Nature Communications, DOI: 10.1038/ncomms 14049.

Aken et al., 2015, "The Ensembl gene annotation system Database," baw093, doi: 10.1093/database/baw093.

McLaren, 2016, et al., "The Ensembl Variant Effect Predictor," Genome Biology 17, p. 122, doi: 10.1186/s13059-016-0974-4.

Chromium, Single Cell 3' Reagent Kits v2. User Guide, 2017, 10X Genomics, Pleasanton, California, Rev. B.

Chromium Single Cell V(D)J Reagent Kits User Guide, 2017, 10X Genomics.

10x Genomics Announces the Addition of Unbiased Gene Expression and B-cell Repertoire to the Chromium Single Cell V(D)J Solution, Oct. 18, 2017, https://www.businesswire.com/news/home/20171018005362/en/10x-Genomics-Announces-Addition-Unbiased-Gene-Expression#.XLfZzQ4GaAw.email.

U.S. Appl. No. 62/572,544, filed Oct. 15, 2017.

Greiff et al., "Bioinformatic and Statistical Analysis of Adaptive Immune Repertoires," Trends in Immunology, Nov. 2015, vol. 36 No. 11, pp. 738-749.

Turchaninova et al., "High-quality full-length immunoglobulin profiling with unique molecular barcoding," Nature Protocols, Aug. 4, 2016, vol. 11 No. 9, pp. 1599-1616.

Zhang et al., "IMonitor: A Robust Pipeline for TCR and BCR Repertoire Analysis," Genetics, Aug. 21, 2015, vol. 201 No. 2, pp. 459-472.

Extended European Search Report dated Feb. 15, 2021, for European Patent Application No. 18802746.0.

\* cited by examiner

SYSTEMS AND METHODS FOR CLONOTYPE SCREENING

CROSS REFERENCE TO RELATED APPLICATIONS

This application claims priority to U.S. Provisional Application No. 62/508,947, filed May 19, 2017, entitled "SYSTEMS AND METHODS FOR ANALYZING DATASETS," and U.S. Provisional Application No. 62/582,866, filed Nov. 7, 2017, entitled "SYSTEMS AND METHODS FOR ANALYZING DATASETS," each of which is herein incorporated by reference.

TECHNICAL FIELD

This specification describes technologies to evaluate clonotypes.

BACKGROUND

The discovery of patterns in a dataset facilitates a number of technical applications such as the validation, in the biological arts, of RNA-extraction protocols and associated methodologies that result in mRNA sequencing of mRNA in single cells. Such techniques have given rise to high throughput transcript identification and sequencing of genes in hundreds or even thousands of individual cells in a single dataset. Thus, in the art, datasets containing attribute values (e.g., transcript reads mapped to individual genes in a particular cell) have been generated. While this is a significant advancement in the art, a number of technical problems need to be addressed to make such data more useful.

In particular, the adaptive human immune system is comprised of B-cells and T-cells. During T-cell and B-cell development these cells express unique heterodimeric receptors that are used for recognition of pathogens. Each of these receptor chains is generated by a somatic rearrangement process that joins different segments of the TCR and BCR genes and creates a novel gene. This joining process is imprecise with insertion of nontemplated nucleotides (N nucleotides) in the junction site, as well as 3'- and 5'-nucleotide deletion from the germline genes participating in the rearrangement. This region of random nucleotide insertion or deletion referred to as the third complementarity-determining region (CDR3). The resulting CDR3 have a unique nucleotide sequence that is specific to that particular B or T-cell and all its progeny. Hence, the clonotypic nature of the receptors. The CDR3 is the portion of these receptors that is most involved in interactions with intact soluble antigens (B-cells) or intracellular processed antigens presented as immunogenic peptides loaded in MHC molecules (T-cells). See Yassai et al., 2009, "A clonotype nomenclature for T-cell receptors," Immunogenetics 61, pp. 493-502. Given the ability to generate large amounts of data, what is needed in the art are improved systems and methods for analyzing such data.

SUMMARY

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

In the present disclosure, data representing a plurality of cells from a single subject is obtained. The data represents a plurality of clonotypes. The data includes a plurality of contigs for each respective clonotype in the plurality of clonotypes. Each respective contig in the plurality of contigs comprises (i) an indication of chain type for the respective contig, and a contig (consensus) sequence of an mRNA of the respective cell. There is determined, using the data, for each respective clonotype in the plurality of clonotypes, a number of the plurality of cells that represent the respective clonotype. In some embodiments, respective clonotypes in the plurality of clonotypes are ordered by the number of the plurality of cells that have the respective clonotype. In some embodiments, more than one cell in the plurality of cells have the same clonotype in the plurality of clonotypes. In some embodiments, more than ten cells in the plurality of cells have the same clonotype in the plurality of clonotypes. In some embodiments, the plurality of clonotypes comprises 25 clonotypes and wherein the plurality of cells includes at least one cell for each clonotype in the plurality of clonotypes. In some embodiments, the plurality of clonotypes comprises 100 clonotypes and the plurality of cells includes at least one cell for each clonotype in the plurality of clonotypes. In some embodiments, the plurality of cells consists of B-cells from the single subject. In some embodiments, the plurality of cells consists of B-cells from the single subject. In some embodiments, the single subject is mammalian. In some embodiments, the single subject is mammalian, a reptile, avian, amphibian, fish, ungulate, ruminant, bovine, equine, caprine, ovine, swine, camelid, monkey, ape, ursid, poultry, dog, cat, mouse, rat, fish, dolphin, whale or shark.

One aspect of the present disclosure provides a system comprising one or more processing cores, a memory, and a display, the memory storing instructions for performing a method for analyzing one or more datasets using the one or more processing cores. The method comprises obtaining a first dataset representing a first plurality of cells from a single first subject. The first dataset represents a first plurality of clonotypes. The first dataset includes a plurality of contigs for each respective clonotype in the first plurality of clonotypes, where each respective contig in the plurality of contigs comprises an indication of chain type for the respective contig, a barcode, from among a plurality of barcodes, for the respective contig, wherein the barcode is associated with a respective cell in the first plurality of cells from which the respective contig was constructed, and a contig consensus sequence of an mRNA of the respective cell. In the method, there is determined, using the first dataset, for each respective clonotype in the first plurality of clonotypes, a percentage, absolute number or proportion of the first plurality of cells that represent the respective clonotype. There is provided, on a first portion of the display a first two-dimensional visualization. A first axis of the first two-dimensional visualization represents individual clonotypes in the first plurality of clonotypes and a second axis of first the two-dimensional visualization represents the percentage, the absolute number or the proportion of the first plurality of cells that represent respective clonotypes. There is provided on a second portion of the display a listing of the first plurality of clonotypes.

In some embodiments, the first visualization is a bar chart.

In some embodiments, respective clonotypes in the first plurality of clonotypes are ordered on the second axis of the two-dimensional visualization by the percentage, absolute number or proportion of the first plurality of cells that have the respective clonotype.

In some embodiments, respective clonotypes in the first plurality of clonotypes are ordered in the listing by the percentage, absolute number or proportion of the first plurality of cells that have the respective clonotype.

In some embodiments, more than one cell in the first plurality of cells have the same clonotype in the first plurality of clonotypes. In some embodiments, more than ten cells in the first plurality of cells have the same clonotype in the first plurality of clonotypes.

In some embodiments, the first plurality of clonotypes comprises 25 clonotypes and the first plurality of cells includes at least one cell for each clonotype in the first plurality of clonotypes.

In some embodiments, the first plurality of clonotypes comprises 100 clonotypes and the first plurality of cells includes at least one cell for each clonotype in the first plurality of clonotypes.

In some embodiments, the first plurality of cells consists of B-cells from the single first subject.

In some embodiments, the listing includes for a first contig in the plurality of contigs for a first clonotype in the first plurality of clonotypes: an identifier for a V segment in the first contig, an identifier for a J region in the first contig, and an identifier for a C region in the first contig. In some such embodiments, the first contig is for an α chain or a γ chain. In some embodiments, the first contig is for a β chain or a δ chain and the first contig further includes an identifier for a D region in the first contig.

In some embodiments, the method further comprises providing an affordance on the display that allows a user to limit the number of clonotypes that are displayed in the first two-dimensional visualization and the listing to a number that is less than the first plurality of clonotypes in the first dataset.

In some embodiments, the method further comprises providing a first affordance, where, when a user toggles the first affordance, the display of the first two-dimensional visualization is replaced with a second two-dimensional visualization while maintaining the listing of the first plurality of clonotypes. In such embodiments, the second two-dimensional visualization provides a first filter for selection of one or more genes of a lymphocyte receptor represented by the first dataset. The second two-dimensional visualization also provides a second filter for one or more chain types. A first axis of the second two-dimensional visualization represents the one or more individual genes. A second axis of the second two-dimensional visualization represents the percentage, the absolute number or the proportion of the plurality of contigs present in the first dataset that include the one or more individual genes independently of how the one or more individual genes have been incorporated into clonotype. When a user toggles the first filter an identity of the one or more genes is selected. When a user toggles the second filter one or more chain types is selected, thereby limiting the percentage, the absolute number or the proportion of the plurality of contigs present in the first dataset that include the one or more individual genes to those contigs in the one or more chain types identified by the second filter that include the one or more individual genes. In some such embodiments, the first plurality of cells consists of B-cells from the single first subject, and the one or more genes is any combination of V gene, D gene, J gene, and C gene.

In some embodiments, a first contig in the plurality of contigs for a first clonotype in the first plurality of clonotypes in the first dataset for a respective cell in the first plurality of cells is between 600 and 800 bases in length and is determined from overlaying a plurality of sequence reads of the first contig, the plurality of sequence reads has an average read length that is less than 600 bases and, each sequence read in the plurality of sequence reads has the same unique molecular identifier.

In some embodiments, the first plurality of cells consists of B-cells from the single first subject.

In some embodiments, the single first subject is mammalian.

In some embodiments, the single first subject is mammalian, a reptile, avian, amphibian, fish, ungulate, ruminant, bovine, equine, caprine, ovine, swine, camelid, monkey, ape, ursid, poultry, dog, cat, mouse, rat, fish, dolphin, whale or shark.

In some embodiments, the method further comprises providing a first affordance, where, when a user toggles the first affordance, the display of the first two-dimensional visualization is replaced with a second two-dimensional visualization while maintaining the listing of the first plurality of clonotypes, the second two-dimensional visualization provides a first filter for selection of a pair of genes of a lymphocyte receptor represented by the first dataset, the second two-dimensional visualization provides a second filter for one or more chain types, a first axis of the second two-dimensional visualization represents a first individual gene in the pair of genes, and a second axis of the second two-dimensional visualization represents a second individual gene in the pair of genes and wherein each respective cell in a plurality of two-dimensional cells in the second two-dimensional visualization that intersects the first and second axis indicates a number of contigs of the one or more chain types designated by the second filter in the first dataset that includes the respective gene on the first axis and the respective gene on the second axis for the respective two-dimensional cell. In some such embodiments, the second two-dimensional visualization is a heat map, and the heat map provides a scale that provides a numeric indication in a color coded format of the number of contigs of the one or more chain types designated by the second filter in the first dataset that includes the respective gene on the first axis and the respective gene on the second axis for each two-dimensional cell in the plurality of two-dimensional cells of the second two-dimensional visualization.

In some embodiments, the method further comprises providing one or more affordances on the display, wherein the one or more affordances are configured to receive a user specified selection criterion. Responsive to receiving the user specified selection criterion, the listing is limited to those clonotypes in the first plurality of clonotypes that match the selection criterion. Further, the selection criterion is at least one contig, at least one barcode, at least one amino acid sequence, or at least one nucleic acid sequence.

In some embodiments, the method further comprises responsive to receiving the user specified selection criterion, further limiting the first two-dimensional visualization to the display of those clonotypes in the first plurality of clonotypes that match the selection criterion.

In some embodiments, the selection criterion includes a wild card thereby matching more than one contig, barcode, amino acid sequence, or nucleic acid sequence.

In some embodiments, the listing includes a plurality of rows, and each respective row in the plurality of rows specifies the indication of a chain type of a contig in the plurality of contigs for a clonotype in the first plurality of clonotypes. In such embodiments, the method further comprises, responsive to user selection of a row in the plurality of rows, replacing the display of the first two-dimensional visualization with a panel of summary information for the chain represented by the selected row, while maintaining the display of the listing. In some such embodiments, the panel of summary information comprises: a reference sequence that is a published curated sequence of the selected chain type, a consensus sequence from all the contigs in the first dataset that include the selected chain type, a representation of each respective contig in the first dataset that includes the selected chain type, and the reference sequence, the consensus sequence, each representation of each respective contig in the panel occupy a different row in the panel and are sequence aligned with respect to each other. In some embodiments, a representation of a respective contig includes one or more indicators, where the one or more indicators includes a start codon of the respective contig, a mismatch between the respective contig and the consensus sequence, a deletion incurred in the respective contig with respect to the consensus sequence, a stop codon of the respective contig, or a coding region of the respective contig. In some such embodiments, responsive to selection of the consensus sequence, the method further comprises displaying the entire consensus sequence in a format that is configured for user cutting and pasting into separate application running on the system.

In some embodiments, responsive to selection of a representation of a contig displayed in the panel of summary information, the method further comprises displaying information about the selected contig that includes one or more of a barcode for the contig, an identifier for the contig, a number of unique molecular identifiers supporting the contig, a number of sequence reads supporting the contig, a reference identity of a V gene for the contig, a reference identity of a D gene for the contig, a reference identity of J gene for the contig, and a reference identity of a C gene for the contig.

In some embodiments, the method further comprises displaying a toggle, and user selection of the toggle switches the representation of each respective contig in the first dataset that includes the selected chain type from one of (i) a graphical representation of each respective contig and (ii) a sequence of each respective contig, to the other of (i) the graphical representation of each respective contig and (ii) the sequence of each respective contig.

In some embodiments, responsive to selection of a representation of a first contig displayed in the panel of summary information, the method further comprises displaying an alignment of each sequence read in a plurality of sequence reads to the first contig, wherein each sequence read in the plurality of sequence reads has a unique molecular identifier that is associated with the first contig. In some embodiments, a plurality of unique molecular identifiers is associated with the first contig, and the method further comprises displaying a unique molecular identifier affordance that affords choosing between (i) selection of all the unique molecular identifiers in the plurality of unique molecular identifiers and (ii) selection of a single unique molecular identifiers in the plurality of unique molecular identifiers, when the single unique molecular identifier is selected, only those sequence reads for the first contig that have the single unique molecular identifier are displayed in the alignment of each sequence read in a plurality of sequence reads to the first contig.

In some embodiments, the method further comprises obtaining a second dataset representing a second plurality of cells from a single second subject, where the second dataset represents a second plurality of clonotypes, the first second dataset includes a plurality of contigs for each respective clonotype in the second plurality of clonotypes, wherein each respective contig in the plurality of contigs comprises: an indication of chain type for the respective contig, a barcode for the respective contig, wherein the barcode is associated with a respective cell in the second plurality of cells from which the respective contig was constructed, and a contig consensus sequence of an mRNA of the respective cell. In the method a determination is made, using the second dataset, for each respective clonotype in the second plurality of clonotypes, a percentage, absolute number or proportion of the second plurality of cells that represent the respective clonotype. Further in the method, a comparison of the first dataset to the second dataset is performed at a paired-clonotype, single-cell level that evaluates a number of cells with a given clonotype in the first dataset that match the clonotype of cells with the same clonotype in the second dataset thereby identifying a pairwise clonotype commonality between the first dataset and the second dataset. In some such embodiments, the pairwise clonotype commonality between the first dataset and the second dataset is a Morisita-Horn metric. In some such embodiments, the method further comprises displaying for each clonotype in a subset of the first plurality of clonotypes: a percentage, an absolute number or a proportion of the first plurality of cells that represent the respective clonotype in the first dataset, and a percentage, an absolute number or a proportion of the second plurality of cells that represent the respective clonotype in the second dataset. In some instances, the subset of the first plurality of clonotypes are those clonotypes in the first plurality of clonotypes that are each represented by at least a threshold percentage, absolute number or proportion of the first plurality of cells.

In some embodiments, the method further comprises displaying for each respective clonotype element in a plurality of clonotype elements: a percentage, an absolute number or a proportion of the contigs in the first dataset that include the respective clonotype element, and a percentage, an absolute number or a proportion of the contigs in the second dataset that include the respective clonotype element. In some such embodiments, each clonotype element in the plurality of clonotype elements is a different V gene sequence. In some embodiments, each clonotype element in the plurality of clonotype elements is a different D gene sequence. In some embodiments, each clonotype element in the plurality of clonotype elements is a different J gene sequence. In some embodiments, each clonotype element in the plurality of clonotype elements is a different C gene sequence.

In some embodiments, the first plurality of cells consists of B-cells from the single first subject, and the second plurality of cells consists of B-cells from the single second subject, and the method further comprises displaying for each respective B-cell isotype in a plurality of B-cell isotype: a percentage, an absolute number or a proportion of the first dataset that has the respective B-cell isotope, and a percentage, an absolute number or a proportion of the second dataset that has the respective B-cell isotope.

In some embodiments, the single first subject and the single second subject are the same subject.

In some embodiments, the single first subject and the single second subject are different subjects.

In some embodiment the method further comprises obtaining a second dataset representing a second plurality of cells from a single second subject, where the second dataset comprises a corresponding discrete attribute value for mRNA for each gene in a plurality of genes for each respective cell in the second plurality of cells, each corresponding discrete attribute value for mRNA for each gene in a plurality of genes for each respective cell in the second plurality of cells is supported by one or more barcodes in the plurality of barcodes, and individual respective cells in the first plurality of cells represented by the first dataset are present in the second plurality of cells and mappable between the first dataset and the second through the plurality of barcodes. In the method, the second dataset is clustered using the discrete attribute value for mRNA for each gene in the plurality of genes, or principal components derived therefrom, for each respective cell in the second plurality of cells thereby assigning each respective cell in the second plurality of cells to a corresponding cluster in a plurality of clusters, where each respective cluster in the plurality of clusters consists of a unique different subset of the second plurality of cells. In the method, a subset of the first plurality of cells is selected by selecting those cells in the first plurality of cells that map onto the cells in the second plurality of cells in a cluster selected from among the plurality of clusters. In the method, clonotype information from the first dataset for the subset of the first plurality of cells is displayed without displaying clonotype information for cells in the first plurality of cells outside of the subset of the first plurality of cells. In some such embodiments, the displaying clonotype information comprises providing a second two-dimensional visualization, where a first axis of the second two-dimensional visualization represents individual clonotypes represented in the subset of the first plurality of cells, and a second axis (e.g., orthogonal to first axis) of the two-dimensional visualization represents a percentage, an absolute number or a proportion of the subset of the first plurality of cells that represent respective clonotypes in the subset of the first plurality of cells.

In some embodiments, the single first subject and the single second subject are the same subject.

In some embodiments, the clustering the second dataset comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm.

In some embodiments, the clustering the second dataset comprises application of a Louvain modularity algorithm, k-means clustering, a fuzzy k-means clustering algorithm, or Jarvis-Patrick clustering.

In some embodiments, the clustering the second dataset comprises k-means clustering of the discrete attribute value dataset into a predetermined number of clusters. In some such embodiments, the predetermined number of clusters is an integer between 2 and 50.

Another aspect of the present disclosure provides a method for analyzing one or more datasets. The method comprises, at a computer system comprising a memory, a processor and a display: obtaining, using the processor, a first dataset representing a first plurality of cells from a single first subject, where the first dataset represents a first plurality of clonotypes, the first dataset includes a plurality of contigs for each respective clonotype in the first plurality of clonotypes, wherein each respective contig in the plurality of contigs comprises: an indication of chain type for the respective contig, a barcode, from among a plurality of barcodes, for the respective contig, wherein the barcode is associated with a respective cell in the first plurality of cells from which the respective contig was constructed, and a contig consensus sequence of an mRNA of the respective cell. In the methods, a determination is made, using the first dataset and the processor, for each respective clonotype in the first plurality of clonotypes, a percentage, absolute number or proportion of the first plurality of cells that represent the respective clonotype. Further in the method, there is provided on a first portion of the display a first two-dimensional visualization. A first axis of the first two-dimensional visualization represents individual clonotypes in the first plurality of clonotypes and a second axis of first the two-dimensional visualization represents the percentage, the absolute number or the proportion of the first plurality of cells that represent respective clonotypes. Further in the method there is provides on a second portion of the display a listing of the first plurality of clonotypes.

Still another aspect of the present disclosure provides a non-transitory computer readable storage medium. The non-transitory computer readable storage medium stores instructions, which when executed by a computer system having a display, causes the computer system to perform a method for analyzing one or more datasets, the method comprising: obtaining a first dataset representing a first plurality of cells from a single first subject, where the first dataset represents a first plurality of clonotypes, the first dataset includes a plurality of contigs for each respective clonotype in the first plurality of clonotypes. Each respective contig in the plurality of contigs comprises: an indication of chain type for the respective contig, a barcode, from among a plurality of barcodes, for the respective contig, wherein the barcode is associated with a respective cell in the first plurality of cells from which the respective contig was constructed, and a contig consensus sequence of an mRNA of the respective cell. In the method a determination is made, using the first dataset, for each respective clonotype in the first plurality of clonotypes, a percentage, absolute number or proportion of the first plurality of cells that represent the respective clonotype. Further in the method, there is provided on a first portion of the display a first two-dimensional visualization, wherein a first axis of the first two-dimensional visualization represents individual clonotypes in the first plurality of clonotypes and a second axis of first the two-dimensional visualization represents the percentage, the absolute number or the proportion of the first plurality of cells that represent respective clonotypes. Further in the method there is provided on a second portion of the display a listing of the first plurality of clonotypes.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to analyze datasets. An example of such datasets are datasets arising from sequencing pipelines that sequence the VDJ regions in single cells, such as B-cells and T-cells. Details of implementations are now described in conjunction with the Figures.

Figure 1:
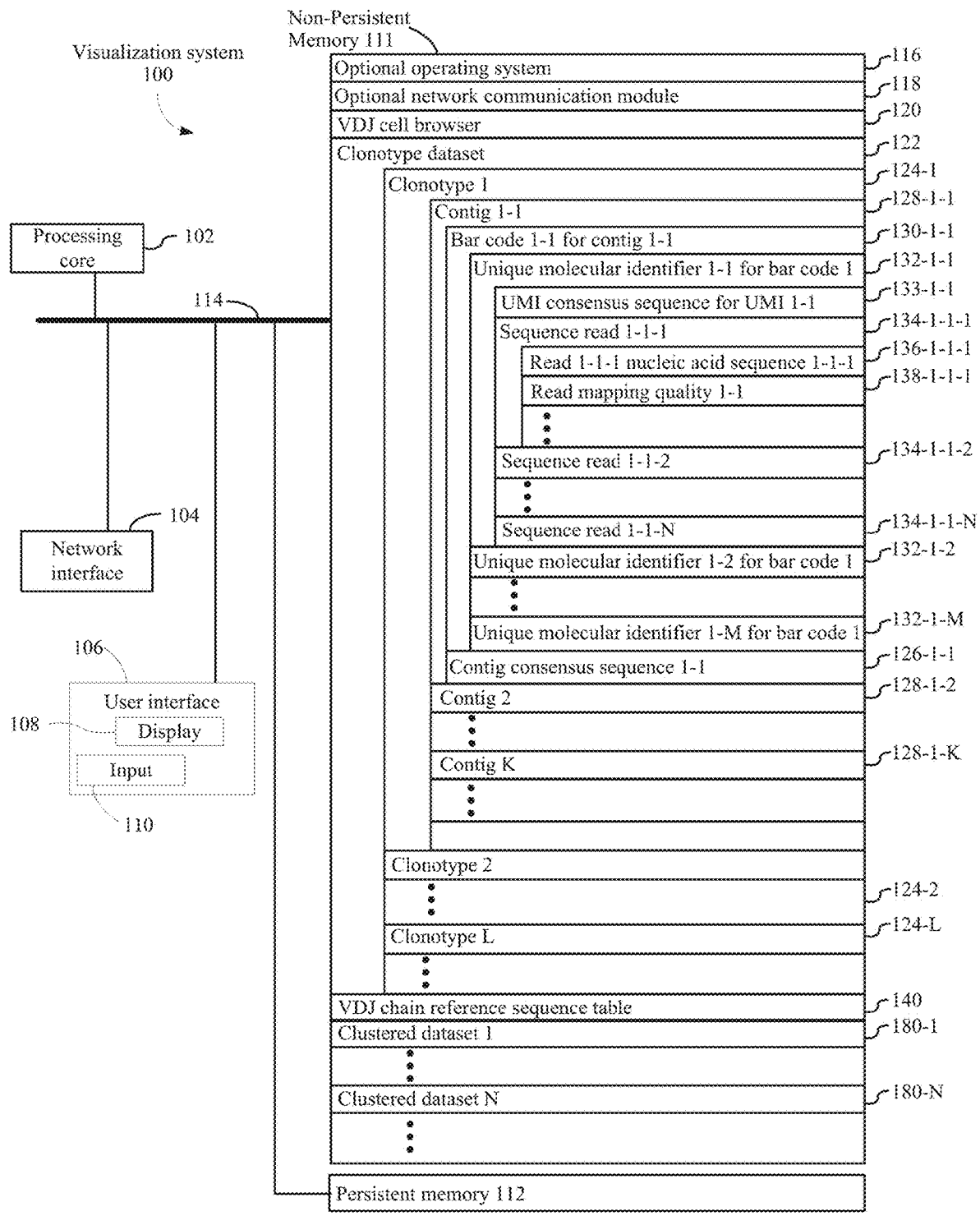
FIG. 1 is an example block diagram illustrating a computing device in accordance with some implementations.

FIG. 1 is a block diagram illustrating a visualization system 100 in accordance with some implementations. The device 100 in some implementations includes one or more processing units CPU(s) 102 (also referred to as processors), one or more network interfaces 104, a user interface 106, display 108 including input 110, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

an optional operating system 116, which includes procedures for handling various basic system services and for performing hardware dependent tasks;

an optional network communication module (or instructions) 118 for connecting the visualization system 100 with other devices, or a communication network;

a VDJ browser module 120 for selecting a clonotype dataset 122 (e.g., 122-1, 122-2, 122-Q) from persistent memory 112 and presenting an analysis of the clonotype dataset;

a clonotype dataset 122, the clonotype dataset comprising a plurality of clonotypes 124 (e.g., 124-1, 124-2, 124-L), and for each chain in each clonotype 124 (e.g. T-cell receptor α chain, T-cell receptor β chain, B-cell light chain, B-cell heavy chain, etc.) in the plurality of clonotypes a consensus sequence for a VDJ region 126 (e.g., 126-1-1) of the chain, where the consensus sequence for the VDJ region 126 is derived from a plurality of contigs 128 (e.g., 128-1-1, 128-1-2, 128-1-K) of that chain in that clonotype, each contig 128 associated with (i) a barcode 130 (e.g., 130-1-1, 130-1-1-1, 130-1-1-2, 130-1-1-1-M, 130-1-2-1, 130-1-2-M, 130-1-X-1, 130-1-X-M, 130-2-1-1, 130-2-1-M, 130-2-2-1, 130-2-1-M, 130-2-X-1, 130-2-X-M), (ii) one or more unique molecular identifiers 132 (e.g., 132-1-1, 132-1-2, 132-1-M) each with a UMI consensus sequence 133 (e.g., 133-1-D, and (iii) a contig consensus sequence 126 across the sequence reads of the unique molecular identifier, each unique molecular identifier 132 supported by a plurality of sequence reads 134 (e.g., 134-1-1-1, 134-1-1-2, 134-1-1-N) that contribute to the contig consensus sequence 126, each sequence read including information such as a read nucleic acid sequence 136 (e.g., 136-1-1-1) and a read mapping quality 138 (e.g., 138-1-1-1);

a VDJ chain reference sequence table 140 that includes the reference sequence of all the V genes and J genes in a genome, or at least the ones represented by a given clonotype dataset 122; and optionally, all or a portion of one or more clustered datasets 180 (equivalent to clustered dataset 128 of U.S. Patent Application No. 62/672,544), each clustered dataset 180 (e.g., 180-1, 180-2, 180-N) comprising a plurality of clusters 5002 (e.g., 5002-1-1, 5002-1-2, 5002-1-K, 5002-1-1-1, 5002-1-1-2, 5002-1-1-X, 5002-2-1-1, 5002-2-1-2, 5002-2-1-X), each cluster 5002 (equivalent to cluster 158 of U.S. Patent Application No. 62/672,544) including a subset of cells (second entities 126 of U.S. Patent Application No. 62/672,544) 5004 (e.g., 5004-1-1-1, 5004-1-1-2, 5004-1-1-M), and each respective cell identified by a barcode 130 that supports the cell.

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

In some embodiments clonotype dataset 122 is organized as a series of data blocks with a master JSON table of contents at the beginning of the file and a JSON table of contents describing the addresses and structure of each block at the end of the file. In some embodiments there are a plurality of blocks in the clonotype dataset 122.

In some embodiments, one such block constitutes a database (e.g., a sqlite3 database) containing one table each for clonotypes, lymphocyte (e.g. T-cells, B-cells) receptor chain reference sequences, lymphocyte (e.g. T-cells, B-cells) receptor chain consensus sequences 126, contigs 128, and a secondary table mapping cell barcodes 130 to clonotypes 124. This database is queried to create the clonotype list, sorted by frequency, and again queried to populate the chain visualization with data when clicking on the chain in the user interface disclosed herein. Each row in the reference, consensus and contig tables also include file offsets and lengths that encode the location of more detailed and hierarchical information about that entity within a set of JSON files, stored within other blocks in the plurality of block. Finally, alignment and sequence information for each reference and consensus are stored in the database for future debugging and troubleshooting.

In some embodiments, one or more blocks contain a reference annotation JSON file, which is a complete set of information about each reference per lymphocyte (e.g. T-cell, B-cell) receptor chain. This block is equivalent to VDJ chain reference sequence table 140. Accordingly, in some embodiments, VDJ chain reference sequence table 140 is a component of the clonotype dataset 122.

In some embodiments, one or more blocks contain a consensus annotation, e.g., as JSON file, which is a complete set of information about each consensus sequence 126 per lymphocyte (e.g. T-cell, B-cell) receptor chain.

In some embodiments, one or more blocks contains a contig annotation, e.g. as a JSON file, which is a complete set of information about each contig 128. A contig 128 is the assembled sequence of a transcript that encodes a chain (e.g. T-cell α chain, T-cell β chain, B-cell heavy chain, B-cell light chain) of a lymphocyte receptor (e.g., T-cell receptor, B-cell immunoglobulin). Thus, in the example case of a single T-cell it is expected that there would be at least one contig 128 for the α chain and at least one contig 128 for the β chain.

In some embodiments, one or more blocks contain a reference sequence, e.g., in FASTA format, that is used during clonotype dataset 122 file creation, not during VDJ browser 120 operation, for debugging purposes.

In some embodiments, one or more blocks contain a reference alignment, e.g. as a BAM file, which stores how chain consensus sequence/contigs 128 differ from the reference sequence. This is typically used during clonotype dataset 122 creation as opposed to during VDJ browser 120 operation, for instance, for debugging purposes.

In some embodiments, one or more blocks contain a reference alignment BAM index for the above identified BAM file to accelerates sequence alignment queries.

In some embodiments, one or more blocks contain a consensus sequence, e.g., in FASTA format, that is typically used during clonotype dataset 122 creation as opposed to during VDJ browser 120 operation.

In some embodiments, one or more blocks contain consensus alignments BAM file that stores how contig sequences differ from the consensus, that is typically used during clonotype dataset 122 creation as opposed to during VDJ browser 120 operation.

In some embodiments, one or more blocks contain a contig BAM index which stores where to find read information for individual contigs.

In some embodiments, one or more blocks contain a contig BED file that stores gene annotations for each contig.

In some embodiments, one or more blocks contain a contig FASTA file that stores sequences of each contig.

In some embodiments, there are two processes that are initiated when a user runs the VDJ browser 120 (i) a backend server process that reads the clonotype dataset 122 and returns JSON responses and (ii) a front-end web application that processes the JSON into a visualization, and handles user input. In some embodiments, the backend server process extracts the sqlite3 database bytes out of the clonotype dataset 122 into a temporary location. The server process holds a relation between a clonotype dataset 122 and its associated sqlite3 database file, discussed above, in memory, and directs all queries pertaining to a clonotype dataset 122 to that database. When shutting down, the server process cleans itself up by removing all database files that were opened during the session.

Although FIG. 1 depicts a "visualization system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in nonpersistent memory 111, some or all of these data and modules may be in persistent memory 112.

While a system in accordance with the present disclosure has been disclosed with reference to FIG. 1, a method in accordance with the present disclosure is now detailed with reference to FIGS. 2 through 49.

Figure 2:
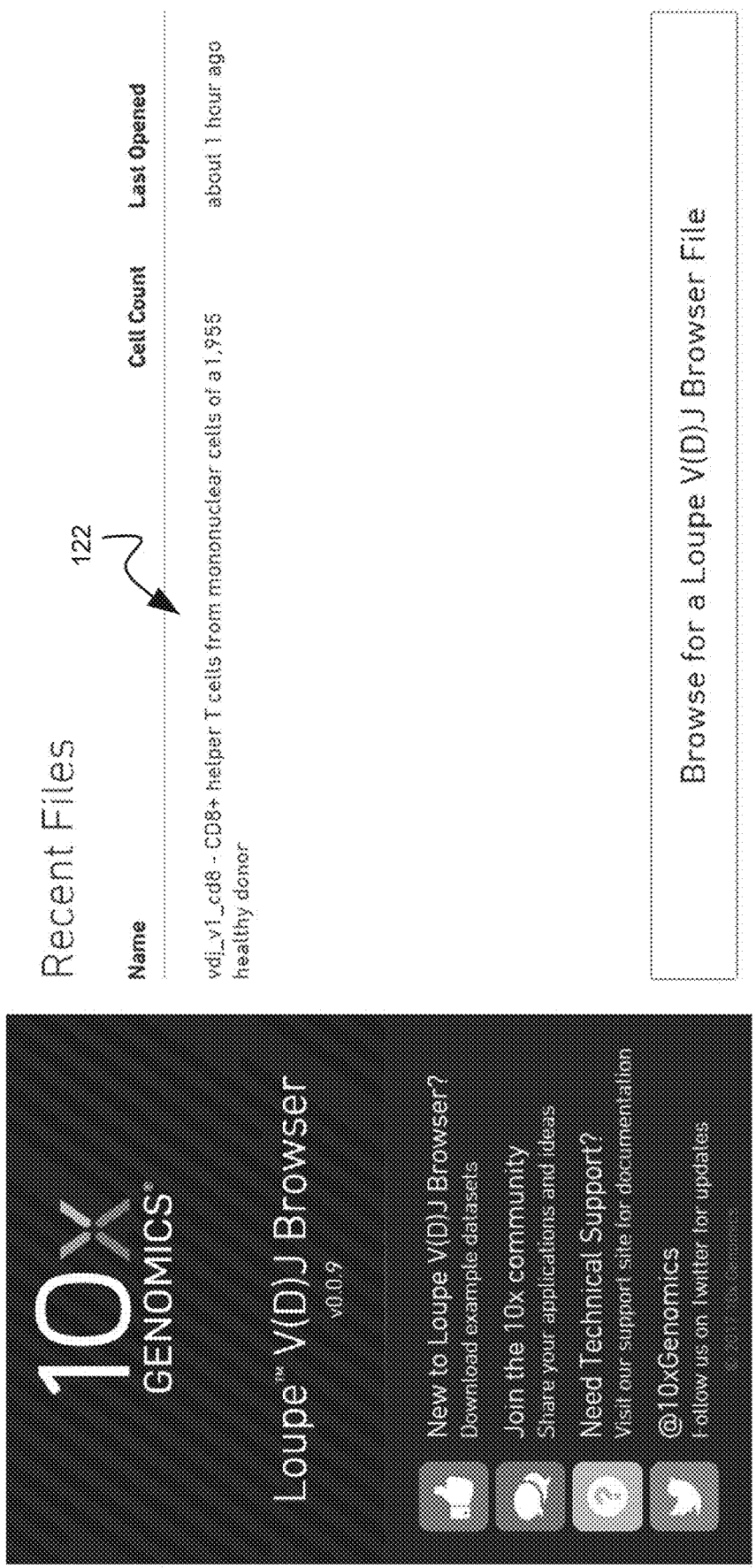
FIG. 2 illustrates a user interface for obtaining a dataset in accordance with some embodiments.
Figure 3:
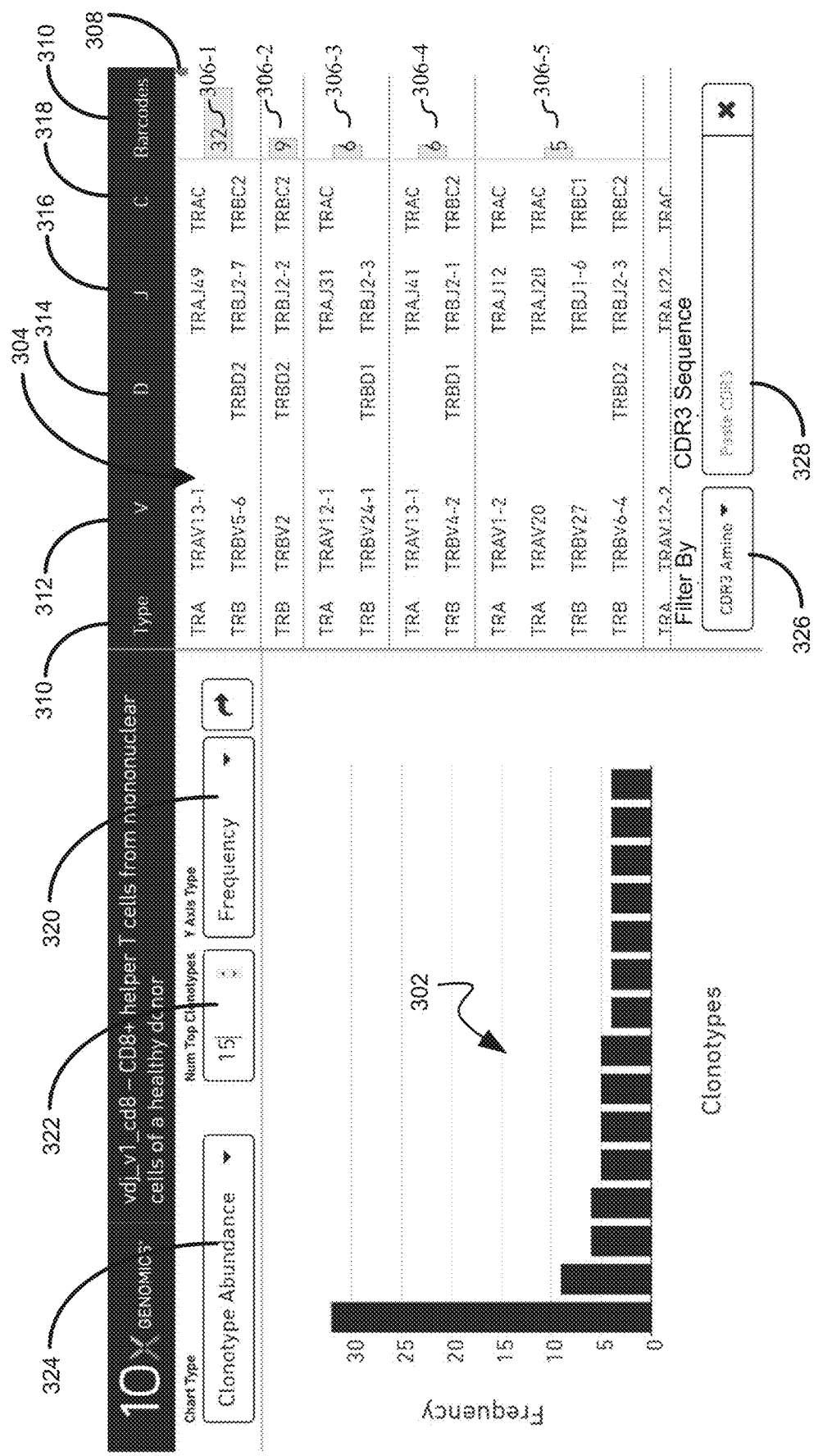
FIG. 3 illustrates an example display for visualizing clonotype abundance as a function of clonotype frequency in a population of cells in accordance with some embodiments.

FIG. 2 illustrates the initial panel that is displayed by the VDJ cell browser 120 when a user executes the VDJ cell browser 120 in some embodiments. In particular, FIG. 2 illustrates how the VDJ cell browser 120 provides some information regarding a given clonotype dataset 120 such as its name, the number of cells that are assumed to be represented by the dataset 122, and the last time the dataset was accessed. The number of cells that are assumed to be represented by the dataset is derived by evaluation of the number of barcodes 130 that are estimated to be uniquely associated with cells that express the targeted V(D)J transcript. In some embodiments, a respective barcode 130 is deemed to be uniquely associated with a cell if there exists within the clonotype dataset 122 a contig 128 that (i) is associated with the respective barcode 130 and (ii) is supported by at least two unique molecular identifiers 132 that each are supported by sequence reads 134 in the data set. In other words, each cell that is assumed to be represented by the clonotype dataset is supported within the dataset by a barcode 130 for a contig 128, where the contig, in turn, is supported by at least two different unique molecular identifiers 132, where each such unique molecular identifier is, in turn, supported by sequence reads 134 in the clonotype dataset. Upon selecting a clonotype dataset 122, process control turns to the display 302 of FIG. 3. FIG. 3 displays various data from a clonotype dataset 122. In particular, at a top level, nucleic acid sequences in the VDJ region of cells is organized by clonotypes 122 in some embodiments. In some embodiments, this sequence information, in the form of sequence reads 134, is obtained using a droplet based single-cell RNA-sequencing (scRNA-seq) microfluidics system that enables 3' or 5' messenger RNA (mRNA) digital counting of thousands of single cells. In such sequencing, droplet-based platform enables barcoding of cells.

The scRNAseq microfluidics system builds on the GemCode technology, which has been used for genome haplotyping, structural variant analysis and de novo assembly of a human genome. See Zheng et al., 2016 "Haplotyping germline and cancer genomes with high-throughput linked-read sequencing," Nat. Biotechnol. 34, pp. 303-311; Narasimhan et al., 2016, "Health and population effects of rare gene knockouts in adult humans with related parents," Science 352, pp. 474-477 (2016); and Mostovoy et al., 2016, "A hybrid approach for de novo human genome sequence assembly and phasing," Nat. Methods 13, 587-590, each of which is incorporated by reference, for a general description of GemCode technology. Such sequencing uses a gel bead-in-emulsion (GEM).

GEM generation takes place in a multi-channel microfluidic chip that encapsulates single gel beads at a predetermined fill rates, such as approximately 80%. For the clonotype datasets 122 of the present disclosure, in some embodiments, a 5' gene expression protocol is followed rather than a 3' gene expression protocol. In the case where the sample comprises T-cells, this provides full-length (5' UTR to constant region), paired T-cell receptor (TCR) transcripts from a number of (e.g., 100-10,000) individual lymphocytes per sample. In the case where the sample comprises B-cells, this provides full-length (5' UTR to constant region), paired B-cell immunoglobulin heavy chain and light chain transcripts from a number of (e.g., 100-10, 000) individual lymphocytes per sample.

In some embodiments, as in the case of the 3' gene expression protocol described in Zheng et al., id., the 5' expression protocol includes partitioning the cells into GEMs. In particular, in some embodiments, single cell resolution is achieved by delivering the cells at a limiting dilution, such that the majority (~90-99%) of generated GEMs contains no lymphocyte (cell), while the remainder largely contain a single lymphocyte. In some embodiments, upon dissolution of the single cell 5' gel bead in a GEM, oligonucleotides containing (i) a read 1 sequencing primer (e.g., ILLUMINA R1 sequence), (ii) a barcode 130, (iii) a unique molecular identifier (UMI) 132, and (iv) a switch oligonucleotide are released and mixed with cell lysate and a master mix that contains poly(dT) primers. Incubation of the GEMs then produces barcoded, full-length cDNA from poly-adenylated mRNA. After incubation, the GEMs are broken and the pooled fractions are recovered. In some embodiments, magnetic beads (e.g., silane beads) are used to remove leftover biochemical reagents and primers from the post GEM reaction mixture. The barcoded, full-length V(D)J segments from lymphocyte cDNA are enriched by PCR amplification prior to library construction. In some embodiments, enzymatic fragmentation and size selection are used to generate variable length fragments that collectively span the V(D)J segments of the enriched receptor chains prior to library construction.

In some embodiments, R1 (read 1 primer sequence) is added to the molecules during GEM incubation. P5 is added during target enrichment. P7, a sample index and R2 (read 2 primer sequence) are added during library construction via end repair, A-tailing, adaptor ligation and implementation of the polymerase chain reaction (PCR). The resulting single cell V(D)J libraries contain the P5 and P7 primers used in Illumina bridge amplification. See the Internet, at assets-.contentful.com/an68im79xiti/
26tufAiwI0KCYA0ou2gCWK/
8d313d2b126a7a1652d13810 73e72015/ CG000086_SingleCellVDJReagentKitsUserGuide_RevA.pdf, last accessed May 18, 2017, pp. 2-4, which is hereby incorporated by reference. See also, "Multiplexed Sequencing with the Illumina Genome Analyzer System," copyright 2008, on the Internet at www.illumina.com/documents/products/datasheets/datasheet_sequencing_multiplex.pdf, last accessed May 18, 2017, hereby incorporated by reference, for documentation on the P5 and P7 primers. In some embodiments, the sequenced single cell V(D)J library is in the form of a standard ILLUMINA BCL data output folder. In some such embodiments, the BCL data includes the paired-end Read 1 (comprising the barcode 130, the UMI 132, the switch oligonucleotide, as well as the 5' end of a receptor chain cDNA) and Read 2 (comprising a random part of the of the same receptor chain cDNA) and the sample index in the i7 index read. In some embodiments, a computer program such as the 10× CELL RANGER analysis pipeline performs secondary analysis on the BCL data such as using the barcodes 130 to group read pairs from the same cells, assemble full-length V(D)J segments in the form of contigs 128, and thereby create the clonotype dataset 122

The multiple sequence reads 134 with the same barcode 130 form at least one contig 128, and each such contig 128 represents a chain (e.g., T-cell receptor α chain, T-cell receptor β chain, B-cell heavy chain, B-cell light chain) of a single cell. The contig consensus sequence 126 for each of the contigs 128 of a cell are collectively used to determine the clonotype 124 of the cell. Stated differently, sequence reads 134 are grouped by barcode 130, and contigs 128 are assembled by looking at sequence reads 134 with the same UMI identifier 132. A set of chain consensus sequences, including a CDR3 region, is created by analyzing the common bases in the contigs 128. Cells with like CDR3 regions within these consensus sequences are grouped into clonotypes 124, and bar chart 302 of FIG. 3 shows the number of unique barcodes 130 in each clonotype. That is, FIG. 3 provides a bar chart 302 of the frequency of occurrence of particular clonotypes 124 in the 1955 cells 128 that are in the particular clonotype dataset 122 that is being illustrated by the VDJ browser 120. In this particular dataset, the cells used for sequencing are T-cells. As such, each contig 128 includes the third complementarity-determining region (CDR3) whose nucleotide sequence is unique to each T-cell clone. In the case of T-cells, the CDR3 interacts with the peptide and thus is important for recognizing pathogen or autoantigen epitopes. The CDR3 region is a subset of the V-J region (indicated by the darker bar 918 in FIG. 9), spanning the V gene and J gene in T-cell receptor α chains and the V, D and J genes in T-cell receptor β chains.

In some embodiments, the clonotype dataset 122 includes the V(D)J clonotype of the T-cell receptor of any T-cells or B-cell immunoglobulins of any B-cells that were in the biological sample represented by the clonotype dataset 122. The clonotypes of T-cells and B-cells is described below.

T-Cell Clonotypes.

Most T-cell receptors are composed of an alpha chain and a beta chain. The T-cell receptor genes are similar to B-cell immunoglobulin genes discussed below in that they too contain multiple V, D and J gene segments in their beta chains (and V and J gene segments in their alpha chains) that are rearranged during the development of the lymphocyte to provide the cell with a unique antigen receptor. The T-cell receptor in this sense is the topological equivalent to an antigen-binding fragment of the antibody, both being part of the immunoglobulin superfamily. B-cells and T-cells are defined by their clonotype, that is the identity of the final rearrangement of the V(D)J regions into the heavy and light chains of a B-cell immunoglobulin, in the case of B-cells, or into each chain of the T-cell receptor in the case of T-cells.

There are two subsets of T-cells based on the exact pair of receptor chains expressed. These are either the alpha (α) and beta (β) chain pair, or the gamma (γ) and delta (δ) chain pair, identifying the αβ or γδ T-cell subsets, respectively. The expression of the β and δ chain is limited to one chain in each of their respective subsets and this is referred to as allelic exclusion (Bluthmann et al., 1988, "T-cell-specific deletion of T-cell receptor transgenes allows functional rearrangement of endogenous alpha- and beta-genes," Nature 334, pp. 156-159; and Uematsu et al., 1988, "In transgenic mice the introduced functional T-cell receptor beta gene prevents expression of endogenous beta genes," Cell 52, pp. 831-841, each of which is hereby incorporated by reference). These two chains are also characterized by the use of an additional DNA segment, referred to as the diversity (D) region during the rearrangement process. The D region is flanked by N nucleotides which constitutes the NDN region of the CDR3 in these two chains. The CDR3 of each of the two receptor chains defines the clonotype 124 that is analyzed in FIG. 3. For αβ T-cells the CDR3 is in most contact with the peptide bound to the MHC. See Rudolph et al., 2006, "How TCRs bind MHCs, peptides, and coreceptors," Annu Rev Immunol 24:pp. 419-466, doi: 10.1146/annurev.immuno1.23.021704.115658, which is hereby incorporated by reference. For this reason, CDR3 sequences have been the main focus for immunological sequencing studies. See Yassai et al., 2009, "A clonotype nomenclature for T cell receptors," Immunogenetics 61, pp. 493-502, which is hereby incorporated by reference.

B-Cell Clonotypes.

B-cells are highly diverse, each expressing a practically unique B-cell immunoglobulin (e.g., B-cell immunoglobulin receptor—BCR). There are approximately $10^{10}$-$10^{11}$ B-cells in a human adult. See Ganusov et al., 2007, "Do most lymphocytes in humans really reside in the gut?," Trends Immunol, 208(12), pp. 514-518, which is hereby incorporated by reference. B-cells are important components of adaptive immunity, and directly bind to pathogens through B-cell immunoglobulin receptors (BCRs) expressed on the cell surface of the B-cells. Each B-cell in an organism (e.g. human) expresses a different BCR that allows it to recognize a particular set of molecular patterns. Individual B-cells gain this specificity during their development in the bone marrow, where they undergo a somatic rearrangement process that combines multiple germline-encoded gene segments to procures the BCR, as illustrated in FIG. 1 of Yaari and Kleinstein, 2015, "Practical guidelines for B-cell repertoire sequencing analysis," Genome Medicine 7:121, which is hereby incorporated by reference. Human antibody molecules (and B-cell immunoglobulins) are composed of heavy and light chains (each of which contains both constant (C) and variable (V) regions), which are encoded by genes on three loci: the immunoglobulin heavy locus (IGH@) on chromosome 14, containing the gene segments for the immunoglobulin heavy chain, the immunoglobulin kappa (κ) locus (IGK@) on chromosome 2, containing the gene segments for part of the immunoglobulin light chain, the immunoglobulin lambda (λ) locus (IGL@) on chromosome 22, containing the gene segments for the remainder of the immunoglobulin light chain. Each heavy chain and light chain gene contains multiple copies of three different types of gene segments for the variable regions of the antibody proteins. For example, the human immunoglobulin heavy chain region contains two Constant (Cμ and Cδ) gene segments and 44 Variable (V) gene segments plus 27 Diversity (D) gene segments and 6 Joining (J) gene segments. See Matsuda et al., 1998, "The complete nucleotide sequence of the human immunoglobulin heavy chain variable region locus," The Journal of Experimental Medicine. 188 (11): 2151-62, doi:10.1084/jem.188.11.2151; and Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi:10.1182/blood-2003-11-3857, each of which is incorporated by reference. The light chains also possess two constant (Cμ and Cδ) gene segments and numerous V and J gene segments, but do not have D gene segments. DNA rearrangement causes one copy of each type of gene segment to go in any given lymphocyte, generating an enormous antibody repertoire, although some are removed due to self-reactivity.

Because of the rearrangement undergone of the V(D)J region in T-cells and B-cells, only parts of the V(D)J regions (the V, D, and J segments) can be traced back to segments encoded in highly repetitive regions of the germline that are not typically sequenced directly from the germ line DNA. Furthermore, the V, D, and J segments can be significantly modified during the V(D)J rearrangement process and through, in the case of B-cells, somatic hypermutation. As such, there are typically no pre-existing full-length templates to align to sequence reads of the V(D)J regions of T-cell receptors and B-cell immunoglobulins. Clonal grouping, referred to herein as clonotyping, involves clustering the set of B-cell immunoglobulin V(D)J) sequences (in the case of B-cells) or the set of T-cell receptor V(D)J sequences, in the case to T-cells into clones, which are defined as a group of cells that are descended from a common ancestor. Unlike the case of T-cells, members of a B-cell clone do not carry identical V(D)J sequences, but differ because of somatic hypermutation. Thus, defining clones (clonotyping) based on BCR sequence data requires machine learning techniques in some instances. See, for example, Chen et al., 2010, "Clustering-based identification of clonally-related immunoglobulin gene sequence sets," Immunome Res. 6 Suppl 1: S4; and Hershberg and Prak, 2015, "The analysis of clonal expansion in normal and autoimmune B-cell repertoires," Philos Trans R Soc Lond B Biol Sci. 370(1676), each of which is hereby incorporated by reference.

In general, the VDJ cell browser 120 can be used to analyze clonotyping datasets prepared from T-cells or B-cells. In the case of T-cells, clonotyping identifies the unique nucleotide CDR3 sequences of a T-cell receptor chain, which constitute V, D, and J segments. In accordance with the systems and methods of the present disclosure, this generally involves PCR amplification of the mRNA obtained using the above described scRNAseq microfluidics system in which each GEM encapsulates a single cell, employing V-region-specific primers and either constant region (C) specific or J-region-specific primer pairs, followed by nucleotide sequencing of the amplicon.

The VDJ cell browser 120 is applicable to genes that code for the B-cells (the antibodies) and T-cells (the T-cell receptors). As discussed above, T-cells and B-cells get their diversity by a recombination process involving the V, D, J and C germ line regions. So each T-cell and B-cell encodes a unique clonotype.

Sequence reads 134 obtained from mRNA encoding all or portions of a cell receptor chain for an individual cell are used to derive a contig 128 that includes the CDR3 region. Each of the contigs 128 for a given cell will have a common barcode 130 thereby defining the set of contigs for the given cell and, correspondingly, the set of CDR3 sequences for the given cell. The CDR3 region across the set of contig consensus sequences 126 for the given cell thereby determines the clonotype 124 of the cell. Thus, graph 302 represents the frequency of clonotype 124 occurrence across the plurality of cells represented in a clonotype dataset 122. In the biological sample represented by the clonotype dataset 122, each clonotype has some number of cells of a particular clonotype. These clonotypes are sorted by frequency of clonotype occurrence. Table 304 lists out the clonotype information that is summarized in graph 304. Each box 306 in table 304 is the clonotype 124 of a particular set of contigs. There may be multiple cells represented by this clonotype in the clonotype dataset 122. For instance, in the biological sample represented by dataset 122, there are 32 T-cells that have the clonotype described in box 306-1, 9 T-cells that have the clonotype described in box 306-2, 6 T-cells that have the clonotype described in box 306-3, 6 T-cells that have the clonotype described in box 306-4, and 5 T-cells that have the clonotype described in box 306-5.

Clonotype 306-1 includes one contig type for a T-cell α chain and another contig type for a T-cell β chain. That is, each of the contigs for a T-cell α chain for clonotype 306-1 have a same first CDR3 sequence, and each of the contigs for a T-cell β chain for clonotype 306-1 have a same second CDR3 sequence. By contrast, clonotype 306-5 includes two contig types for a T-cell α chain and another two contig types for a T-cell β chain. That is, each of the contigs for a T-cell α chain for clonotype 306-1 have either a first or second CDR3 sequence, and each of the contigs for a T-cell β chain for clonotype 306-1 have either a third or fourth CDR3 sequence.

Further, toggle 308 can be used to scroll further down in table 304 to reveal the clonotypes and frequency (or number) of additional T-cells in the biological sample represented by dataset 122. For each clonotype, table 304 details each chain type 310 represented in the clonotype 124. A clonotype may have multiple chain consensus sequences, these chain consensus sequences are grouped into clonotypes for the reasons cited above. Two cells have the same clonotype if they share the set of same CDR3s for each distinct chain consensus sequence derived from its contigs.

For each clonotype 306, table 304 details each chain type 310 represented by that clonotype. In the case of clonotype 306-1, there is a single α chain type and a single β chain type meaning that all of the α chains for this clonotype 306-1 have the same first CDR3 sequence and all of the β chains for this clonotype 306-1 have the same second CDR3 sequence For each chain type 310 represented in a clonotype, table 304 provides an identifier for the V segment 312, an identifier for the diversity region 314 (present in the case of T-cell β chains and δ chains, but not α chains and γ chains), an identifier for the J region 316, and an identifier for the C region 318. Two cells are deemed to have the same clonotype if their respective receptor chains have the same corresponding CDR3 sequences.

In the case where the sample comprises T-cells, due to the heterozygous nature of the cells being sampled, it is possible for a single cell in the sample represented by the clonotype dataset illustrated in FIG. 1 to have up to two different α chains as well as up to two different β chains. In other words, due to the heterozygous nature of the cells being sampled, it is possible for a single cell in the sample represented by the clonotype dataset illustrated in FIG. 1 to have a first α chain with a first CDR3 sequence, a second α chain with a second CDR3 sequence, a first β chain with a third CDR3 sequence, and a second β chain with a fourth CDR3 sequence.

Figure 4:
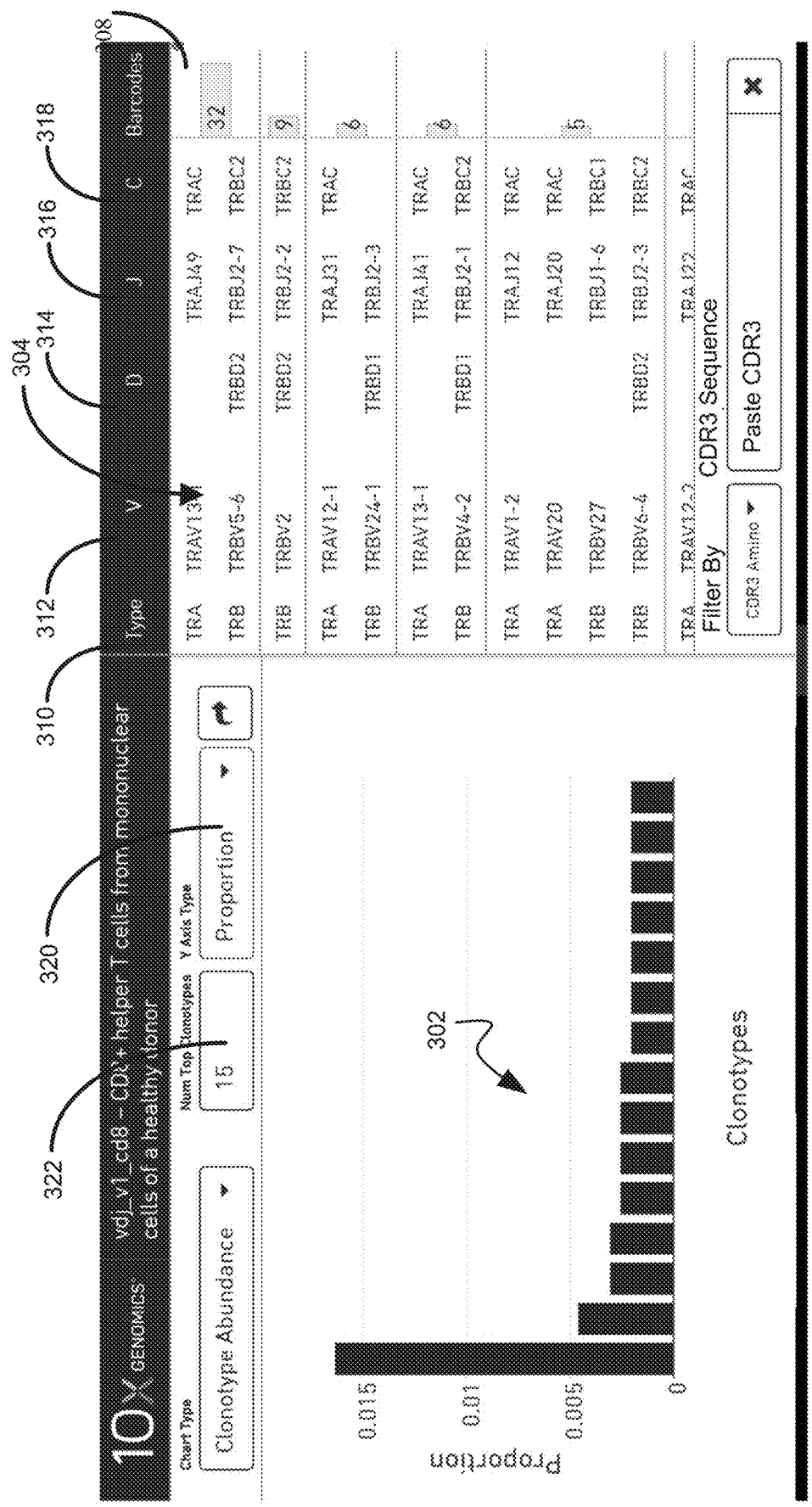
FIG. 4 illustrates an example display for visualizing clonotype abundance as a function of clonotype proportion in a population of cells in accordance with some embodiments.

Advantageously, VDJ browser allows for the analysis of the clonotype information in a variety of different ways. FIG. 3 illustrates the default chart 302 when a clonotype dataset 122 is first loaded. Toggle 320 allows for chart 302 to be toggled between displaying (i) frequency in terms of total number of cells per clonotype as illustrated in FIG. 3 and (ii) proportion in terms of total number of cells per clonotype as illustrated in FIG. 4.

Affordance 322 is used to specify the total number of clonotypes, from among all the clonotypes in a clonotype dataset 122 under analysis that are displayed in chart 302 and table 304. Presently, as illustrated in FIG. 3, the top 15 represented clonotypes are under analysis. In some embodiments, the clonotype dataset includes contigs for 50 or more clonotypes, 100 or more clonotypes, 500 or more clonotypes or 1000 or more clonotypes. As such, examination of clonotype frequency of all the clonotypes in the dataset 122 may prove to be too cumbersome in some instances, particularly when considering that most of the least represented clonotypes are present on a unitary basis. Affordance 322 allows the user to optimize the display for various use cases and clonotype datasets 122. The user can use affordance 322 to dial up to the total number of clonotypes in the dataset 122 under analysis or ratchet down the number of clonotypes displayed to a limited number, such as 15, as illustrated in FIG. 3.

Toggle 324 is used to select other chart types that can be applied to the clonotype 124 dataset. For instance, turning to FIG. 5, rather than viewing clonotype abundance in a clonotype dataset 122, V gene usage across the cells of the biological sample used to form the clonotype dataset 122 can be examined. The V gene usage is the annotated V region counted for each of the clonotypes. In other words, V gene usage is an aggregate of all V gene usage of each of the possible different human V genes (e.g., TRAV-1, TRAV4, TRAV8-2, TRAV9-2, etc.) plotted by frequency, regardless of which chain the represented V genes occurs in. Thus, in the case of the V gene TRAV1-1, a count of each instance of this V gene, regardless of occurrence in an α chain or β chain, across the clonotype dataset 122 is provided. Moreover, affordance 322 can now be used to select chain type (e.g., α chain only, β chain only, both α chain and β chain, etc. in the case of T-cells, heavy chain only, light chain only, both heavy chain and light chain, etc., in the case of B-cells). For instance, if affordance 322 is changed to α chain only, graph 502 only displays the frequency of occurrence of each V gene type across the α chains that occur in the clonotype dataset 122.

In some embodiments, if a cell represented in the clonotype dataset 122 does not have a V region or a J region, it is filtered out of the views provided by the VDJ browser. This occurs in some instances. The VDJ region is about 700 bases in length whereas, in some embodiments, the sequence reads 134 are about 150 base pairs long. Therefore, situations arise in which some mRNA molecules encoding the VDJ region only get sequence reads 134 on one part of the VDJ region (V only or J only) and not the other part of the VDJ region and so the V region or the J region is not represented for such mRNA molecules. In such instances, it is not possible to determine the clonotype of such cells. In some instances, in order to have an assigned clonotype, some embodiments of the present disclosure impose the condition that there has to be within a single cell a read with a particular UMI code that aligns to a V gene and another read with the particular UMI code that aligns to a J gene. In the alternative, longer sequence reads are employed that align to the entire VDJ region. In the alternative still, sequence reads having the same UMI are employed that collectively align to the entire VDJ region.

Figure 5:
FIG. 5 illustrates an example display for visualizing V region usage across T-cell receptor α chains and T-cell receptor β chains in a population of cells in accordance with some embodiments.

The advantage of the clonotype data illustrated in FIGS. 3 and 4 is that all the components (V, D, J) contributing to clonotypes have been robustly paired. However, FIG. 5 shows how the VDJ browser can be used to analyze components of a clonotype. FIG. 5 illustrates specific V region usage in a clonotype dataset. This is advantageous because immunologists are used to analyzing data in this manner because traditionally they have not had mechanisms for robustly pairing all the components of a clonotype. Thus, an immunologist can use toggle 324 to examine V region usage across a clonotype dataset 122 or J region usage across a clonotype dataset 122 independently of how such V regions or J regions have been incorporated into clonotypes for suitable legacy purposes. In this way, workers can compare clonotype datasets 122 to older experiments (e.g., for validation or comparative purposes).

Figure 6:
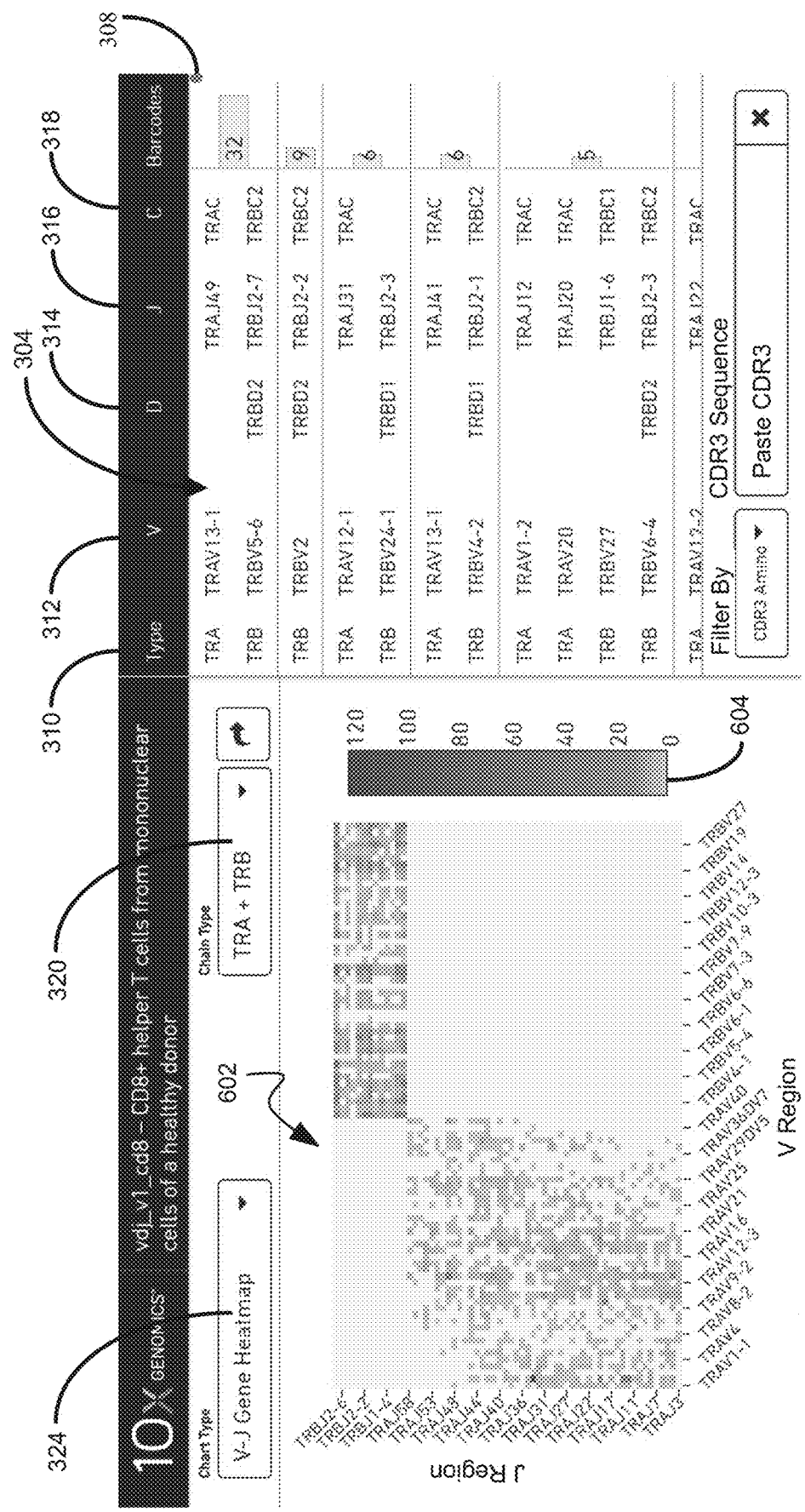
FIG. 6 illustrates an example display for visualizing the number of particular V region/J region pairs of individual T-cell receptor α chains and T-cell receptor β chains in a population of cells represented by a clonotype dataset in accordance with some embodiments.

Turning to FIG. 6, another chart type 602 that can be used to analyze a clonotype dataset 122 is disclosed. Chart type 602 provides a heat map of V and J region usage across the VDJ sequence of lymphocyte receptor chains in a population of cells represented by the clonotype dataset 122. For instance, in the case of T-cells, chart type 602 provides a heat map of V and J region usage across the VDJ sequence of T-cell receptor α chains and T-cell receptor β chains in a population of cells represented by the clonotype dataset 122. In the case of B-cells, chart type 602 provides a heat map of V and J region usage across the V(D)J sequence of B-cell immunoglobulin heavy chains and B-cell immunoglobulin light chains in a population of cells represented by the clonotype dataset 122.

As noted above, each chain has a V region 312 and a J region 316. Each x-y cell in the heat map of chart 602 provides an indication of the number of contigs present in the clonotype dataset 122 whose CDR3 region contains a receptor chain that contains a corresponding pair of a respective V region and a respective J region from among the V regions and J regions represented. For instance, in the case of B-cells, each x-y cell in the heat map of chart 602 provides an indication of the number of contigs present in the clonotype dataset 122 whose CDR3 region contains a heavy chain or a light chain that contains a corresponding pair of a respective V region and a respective J region from among the V regions and J regions represented. In the case of T-cells, each x-y cell in the heat map of chart 602 provides an indication of the number of contigs present in the clonotype dataset 122 whose CDR3 region contains an α chain or a β chain that contains a corresponding pair of a respective V region and a respective J region from among the V regions and J regions represented. Turning to FIG. 602 to illustrate, one x-y cell in the chart 602 indicates the number of contigs present in the clonotype dataset 122 that contains a TRAV-1-1 V region and a TRAJ3 J region.

Accordingly some embodiments of the present disclosure provide a second two-dimensional visualization (602) while maintaining the listing of the plurality of clonotypes (304). The second two-dimensional visualization (602) provides a first filter (324) for selection of a pair of genes of a lymphocyte receptor represented by the dataset. The second two-dimensional visualization (602) provides a second filter (320) for one or more chain types. A first axis of the second two-dimensional visualization represents a first individual gene (e.g., J Region axis of visualization 602 of FIG. 6) in the pair of genes, and a second axis (e.g., V Region axis of visualization 602 of FIG. 6) of the second two-dimensional visualization represents a second individual gene in the pair of genes. Each cell (of the two-dimensional visualization) that intersects the first and second axis indicates a number of contigs of the one or more chain types designated by the second filter (320) in the dataset that includes the respective gene on the first axis and the respective gene on the second axis.

Scale 604 provides a basis for interpreting the x-y cells in the chart 602. In some embodiments, the heat map is color coded between a first color that indicates a first number of contigs (e.g., green, representing zero contigs) and a second number of contigs (e.g., blue, representing 120 contigs). Thus, when this color coding is used in the heat map 602, if the x-y cell in the chart 602 indicating the number of contigs present in the clonotype dataset 122 whose clonotype contains a TRAV-1-1 V region and a TRAJ3 J region is colored green, that means that there are no contigs in the clonotype dataset 122 that contain a TRAV-1-1 V region and a TRAJ3 J region. On the other hand, if the x-y cell in the chart 602 indicating the number of contigs present in the clonotype dataset 122 that contains a TRAV-1-1 V region and a TRAJ3 J region is colored blue, that means there are 120 contigs in the clonotype dataset 122 that contain a TRAV-1-1 V region and a TRAJ3 J region. In such embodiments, intermediate values between zero and 120 are represented by intermediate color shades between green and blue. It will be appreciated that scale 604 adjust to the values of the data being represented, with the maximum value representing the maximum possible contigs present in the dataset with a particular V region/J region pair. It will further be appreciated that different color palettes can be used in the heat map or, in fact, the heat map can be grey scaled. As such, referring to FIG. 6, some embodiments of the present disclosure provide a second two-dimensional visualization (602) in the form of a heat map. The heat map provides a scale (604) that provides a numeric indication in a color coded format of the number of contigs of the one or more chain types designated by the second filter (320) in the dataset that includes the respective gene on the first axis and the respective gene on the second axis for each cell in the plurality of cells of the second two-dimensional visualization.

It will be noted that heat map 602 includes large blank regions in the upper left and lower right coordinates that include no data. This is because heat map 602 is showing data for the CDR3 region from both α chains and β chains to T-cells. It is typically not of interest to match the V region of a given α chain with the J region of a given β chain even when the two chains are from the same cell. It is further typically not of interest to match the J region of a given α chain with the V region of a given β chain even when the two chains are from the same cell. Exclusion of such matchings give rise to the blank regions in the upper left quadrant and lower right quadrant of heat map 602. In the view illustrated in FIG. 6, in the case of T-cells, affordance 320 can be used to toggle the heat map 602 so that it only displays V region/J region pairs on α chains only, on β chains only, or, as illustrated in FIG. 6, on both α chains and β chains. In the view illustrated in FIG. 6, in the case of B-cells (not shown in FIG. 6), affordance 320 can be used to toggle the heat map 602 so that it only displays V region/J region pairs on heavy chains only, on light chains only, or on both heavy chains and light chains.

Turning to column 320 of FIG. 3, the summary information provided in FIGS. 3 through 6 indicate how may barcodes 130 are represented by each clonotype in the clonotype dataset. Each box 306 represents a different clonotype 124, which roughly map to the cells that have the clonotype in the clonotype dataset. In some embodiments, there are doublets, meaning that a single GEM included two cells and thus the same barcode 130 for the GEM is associated with two different cells. Doublets may also be caused by multiple chains per clonotype. In the case of T-cells, doublets may also cause multiple α chains or β chains per clonotype. In the case of B-cells, doublets may also cause multiple heavy chains or light chains per clonotype. Such doublets disturb the 1 to 1 correspondence between barcodes and cell count. In some embodiments, the incidence of such doublets in the clonotype data set 122 (doublet rate) is less than 3%. In some embodiments, the incidence of such doublets in the clonotype data set 122 (doublet rate) is less than 2%. In some embodiments, the incidence of such doublets in the clonotype data set 122 (doublet rate) is less than 1%. In some embodiments, the incidence of such doublets in the clonotype data set 122 (doublet rate) is less than 0.5%. In some embodiments, the incidence of such doublets in the clonotype data set 122 (doublet rate) is less than 0.05%.

FIG. 3 indicates that clonotype 306-5 includes two different α chains and two different β chains. There are several reasons for such occurrence. One is that sometimes T-cells express two different α chains and two different β chains. This is because of the heterozygous nature of the cells being analyzed. In the case of T-cells, this is considered to be rare, generally. But it happens at some rate. There is a mechanism by which the T-cell (or B-cell) tries to stop the second arrangement (the second instance of a different α chain/β chain) from happening. However, sometimes cells will escape the process against such occurrence. If they do, then the single cell sequencing that includes unique molecular identifiers 132 will, in the case of T-cells, identify single cells with two different α chains and two different β chains and, moreover, will be able to determine which α chain is paired with which β chain. And in such instances, the single cell sequencing that includes unique molecular identifiers 132 will, in the case of B-cells, identify single cells with two different heavy chains and two different light chains and moreover, will be able to determine which heaving chain is paired with which light chain.

The number of possible clonotypes in a given clonotype dataset 122 can be quite large. Accordingly, referring to FIG. 7, filters 326 and 328 can be used to filter list 304. Moreover, scroll bar 308 can be used to traverse list 304. For instance, filter 326 permits one to filter by gene name (e.g., individual V or J gene name), specific CDR3 nucleotide sequence, barcode 130, contig identifier 128, or specific CDR3 amino acid sequence.

Figure 7:
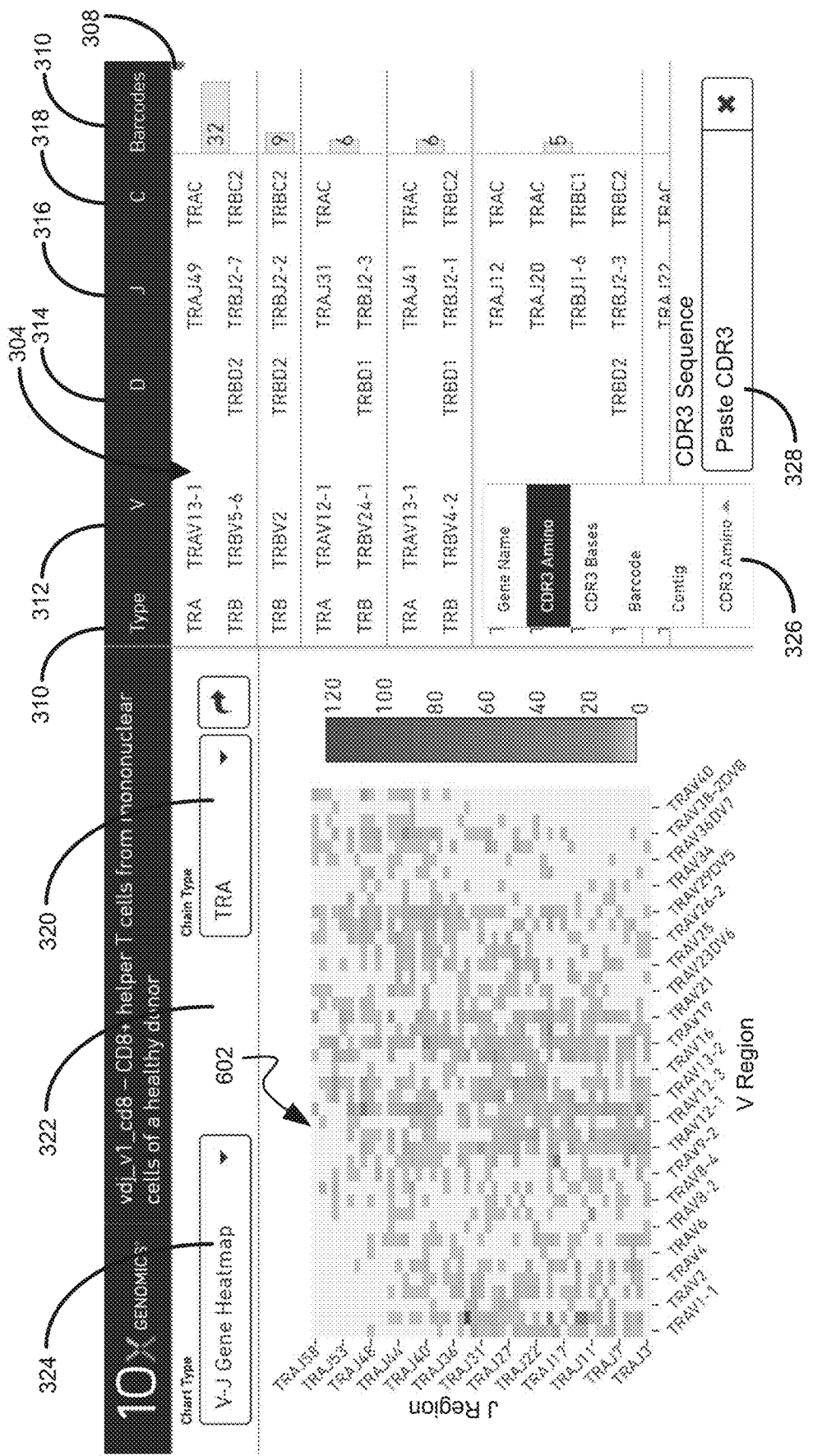
FIG. 7 illustrates an example display for entering search criteria for filtering a dataset in accordance with some embodiments.

FIG. 7 further illustrates how affordance 320 has been set so that heat map 602 now illustrates the matched V/J genes in the CDR3 region of a particular lymphocyte chain type (e.g., T-cell receptor α chains). Filters 326 operate on any of the graph types of the present disclosure, such as those illustrated in FIGS. 3 through 7.

In FIG. 7, filter 326 has been set to "CDR3 Amino." In this instance, filter 328 is dynamically adjusted to accept an amino acid sequence. The contigs that contain a consensus sequence 126 having an amino acid sequence that matches the amino acid sequence query of filter 328 are provided in the list 304. The amino acid sequence specified in filter 328 can be short (e.g., less than five amino acids) which will result in more hits than when the amino acid sequence specified in filter 328 is long. Moreover, wild cards (meaning any amino acid or no amino acid whatsoever at a given position) can be specified within the sequence in the search query of filter 328. As such, some embodiments of the present disclosure provide one or more affordances 326/328 on the display that are configured to receive a user specified selection criterion. Responsive to receiving the user specified selection criterion, the listing 304 is limited to those clonotypes in the plurality of clonotypes of the dataset that match the selection criterion. As illustrated in FIG. 7, in some embodiment the selection criterion is a contig, a barcode, an amino acid sequence, or a nucleic acid sequence. Further responsive to receiving the user specified selection criterion, the two-dimensional visualization is also limited to consideration of only those clonotypes in the plurality of clonotypes that match the selection criterion.

Figure 8:
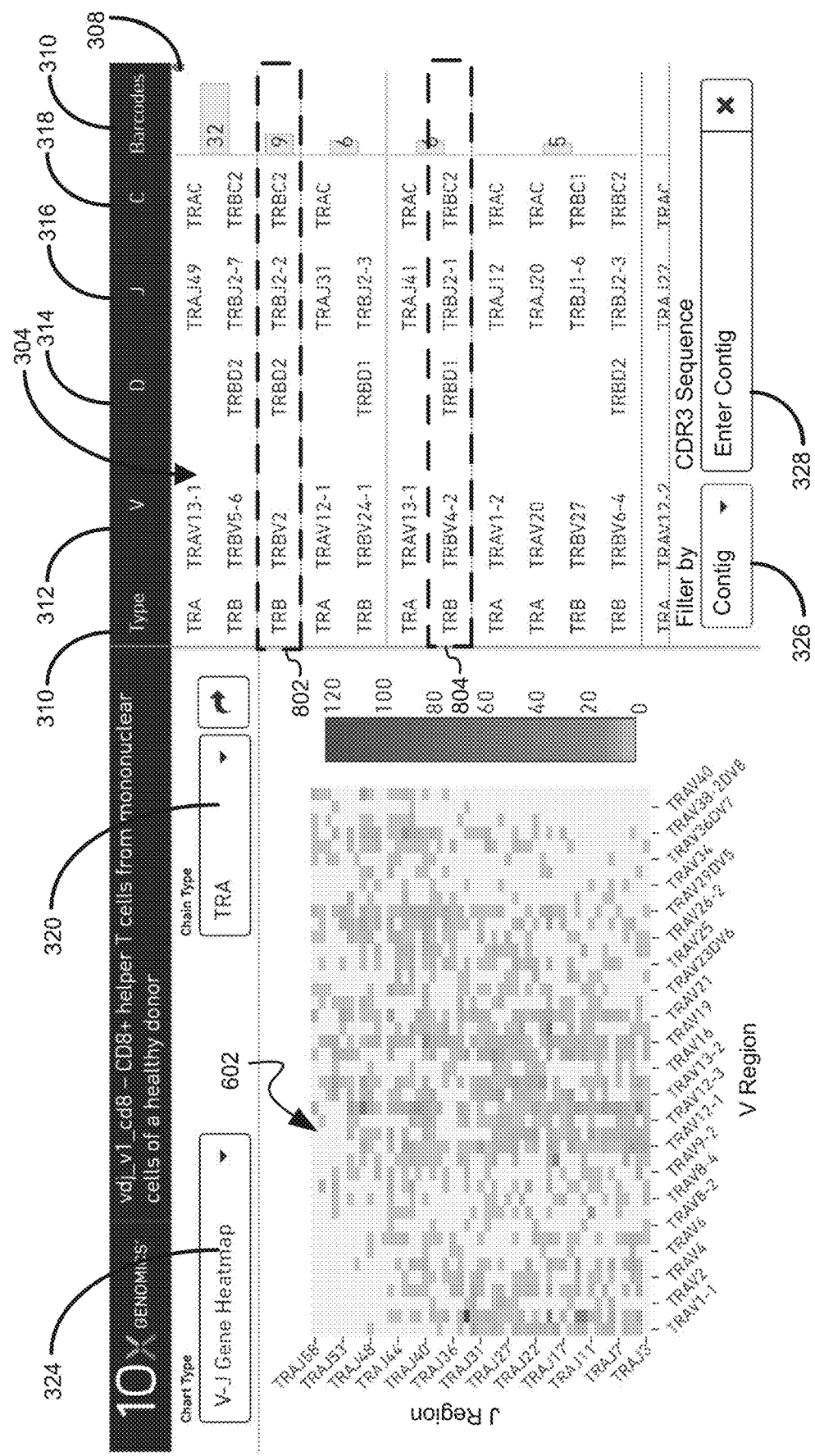
FIG. 8 illustrates an example display for entering search criteria for filtering a dataset in accordance with some embodiments.

Turning to FIG. 8, filter 326 has been set to "contig." In this instance, filter 328 is dynamically adjusted to accept one or more contig identifiers 128. When one contig identifier is entered at filter 328, the contig that matches this contig identifier is provided in the list 304. When multiple contig identifiers are entered at filter 328, any contigs that match one of the entered multiple contig identifiers is provided in the list 304

Figure 9:
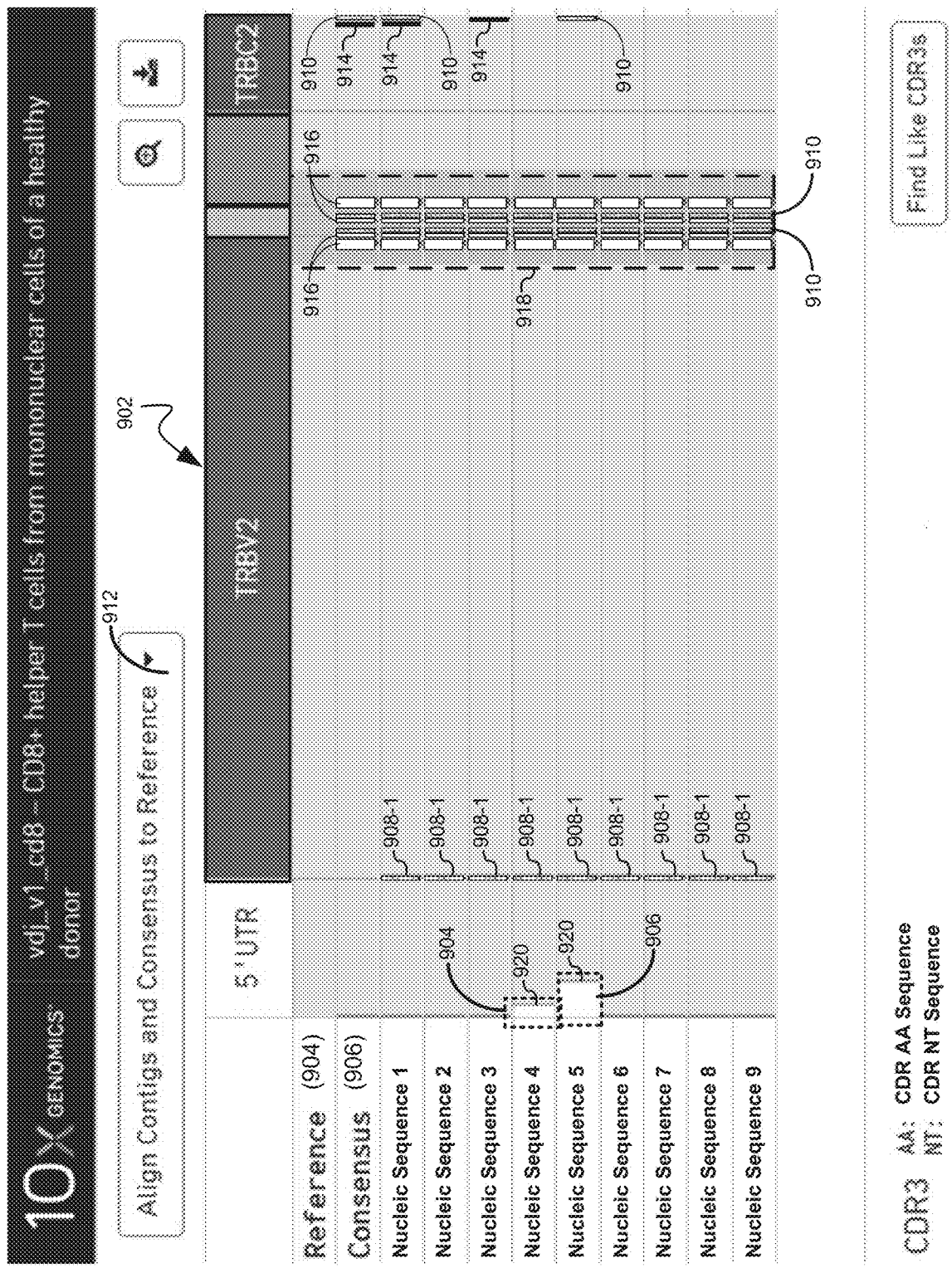
FIG. 9 illustrates the alignment of contig consensus sequences to thereby form a chain consensus sequence for a selected chain of a selected clonotype in accordance with some embodiments.

Turning to FIG. 9, advantageously, when affordance 326 is set to "gene name," affordance 328 dynamically changes to permitting the second of one or more genes that are represented in the V and J regions of the contigs of the clonotype dataset 122. When a single gene is inputted, any contig that contains the gene is displayed in the list 304 and the corresponding left hand graph. In some embodiments, selection of a gene in this manner does not update the filters on the left hand graph.

In some embodiments, when two genes are inputted, only those contigs in the clonotype dataset that contain both of the selected genes are displayed in list 304 and the corresponding left hand graph. In some embodiments, selection of two genes in this manner does not update the filters on the left hand graph.

In some embodiments, when three genes are inputted, only those contigs in the clonotype dataset that contain all three of the selected genes are displayed in list 304 and the corresponding left hand graph. In some embodiments, selection of three genes in this manner does not update the filters on the left hand graph.

In some embodiments, when four genes are inputted, only those contigs in the clonotype dataset that contain all four of the selected genes are displayed in list 304 and the corresponding left hand graph. In some embodiments, selection of four genes in this manner does not update the filters on the left hand graph.

Continuing with FIG. 9, in alternative embodiments, when affordance 326 is set to "gene name," affordance 328 still dynamically changes to permitting the second of one or more genes that are represented in the V and J regions of the contigs of the clonotype dataset 122. However, in these alternative embodiments, when a single gene is selected, any instance of that gene in the contigs displayed in the list 304 is highlighted and the corresponding left hand chart is not affected by this selection. When two genes are selected, any instance of either of those two genes in any of the contigs in the list 304 is highlighted and the corresponding left hand graph is not affected. When three genes are selected, any instance of any of the three genes in any of the contigs in the list 304 is highlighted and the corresponding left hand graph is not affected. When four genes are selected, any instance of any of the four genes in any of the contigs in the list 304 is highlighted and the corresponding left hand graph is not affected. Referring to FIG. 8, in the case where the clonotype dataset 122 comprises T-cells, each row in list 304 refers to the VDJ region of a single T-cell receptor chain (e.g., α chain, β chain, etc.). In the case where the clonotype dataset 122 comprises B-cells each row in list 304 refers to the VDJ region of a single B-cell immunoglobulin chain (e.g., heavy chain, light chain, etc.). A user may select any of the single chains listed in Table 304 (e.g. by using a mouse to click on the row representing a single chain). When this happens, the summary chart in the left hand of the screen is replaced with summary information for the selected chain but list 314 remains. For example, referring to the β chain 802 in table 304 of FIG. 8, when a user clicks on the row representing β chain 802, the heat map 802 is replaced with panel 902 of FIG. 9. Although FIG. 9 does not include list 304, in preferred embodiments of the VDJ browser 120 panel 902 is displayed along with list 304 so that the user can select another chain. In some embodiments, a user can return to the summary charts illustrated in FIGS. 3 through 8 and provided by affordance 324 by pressing a predetermined affordance (not shown) or a designated keyboard sequence (e.g., Ctrl-Home). As such, referring to FIG. 8, some embodiments of the present disclosure provide a listing 304 that includes a plurality of rows. Each respective row (e.g., 802/804) in the plurality of rows specifies the indication of a chain type of a contig in the plurality of contigs for a clonotype in the plurality of clonotypes. Responsive to user selection of a row in the plurality of rows, the display of the two-dimensional visualization (e.g., chart 602 of FIGS. 6-8, chart 302 of FIGS. 3-4, chart 502 of FIG. 5) is replace with summary information (e.g., summary information 902 of FIG. 9) for the chain represented by the selected row, while maintaining the display of the listing.

Turning to FIG. 9, more details for the VDJ region of the selected chain 802 are provided in panel 902. That is, panel 902 provides the details of a single chain in a single clonotype in a table format. The top row 904 of the table is a reference sequence which is what all the rows below are aligned to. The reference sequence is the published curated sequence of the genes identified in the selected chain 802 of FIG. 8. The second row 906 of the table is the chain consensus sequence from all the contigs 128 that support the selected chain 802 of the selected clonotype (e.g., a consensus of all the contig consensus sequences that support the selected chain 802 of the selected clonotype). As detailed in FIG. 9, there are nine barcodes 130, and thus 9 contigs 128, that support this single chain. Accordingly, the table of panel 902 of FIG. 9 lists all nine contigs. Thus, each row below row 906 is for a separate contig that supports the chain consensus sequence of row 906. In some embodiments, the reads 136 in the clonotype dataset are obtained from sequencing and are de novo assembled into contigs by barcode. See Zheng, 2017, "Massively parallel digital transcriptional profiling of single cells," Nature Communications, DOI: 10.1038/ncomms14049, which is hereby incorporated by reference. Each of the contigs that are successfully matched to the selected chain of the selected clonotype are listed as a row in panel 902. The grey shaded areas on each row indicates where the contig covers the chain consensus sequence. In some instances, not all the contigs have contig consensus sequences 126 that support the entire chain consensus sequence. For instance, the contig consensus sequence 126 for the contig represented by barcode CTCGAAAAGCGATCCC-1 does not have a sequence for region 904 and so this area is whited out in the row for this contig in panel 902. Further, the chain contig consensus sequence 126 for the contig represented by barcode CTGTGCTCAACCGCCA-1 does not have a sequence for region 906 and so this area is whited out in the row for this contig in panel 902. While these are examples of 5' absence, the contigs may also have 3' absence in their contig consensus sequences and, in such instances, these absences are indicated by the whited out areas. As such, there can be whited areas to left or the right in the contig consensus sequence of each contig. If the whited out area occurs in the chain consensus sequence row 906, this means that that there were no reads assembled for that area in any of the contig consensus sequences that are aligned to form the chain consensus sequence. In some embodiments, indicators are used to signify particular features. For instance, the boxes 908 represent start codons. Boxes 910 represent nucleic acid sequence mismatches with the target alignment sequence, which in the case of FIG. 9 is the reference sequence 904 as indicated by affordance 912. Boxes 914 represent insertions relative to the target alignment sequence. Boxes 916 represent deletions relative to the target alignment sequence. Although not shown in FIG. 9, stop codons are also shown in a similar manner. Although these representations are shown with different types of shaded boxes in the embodiment illustrated in FIG. 9, in other embodiments each type of event, start codon, mismatch, insertion, and deletions, is highlighted in a unique color representative of the event. For instance, in some embodiments, start codons are represented by green bars, stop codons are represented by red bars, and so forth. As such in some embodiments, a representation of a respective contig in panel 902 includes one or more indicators, wherein the one or more indicators includes a start codon of the respective contig, a mismatch between the respective contig and the consensus sequence, a deletion incurred in the respective contig with respect to the consensus sequence, a stop codon of the respective contig, or a coding region of the respective contig.

It will be noted that each of the contigs have the same sequence in the region denoted by box 918 because this region defines the single clonotype which was used to select the contigs represented in panel 902. However, the contigs can have differences outside of box 918 in some clonotype datasets 122. In other clonotype datasets, where the cells are essentially the same, for instance a clonal expansion from a single cell, where one cell has been expanded into hundreds of cells, there is not expected to be any differences in the V regions and the J regions of each of the contigs. Advantageously, panel 902 of the VDJ browser allows a user to quickly ascertain if this is the case.

It will be appreciated that there will be bars, such as bars 920 at the ends of the reads that are also mismatches. These bars represent artifacts of analysis because the 5' end of sequence reads tend to vary, so mismatches are expected at those points, but that is outside the region that is of concern. The protein coding region starts after box 908 for each contig and goes to the right. As such, panel 902 provides a graphical representation that validates that a clonal expansion, represented by clonotype dataset 122 was successful in the embodiment of the VDJ browser 120 illustrated by FIG. 9. In other words, panel 902 provides a visual basis for identifying the support for the consensus sequence 126 of a chain of a clonotype. In still other words, how much confidence there is for the consensus is provided. The consensus sequence 906 (126 of FIG. 1) is assembled from every contig 128 for the selected chain of the selected clonotype.

The region of the consensus spanning box 918 is about 12 amino acids long in some embodiments and defines the clonotype. However, panel 902 shows more of the VDJ region of the chain to assist users in analyzing the VDJ genes. For instance, some users seek to synthesize the VDJ region. Such users need to know the entire coding sequence which is the entire V and the entire J sequence. The CDR3 region denoted by box 918 is the clonotype, but that is not the only important sequence, regions 5' and 3' are needed in many use cases to establish fidelity.

Figure 10:
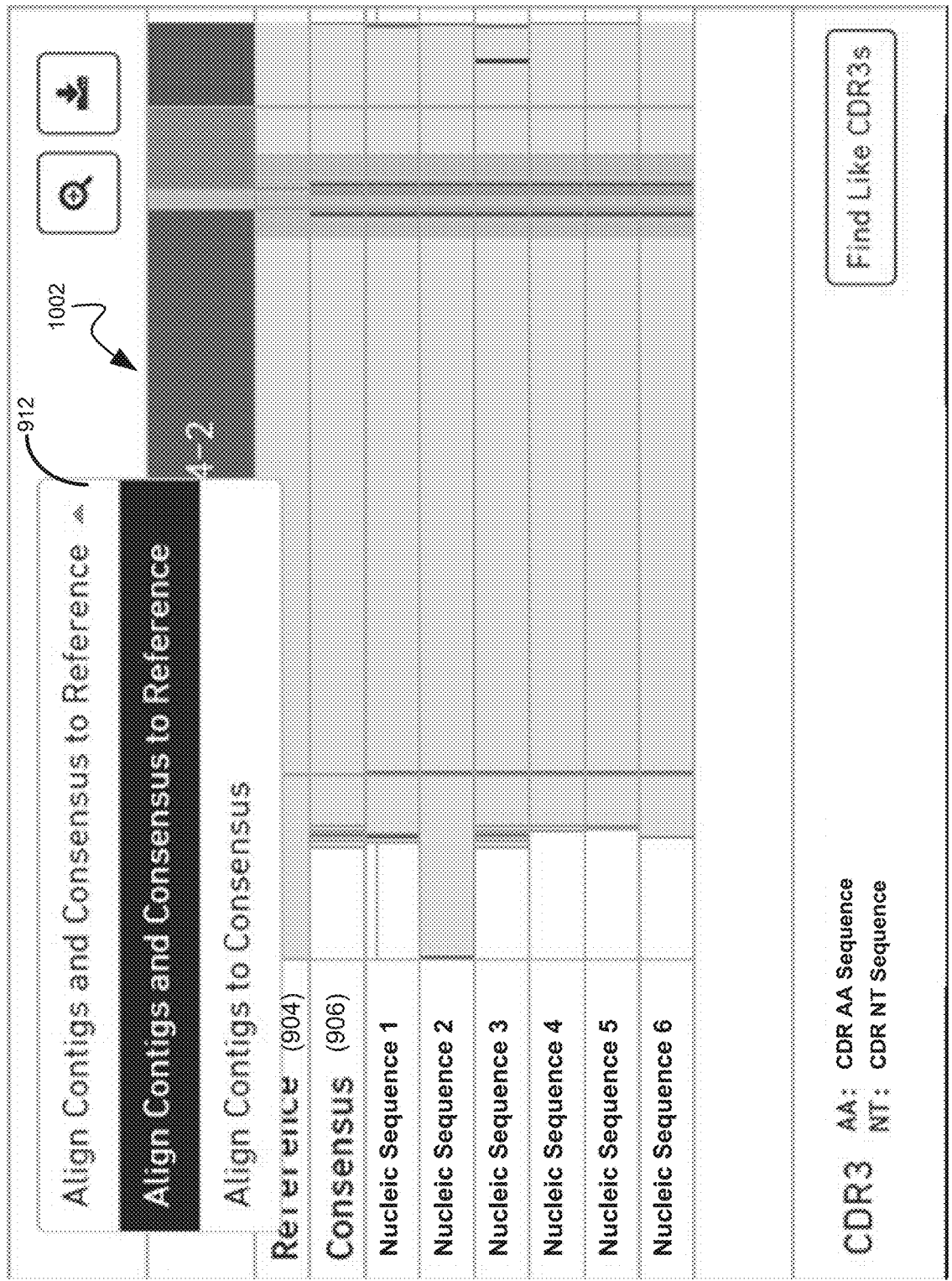
FIG. 10 illustrates the alignment of contig consensus sequences to either a reference sequence or a chain consensus sequence for a selected chain of a selected clonotype in accordance with some embodiments.

FIG. 10 illustrates the selection of the T-cell β chain 804 from list 304. As indicated in column 310 of list 304 on FIG. 8, there are six barcodes 130 that support this clonotype. Accordingly, six contigs are listed below the chain consensus line of the table in panel 1002 of FIG. 10. Moreover, affordance 912 can be used to align the contig consensus sequence of each of these contigs and the chain consensus sequence to a reference sequence, or, alternatively, to align the contig consensus sequence of each of these contigs to the chain consensus sequence.

Figure 11:
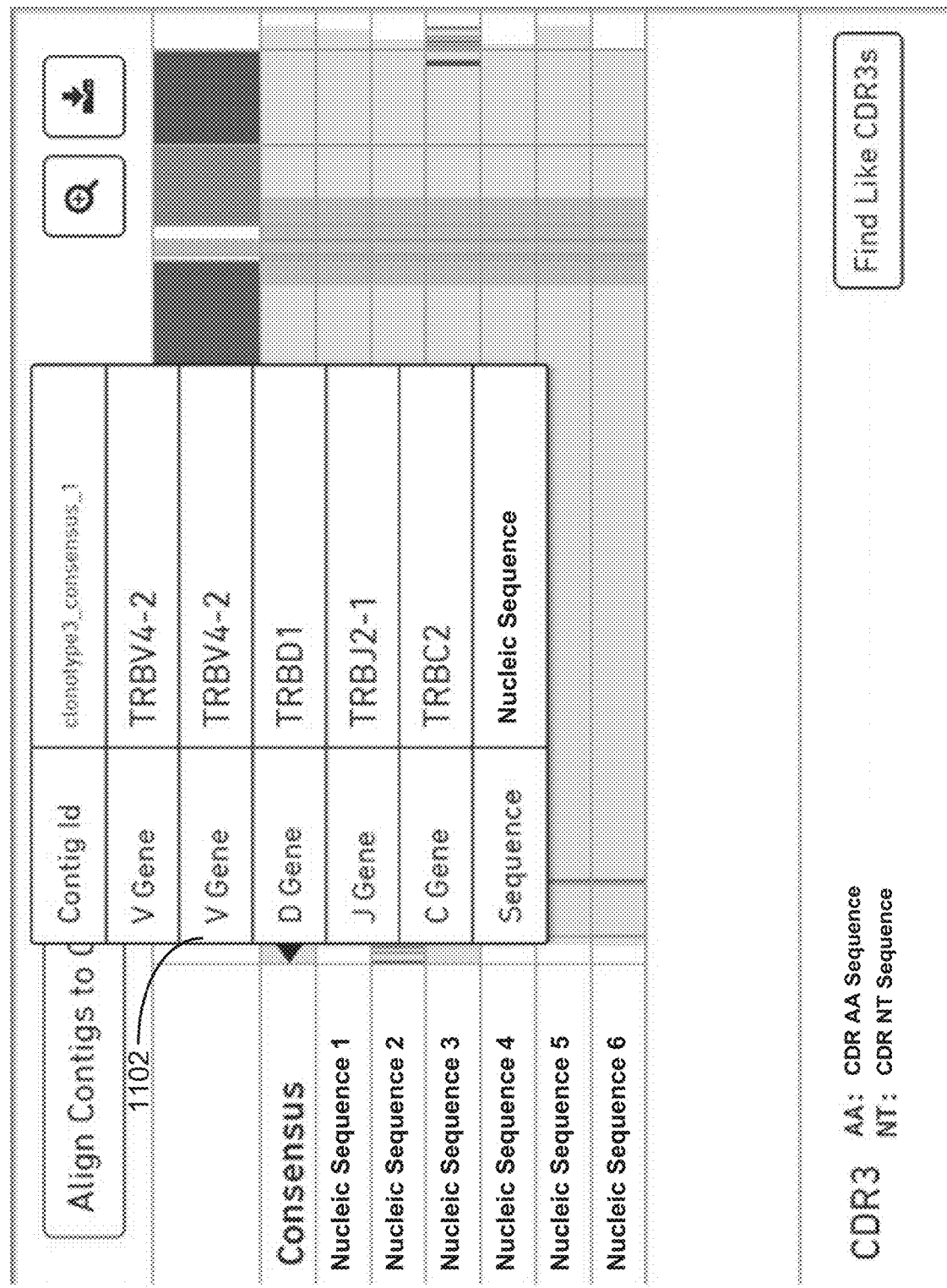
FIG. 11 illustrates the display of additional information regarding a chain consensus sequence for a selected chain of a selected clonotype in accordance with some embodiments.

FIG. 11 illustrates how a user can easily obtain the entire chain consensus sequence of the V, D, J, and C gene sequences that form the chain consensus sequence 906 of FIG. 10 by simply clicking on the chain consensus sequence row 906 of panel 1002 of FIG. 10. When this is done, panel 1102 of FIG. 11 is displayed by the VDJ browser 120. Panel 1102 provides the identity of the V, D, J and C genes of the selected chain, and provides the chain consensus sequence, which can then be copied and pasted into another application. In some embodiments the chain consensus sequence can be exported to file. This is useful for users that wish to synthesize the region de novo. This feature is advantageous because the region is in the range of 700 bases long. Thus, in some embodiments, responsive to selection of the consensus sequence, the entire consensus sequence is displayed in a format that is configured for user cutting and pasting into separate application running on the system.

Figure 12:
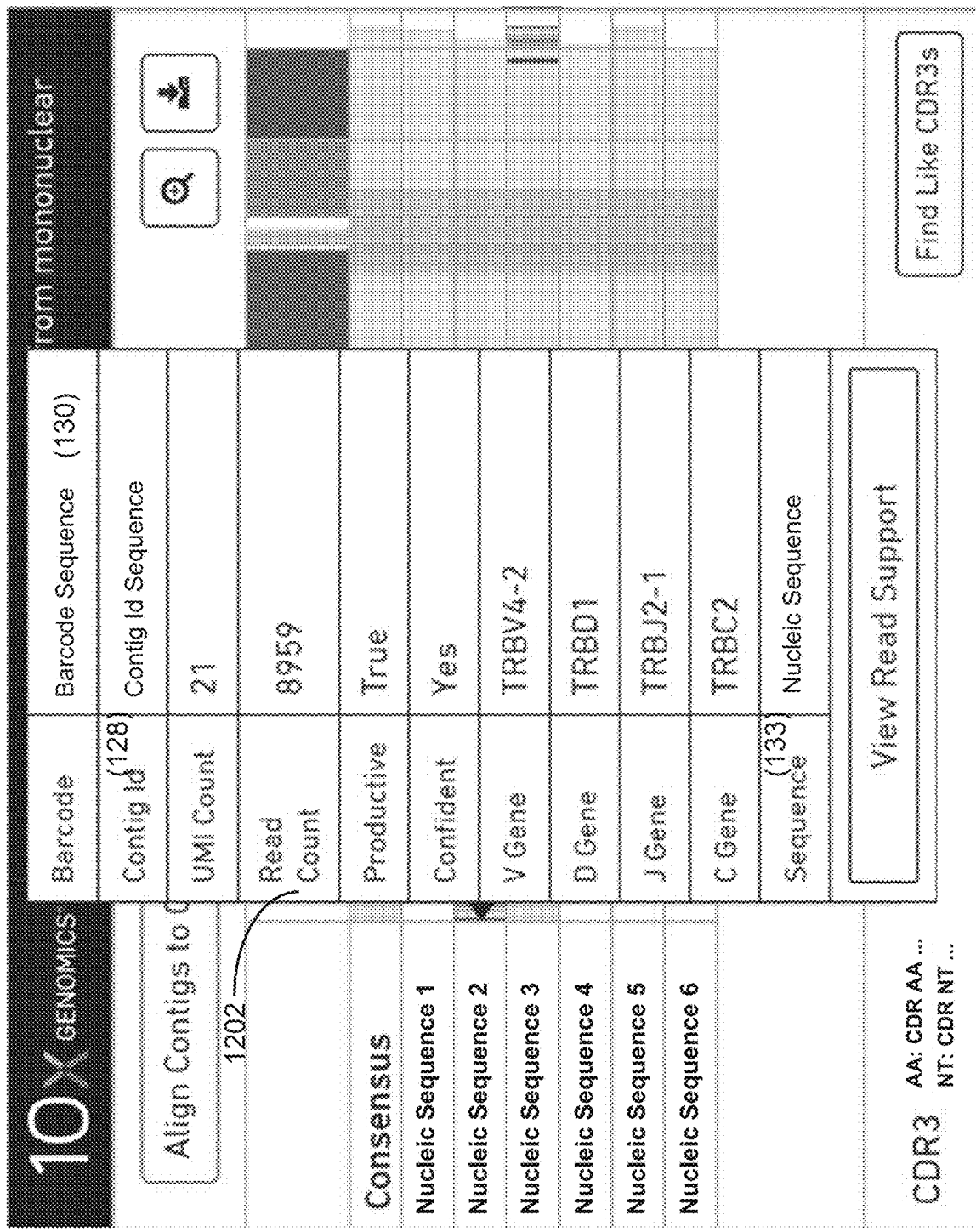
FIG. 12 illustrates the display of additional information regarding a contig consensus sequence for a selected contig of a selected chain of a selected clonotype in accordance with some embodiments.

FIG. 12 illustrates how a user can readily obtain additional information about one of the contigs that support the consensus sequence. In FIG. 12, the user has clicked on the row for the contig represented by barcode 130 ACATGGTAGTGACATA-1, thereby bringing up panel 1202. Panel 1202 provides information about the contig such as the associated barcode 130 for the contig, the contig identifier 128 for the contig, the number of unique molecular identifiers 132 supporting the contig (UMI count), the number of sequence reads 132 supporting the contig (read count), the reference identity of the V, D, J, and C genes for the contig, and the V, D, J, and C gene sequences that form the contig consensus sequence 126 across the sequence reads 134 that support the contig. In some embodiments the contig consensus sequence 126 can be exported to file.

Figure 13:
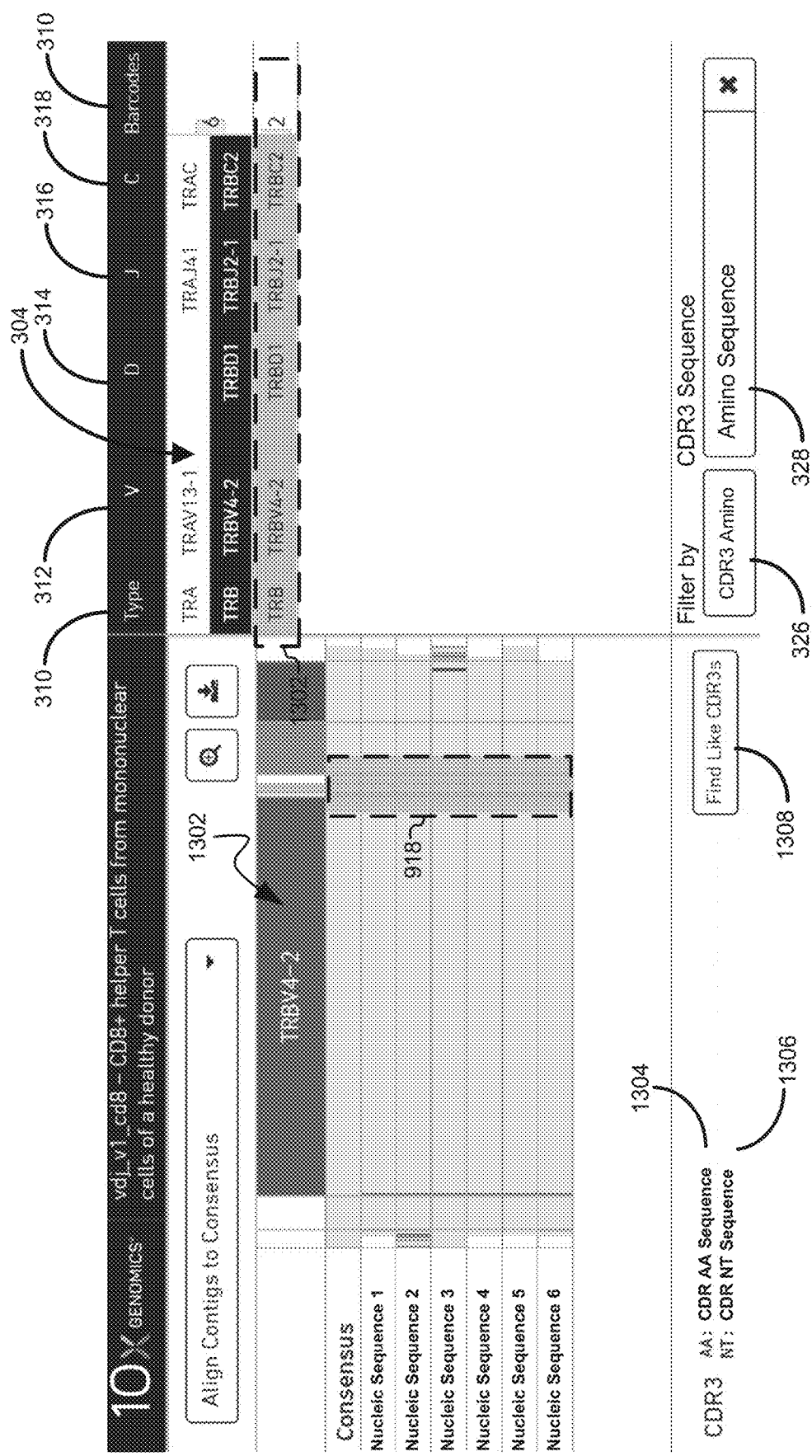
FIG. 13 illustrates user entry, using an affordance, to select a particular CDR3 amino acid sequence thereby obtaining or highlighting contigs that contain the entered CDR3 amino acid sequence in accordance with some embodiments.

Referring to FIG. 13, a user has used affordance 326 to select entering a particular CDR3 amino acid sequence, the sequence of which is entered into affordance 328, thereby obtaining contigs in list 304 that contain this amino acid sequence using VDJ browser 120. In FIG. 13, the user has selected a particular lymphocyte receptor chain type (in the case of FIG. 13 the T-cell β chain) of a particular clonotype represented by row 1302 and so graph 1302 shows summary information for the selected chain of the selected clonotype. The CDR3 region of the chain is again represented by box 918, which in some embodiments of VDJ browser 120 is highlighted by having a darker background. Moreover, the amino acid sequence of region 918 is provided at position 1304 and the nucleotide region is provided at position 1306. By selecting 1304 or 1306, the respective sequence can be selected, copied, and exported to another application or saved to external memory. By pressing affordance 1308, the CDR3 sequence of the selected chain is pasted into affordance 328 without further human intervention so that the user can search for other clonotypes in the clonotype dataset that have the exact same CDR3. So if the user clicks affordance 1308, the VDJ browser copies the sequence at position 1304 and pastes it into affordance 328. In this way the user can see all the other chains of the same type that have the exact same CDR3. These other chains will not necessarily be of the same clonotype as the chain depicted in panel 1302. For instance, they may be paired with different chains in the corresponding lymphocyte receptor. That is to say, a clonotype is defined by not just the individual CDR3s, but the pairs of CDR3s among the cells (e.g., in the case of T-cells, the CDR3 from the α chain and the CDR3 from the β chain). For instance, the example clonotype dataset depicted in the instant figures includes the clonotype for 349 cells. In each one of those 349 cells, there has been expressed that particular T-cell receptor chain. That α receptor chain, or the gene sequence for that alpha receptor chain and the gene sequence for the β receptor chain. Whereas the sequence for the β receptor chain, that same sequence for the β receptor chain is in other clonotypes, but paired with different β receptor chains or different α receptor chains. Clonotypes are analogously defined for B-cell immunoglobulins based upon their heavy and light chains. So a clonotype is defined by the collection of chains expressed by the same set of cells.

Figure 14:
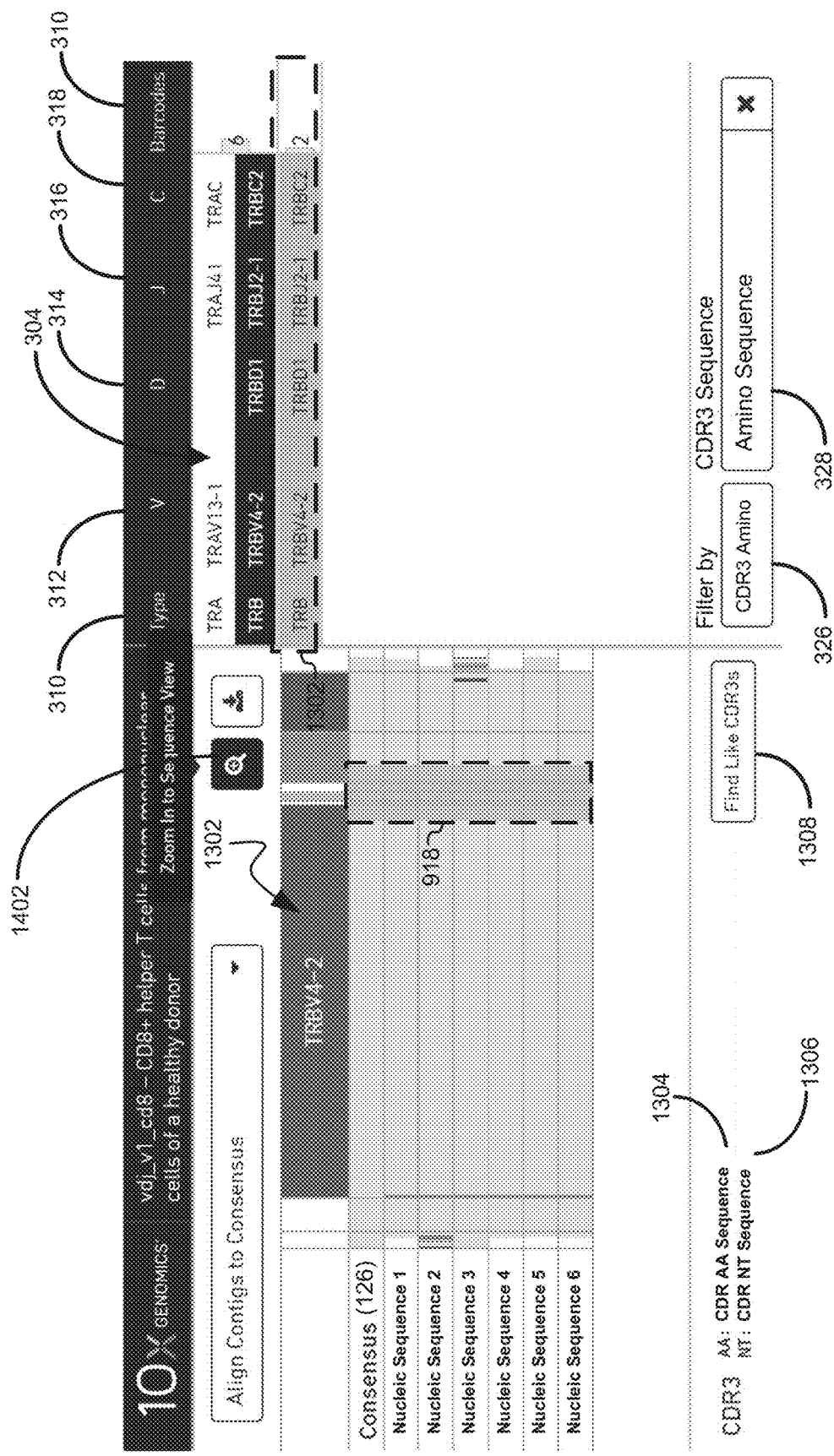
FIG. 14 illustrates how, by selection of an affordance, a user may switch to a nucleic acid sequence view in which contig consensus sequences of each contig supporting a selected chain of a selected clonotype are displayed together with a chain consensus sequence for the chain after selection of the affordance in accordance with some embodiments.
Figure 15:
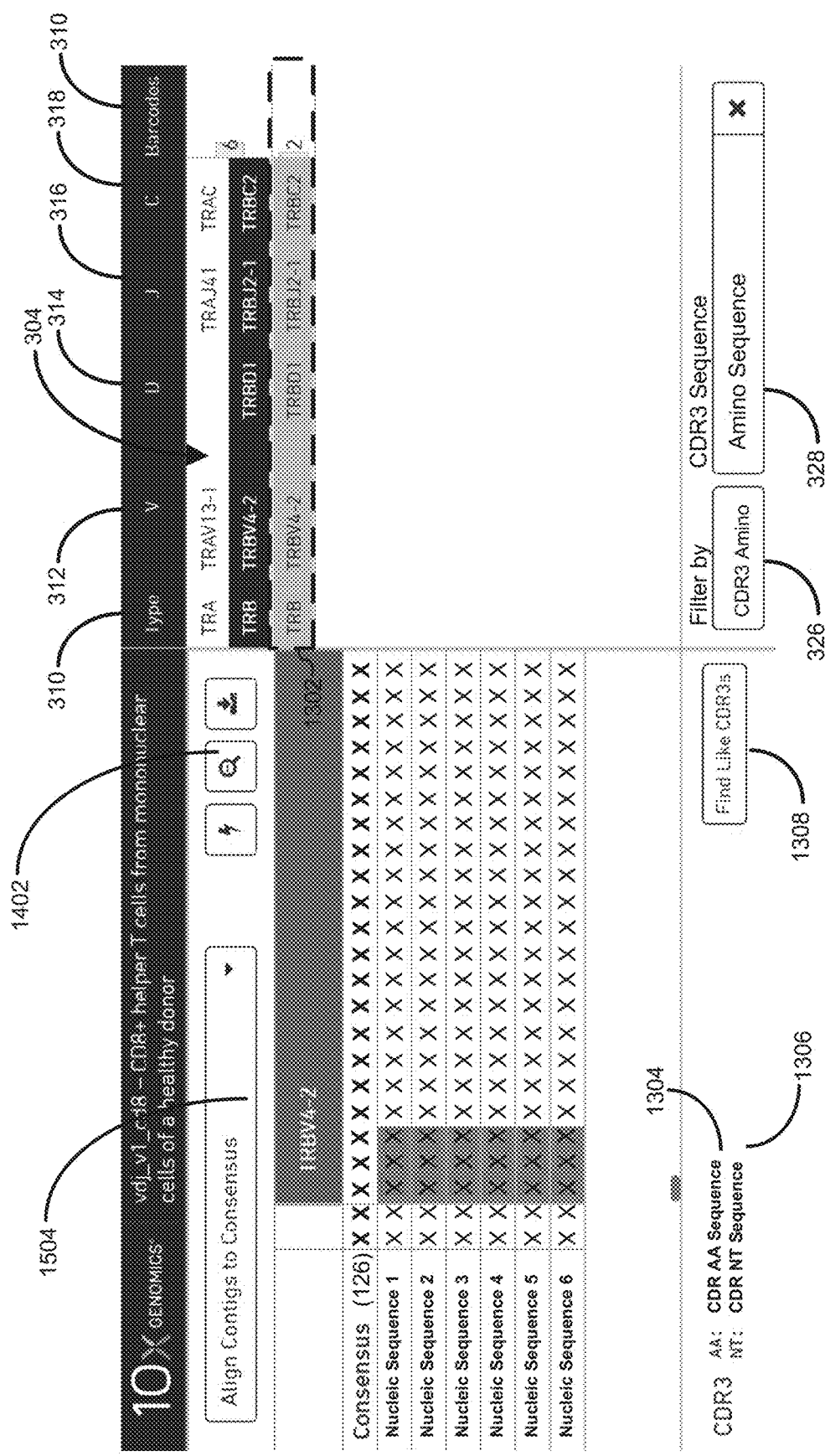
FIG. 15 illustrates the contig consensus sequences for each of the six contigs supporting a selected chain of a selected clonotype below a consensus sequence for the chain, where the consensus sequence for the chain is formed from the six contig consensus sequences in accordance with some embodiments.

Continuing to FIG. 14, by selection of affordance 1402, a user may switch to sequence view in which the contig consensus sequence 126 of each contig supporting the selected chain of the selected clonotype is displayed together with the chain consensus sequence for the chain as illustrated in FIG. 15 after selection of affordance 1402. Turning to FIG. 15, the contig consensus sequence 126 for each of the six contigs supporting the selected chain of the selected clonotype is displayed below the chain consensus sequence that is formed, in this case, from the six contig consensus sequences 126. As such, some embodiments of the present disclosure include a toggle (e.g., affordance 1402) and user selection of the toggle switches the representation of each respective contig in the dataset that includes the selected chain type from one of (i) a graphical representation of each respective contig (e.g., as in FIG. 14) and (ii) a sequence (e.g., as in FIG. 15) of each respective contig, to the other of (i) the graphical representation of each respective contig and (ii) the sequence of each respective contig.

Referring to FIG. 15, affordance 1504 indicates that the contigs are aligned to the chain consensus sequence. However, affordance 1504 also permits the user to align the contigs to the reference sequence for the selected chain of the selected clonotype. In some embodiments, the reference annotation is the Ensembl annotation for the genes encompassed by the chain being analyzed by the VDJ browser. See, Aken et al., 2015, "The Ensembl gene annotation system Database," baw093, doi: 10.1093/database/baw093; and McLaren, 2016, et al., "The Ensembl Variant Effect Predictor," Genome Biology 17, p. 122, doi: 10.1186/s13059-016-0974-4 each of which is hereby incorporated by reference. When the Ensemble reference is used for alignment, the VDJ browser 120 displays the contigs aligned to the known reference sequence instead of the chain consensus sequence that was generated from the contigs. Moreover, the chain consensus sequence is also aligned to reference, and only the regions that are included in the reference are aligned. That is, all the outside, 5' and 3' regions are cut off, so only the annotated regions provided, for example from Ensembl annotation, are displayed.

Accordingly, in some embodiments, the VDJ chain reference sequence table is all the human V, D, J and C regions that are found in the human genome in accordance with the Ensembl gene annotation system database and the reference sequences that best match the selected chain of the selected clonotype serve as the reference sequence when affordance 1504 is set to align contigs to reference sequence. That is, the reference sequence is the concatenation of the canonical assembly of the individual V, D, J, and C genes from the Ensembl gene annotation system database that best match the contigs of the selected chain of the selected clonotype. FIG. 9 illustrates this situation. What is observed in FIG. 9 is that the consensus sequence 126 (displayed as 906 in FIG. 9), which is derived from the contigs, the actual observations, all have a modification, denoted by boxes 910 and 916, with respect to the human genome reference 904. However, because these modifications are consistent across the contig consensus sequence 126 of each of the contigs for the chain consensus sequence, it is apparent that this modification represents a real mutation that is in all of the particular cells supporting the consensus sequence (displayed as 906 in FIG. 9) and that the chain of the clonotype being analyzed in the left hand portion of FIG. 9 is in fact different from the human genome reference 904, but is consistent with the chain consensus sequence 906 that has been called based on the observation of all the contigs.

In some embodiments, the VDJ chain reference sequence table is all the V, D, J and C regions that are found in a mammalian genome. In some embodiments, the VDJ chain reference sequence table is all the V, D, J, and C regions that are found in a non-human animal. Examples of the animal include, but are limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark.

Accordingly, FIGS. 1 through 15 illustrate how the VDJ browser provides an efficient mechanism for analyzing clonotype data, for instance by providing the chain consensus sequences for any of chains in any of the clonotypes present in a clonotype dataset. The VDJ browser advantageously provides a visual verification on one side of the display of the browser as well as tabulated information on the other side of the display of the browser. Moreover, the VDJ browser allows users to perform classic immunological tasks more efficiently, such (i) as plotting out the frequencies of clonotypes in a given clonotype dataset 122, (ii) observing the VDJ region for the most abundant clonotype in a given clonotype dataset 122 and determining how abundant the clonotype is in another dataset, (iii) obtaining an overall assessment of the clonotype data, and (iv) deriving a sense of confidence that the clonotypes that were computed for the clonotype dataset 122 (e.g., by upstream applications) are rooted in the actual regions that were sequenced. The graphics, as illustrated in FIGS. 2 through 15 provide this information to a user in a quick efficient manner in a way that cannot be done as easily or efficiently, or reliably if it were done without a computer.

Figure 16:
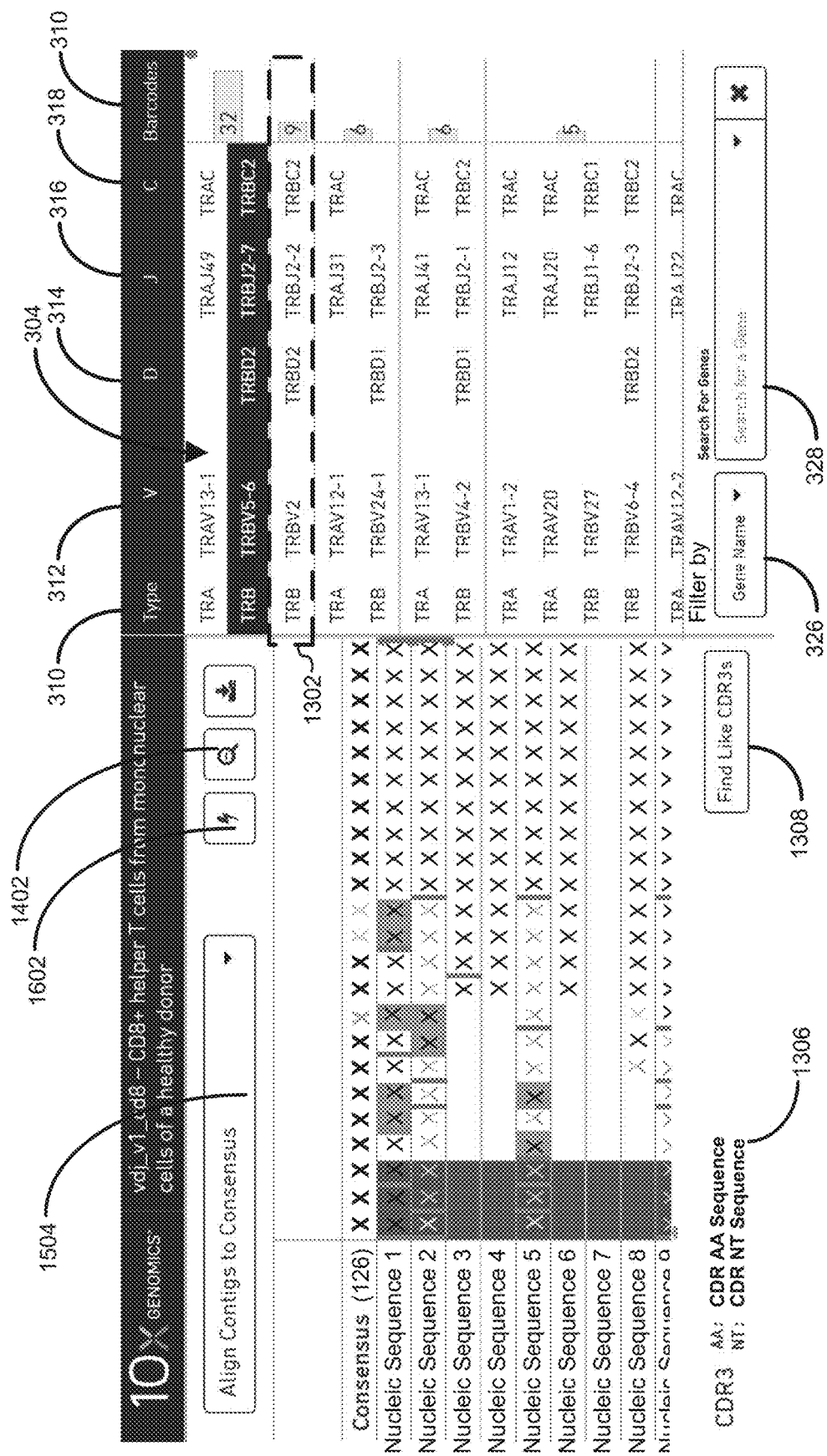
FIG. 16 illustrates selection of an affordance to render the contig consensus sequences of contigs into sequence view and zooming to particular features of interest in accordance with some embodiments.
Figure 17:
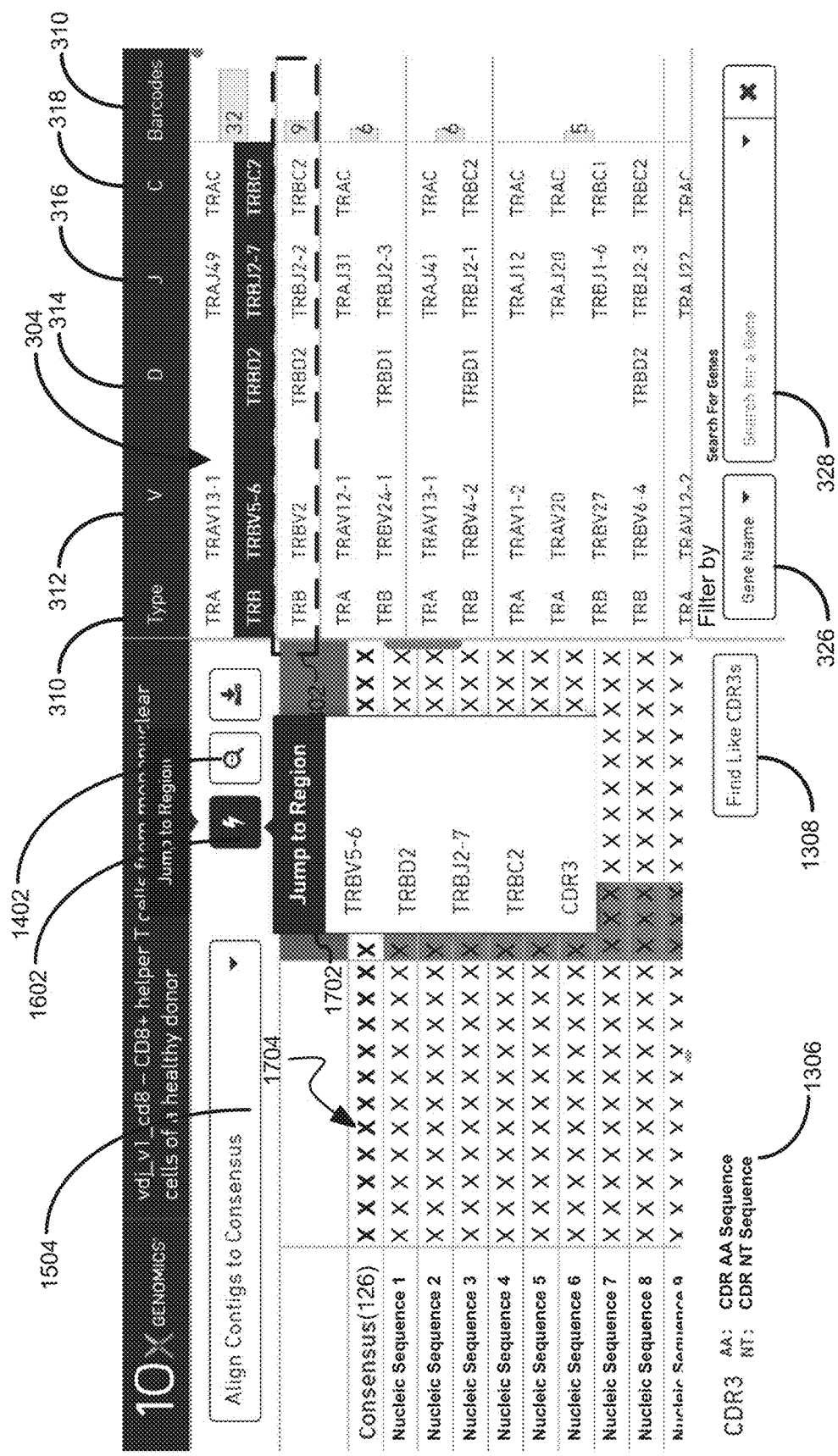
FIG. 17 illustrates selection of an affordance thereby causing the display to jump to various regions of the selected chain of the selected clonotype, such as the V, D, J, C, or CDR3 portions of the chain in accordance with some embodiments.
Figure 18:
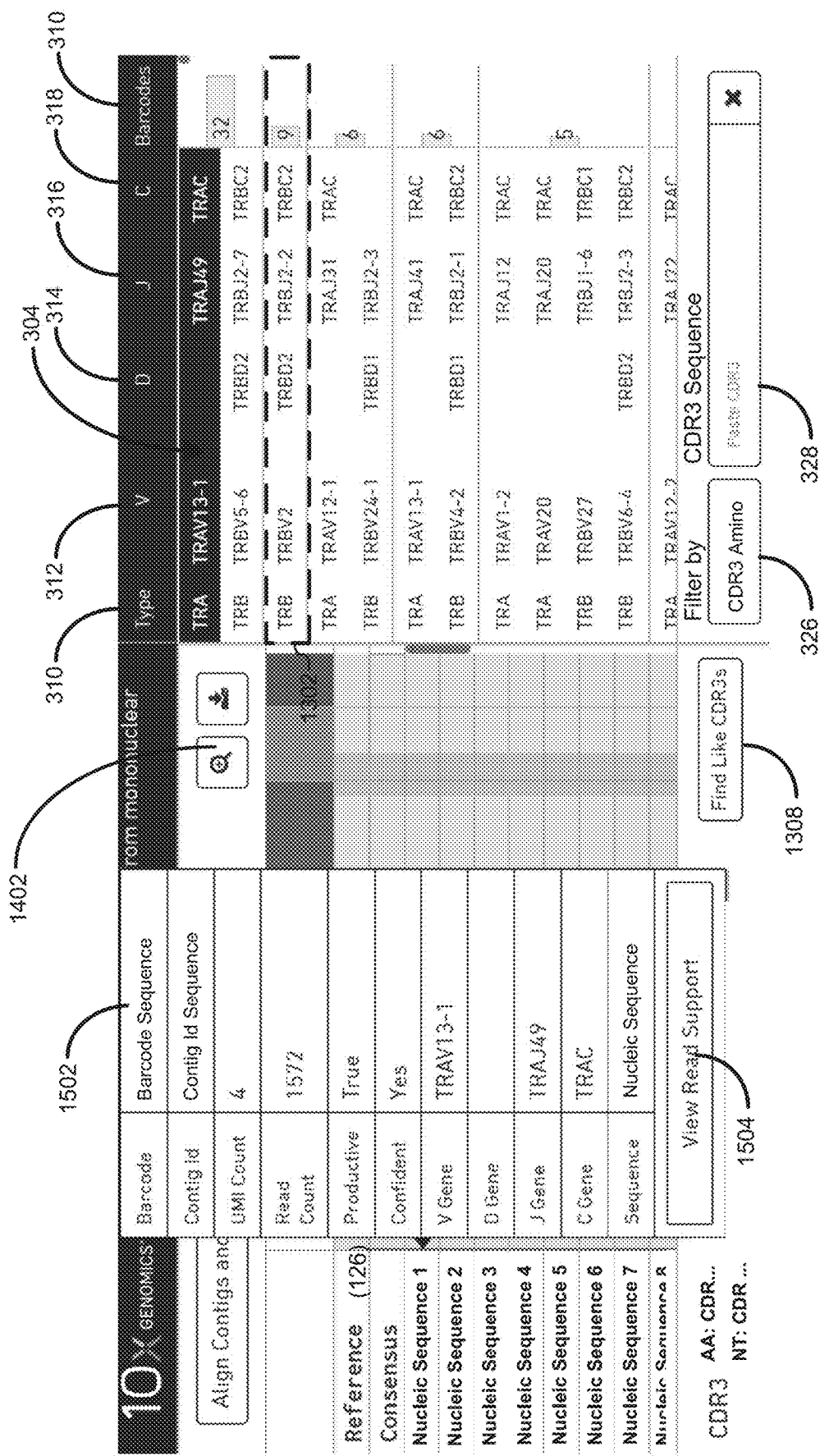
FIG. 18 illustrates how to display read support for a contig consensus sequence of a selected contig of a selected chain of a selected clonotype in accordance with some embodiments.
Figure 19:
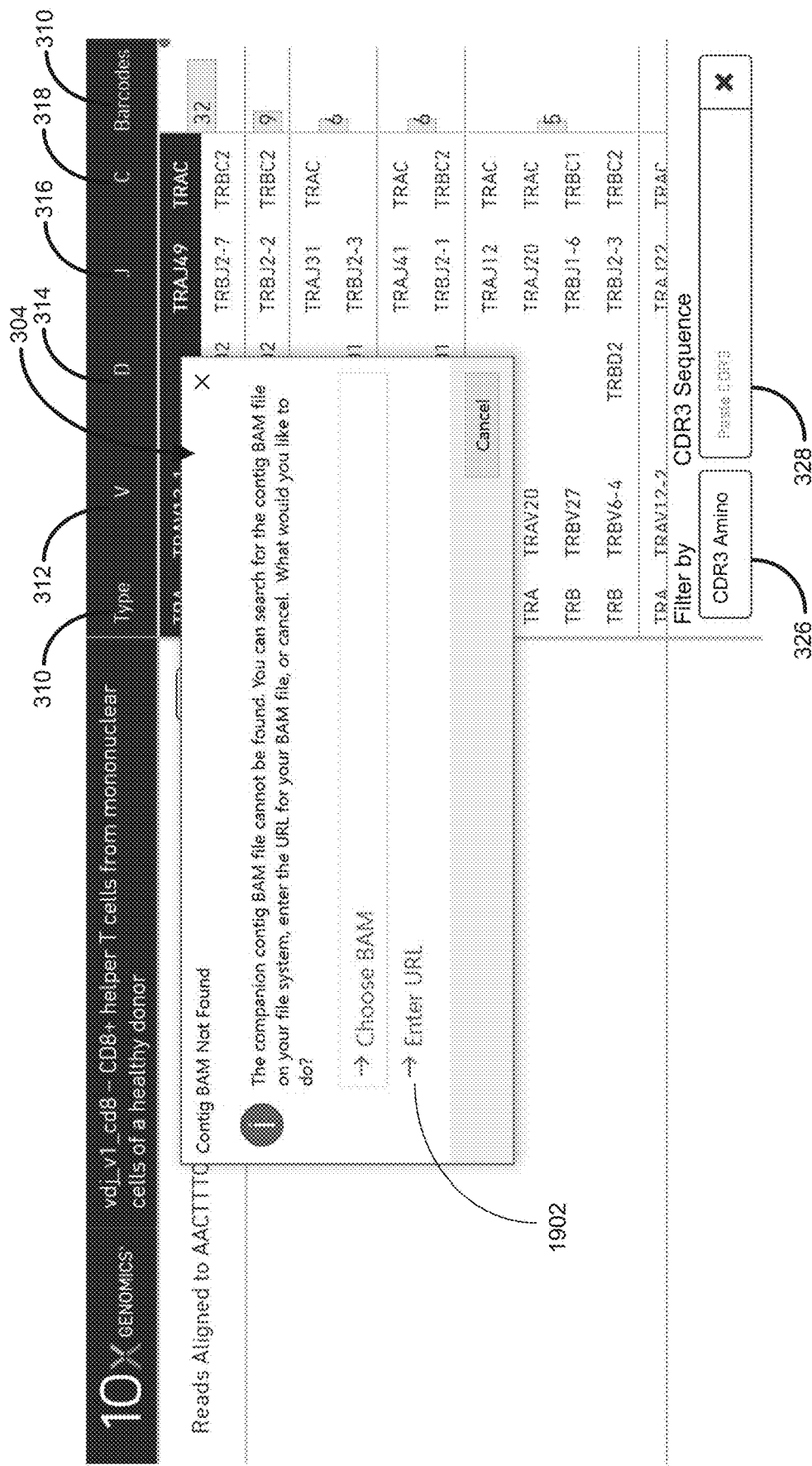
FIG. 19 illustrates how to obtain an alignment file in order to display read support for a selected contig of a selected chain of a selected clonotype in accordance with some embodiments.
Figure 20:
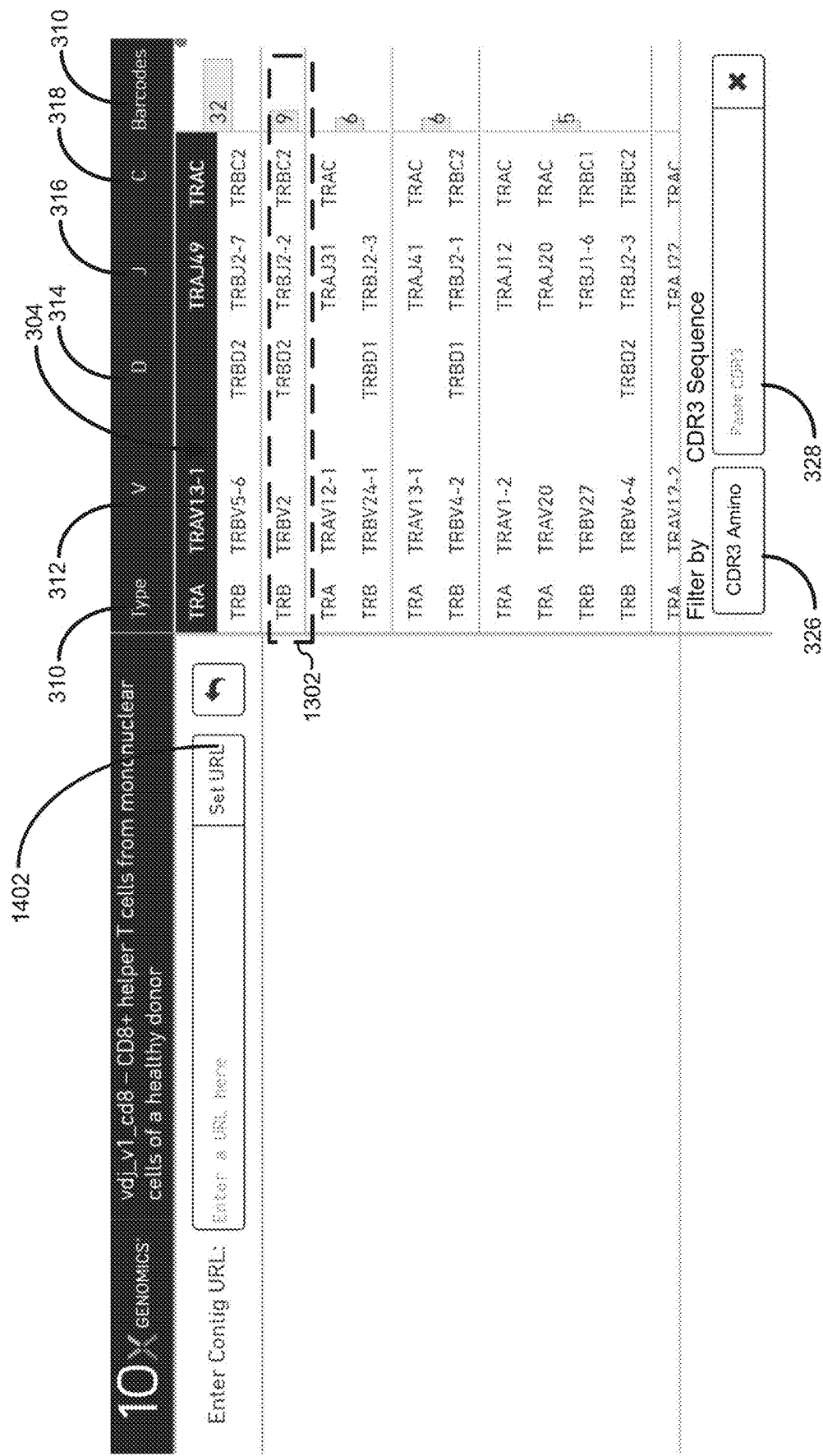
FIG. 20 illustrates how to obtain an alignment file by providing a uniform resource location of the alignment file in order to display read support for a contig consensus sequence of a selected contig of a selected chain of a selected clonotype in accordance with some embodiments.

Referring to FIG. 16, when affordance 1402 has been used to render the contigs into sequence view, affordance 1602 can be used to zoom into particular features of interest. For instance, referring to FIG. 17, by clicking on affordance 1602 the user can jump to various regions of the selected chain of the selected clonotype, such as the V, D, J, C, or CDR3 portions of the chain. When the user selects such a portion from menu 1702, the view of table 1704 zooms to the selected feature. Furthermore, referring to FIG. 9, the user can instantly transition to sequence/zoom view by selecting on a feature such as a particular feature 908, 910, or 916. When the user clicks on one of these features of FIG. 9, panel 902 is transitioned to the sequence view in the vicinity of the selected feature and the nucleic acid sequence of the region of the selected feature across all the contig consensus sequences 126 across all the contigs is displayed. Thus, for instance, if the user is interested in a deletion in FIG. 9, they can click on this feature and the VDJ browser will jump to this region in sequence view. In this way, a user can look at exactly what bases are deleted and what bases were mismatched. Moreover, any sequence displayed in some embodiments of the VDJ browser can be exported, such as in FASTA format.

Figure 21:
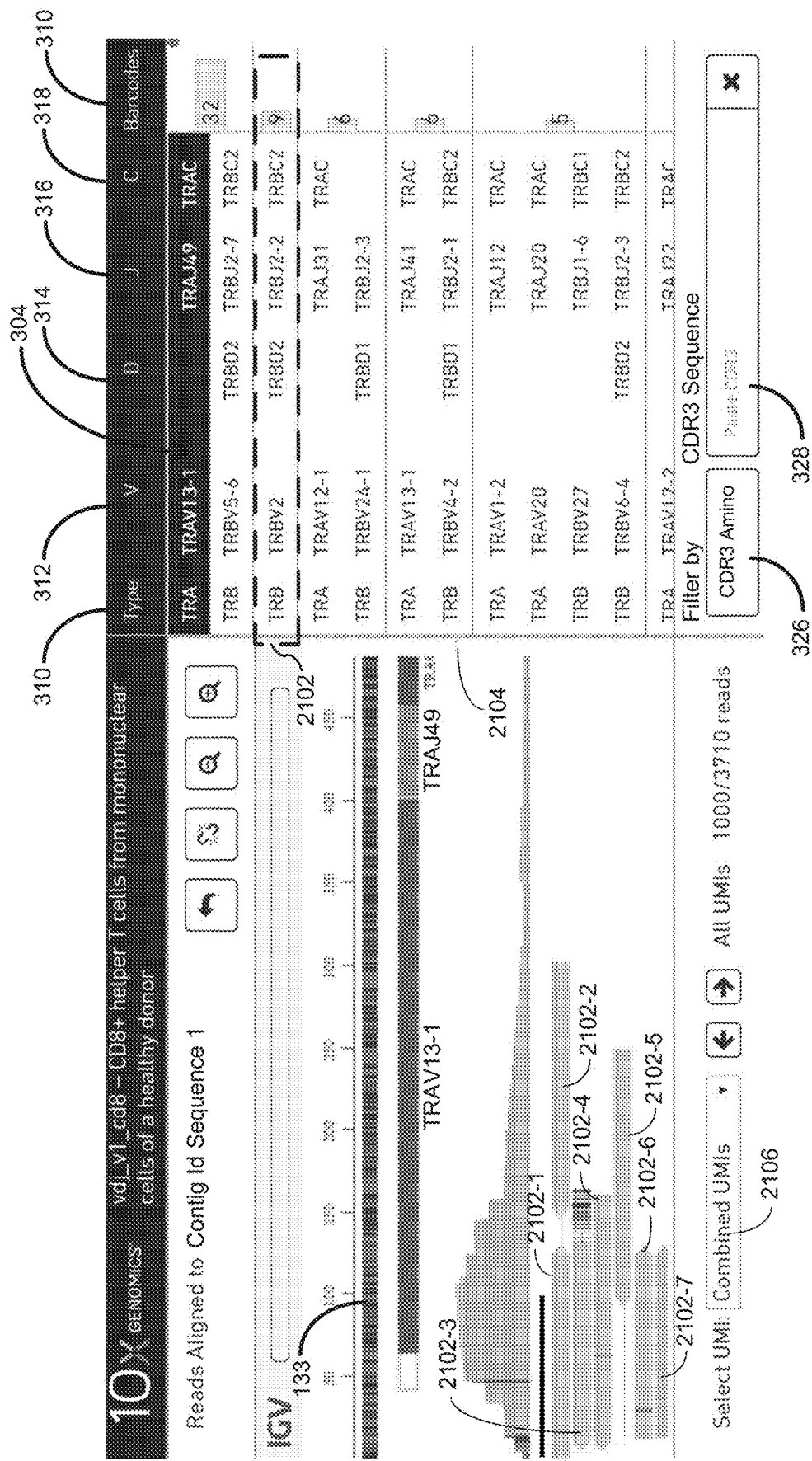
FIG. 21 illustrates read support for a contig consensus sequence of a selected contig of a selected chain of a selected clonotype, on a unique molecular identifier by unique molecular identifier basis, in accordance with some embodiments.

Turning to FIGS. 18 through 23, in some embodiments, the VDJ browser further provides sequence read 134 support view, so that a user can inspect the sequence reads 134 that correspond to each of the contigs supporting a particular chain consensus sequence for a selected chain of a selected clonotype. Thus, in FIG. 18, the user has selected the contig 128 immediately below the chain consensus sequence row bringing up panel 1802 which provides information regarding the contig as described above. One of the fields in panel 1502, field 1504 "View Read Support" allows the user to inspect the sequence reads 134 supporting the selected contig. Selection of this field 1504 brings the user to the display illustrated in FIG. 19, in some embodiments, in which the user provides the actual physical location of a data file (e.g. a BAM file) or a uniform resource location (URL) address of the file. BAM is the compressed binary version of the Sequence Alignment/Map (SAM) format, a compact and index-able representation of nucleotide sequence alignments. For instance, selection of field 1902 of FIG. 19 brings the user to the display of FIG. 20 in which the URL to a suitable alignment file (e.g., BAM file) is entered. Upon entry of the appropriate alignment file, the VDJ browser provides a graphical depiction of the alignment of each of the sequence reads 134 that are supporting a particular contig consensus sequence 126 as illustrated in FIG. 21. Thus, what FIG. 21 illustrates is all the reads that aligned to the contig 128 having the contig identifier Contig Id Sequence 1, which is one of the 9 contigs that supports the chain consensus sequence for the selected chain 2102 of table 304.

In FIG. 21, the contig consensus sequence 126 is just below a nucleotide ruler. Further illustrated is what support has been provided by the particular sequence reads 134 that were used to assemble the contig consensus sequence 126. Each line 2104 represents individual reads having the same unique molecular identifier 132 that contribute to the contig consensus sequence 126. That is, each of the reads 2104 map to the same particular molecule that was sequenced in a particular GEM. FIG. 21 shows how each of the reads 2104 align to form the contig consensus sequence 126. All the sequence reads 134 displayed in FIG. 21 (sequence reads 2102) have the prefix of the barcode Contig Id Sequence 1. Moreover, each of these sequence reads were sequenced from the same mRNA molecule. Sequencing differences, such as insertions, deletions, and mismatches are annotated into the alignment, typically with color coded annotations to represent each of these different features. Thus, any such differences in their sequences is attributable to sequencing errors. This is an advantage of using UMIs, because it confirms that such differences are sequencing errors, rather than actual features of the mRNA being sequenced. This is because each of the sequencing reads depicted in FIG. 21 are the same UMI 132, and therefore the same mRNA molecule.

Figure 22:
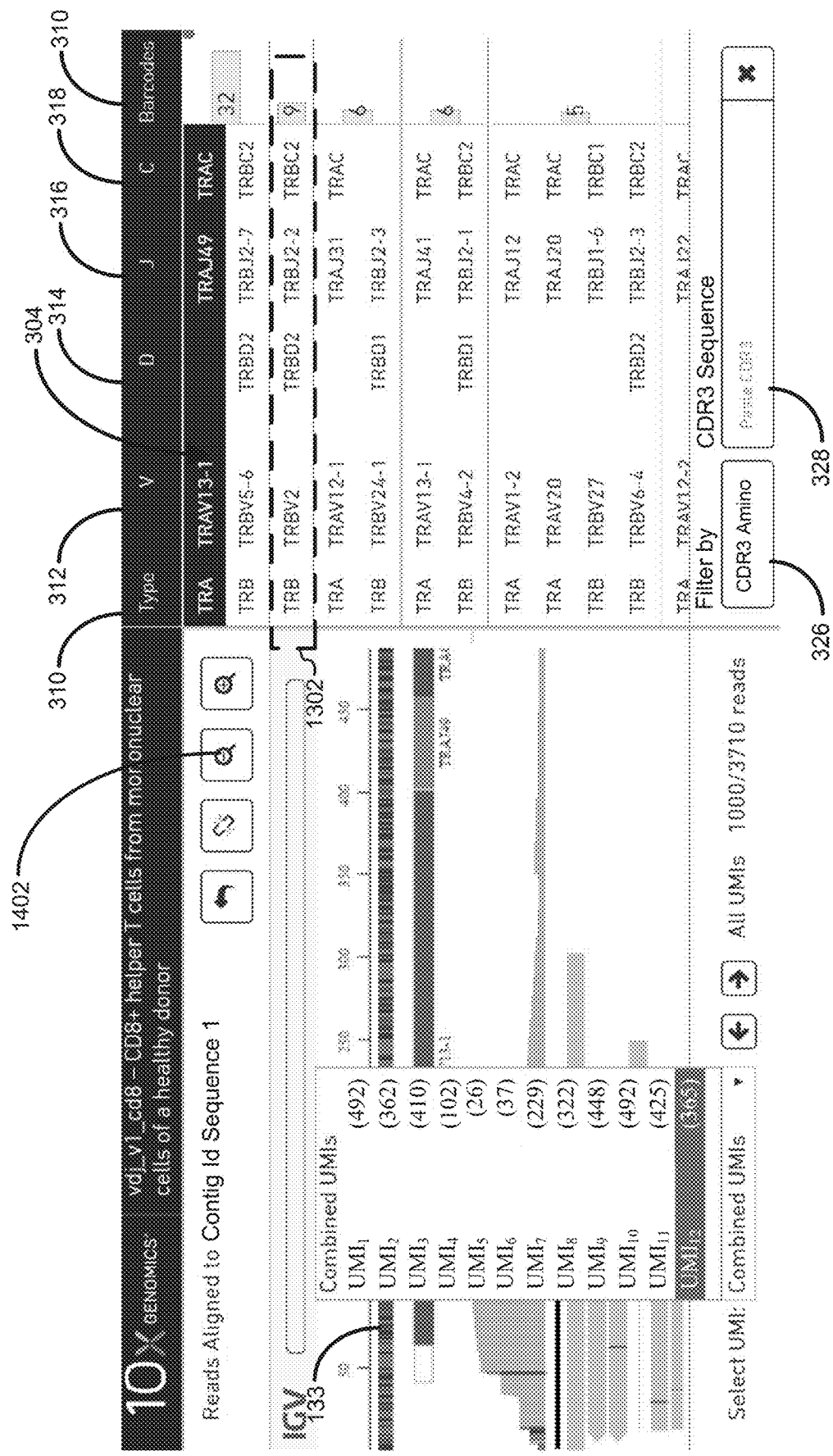
FIG. 22 further illustrates how to select read support for a contig consensus sequence of a selected contig of a selected chain of a selected clonotype, on a unique molecular identifier by unique molecular identifier basis, in accordance with some embodiments.

Moreover, there are several different UMIs that support the contig represented in FIG. 21, and the sequence reads for only one of the UMIs is visible in FIG. 21. To see the sequence read support for the other UMIs, the user can scroll down using scroll bar 2104 or select a particular UMI using affordance 2106. For example, when the user selects affordance 2106, the 12 different UMIs that are supporting the selected contig consensus sequence 126 are displayed, and the number of sequence reads that are supporting each of the UMIs, as illustrated in FIG. 22, and the user can select any of these UMIs in order to visualize a UMI consensus sequence alignment 133 of the sequence reads 134 that support the selected contig sequence 133. As such, in some embodiments of the present disclosure, a plurality of unique molecular identifiers is associated with a particular contig, and a unique molecular identifier affordance is displayed (e.g., affordance 2106 of FIG. 21) that affords choosing between (i) selection of all the unique molecular identifiers in the plurality of unique molecular identifiers and (ii) selection of a single unique molecular identifiers in the plurality of unique molecular identifiers. When the single unique molecular identifier is selected, only those sequence reads for the first contig that have the single unique molecular identifier are displayed in the alignment of each sequence read in a plurality of sequence reads to the first contig.

Figure 23:
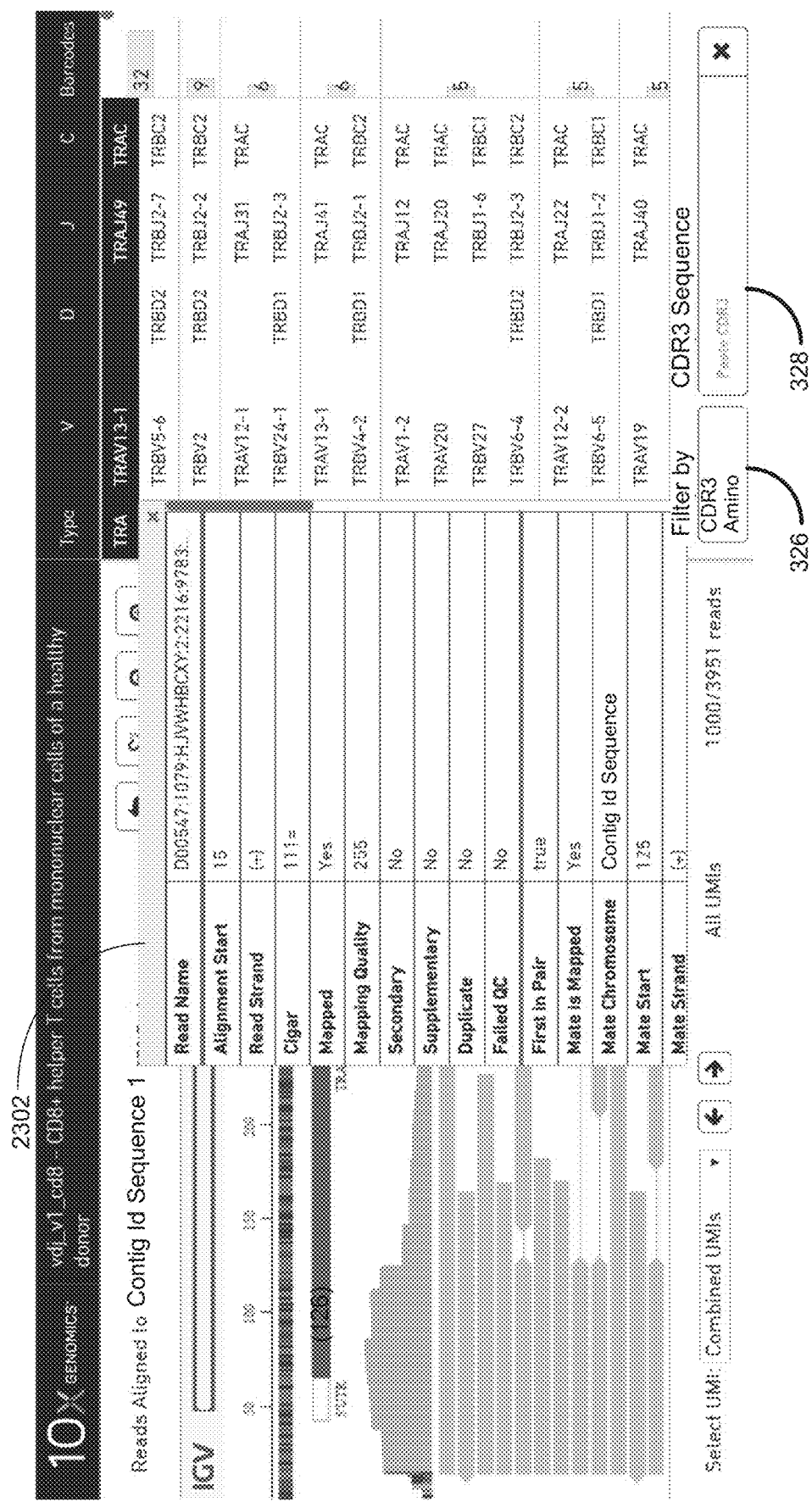
FIG. 23 illustrates how to obtain more information on a particular sequence read that supports a contig consensus sequence of a selected contig of a selected chain of a selected clonotype in accordance with some embodiments.

Referring to FIG. 23, when the user clicks on an individual sequence read 134, information about the sequence read is displayed.

In some embodiments, the VDJ browser provides counts of the number of clonotypes and number of barcodes that will update based on filtering criteria entered into fields 326 and 328.

Multi-Sample Comparison.

Figure 24:
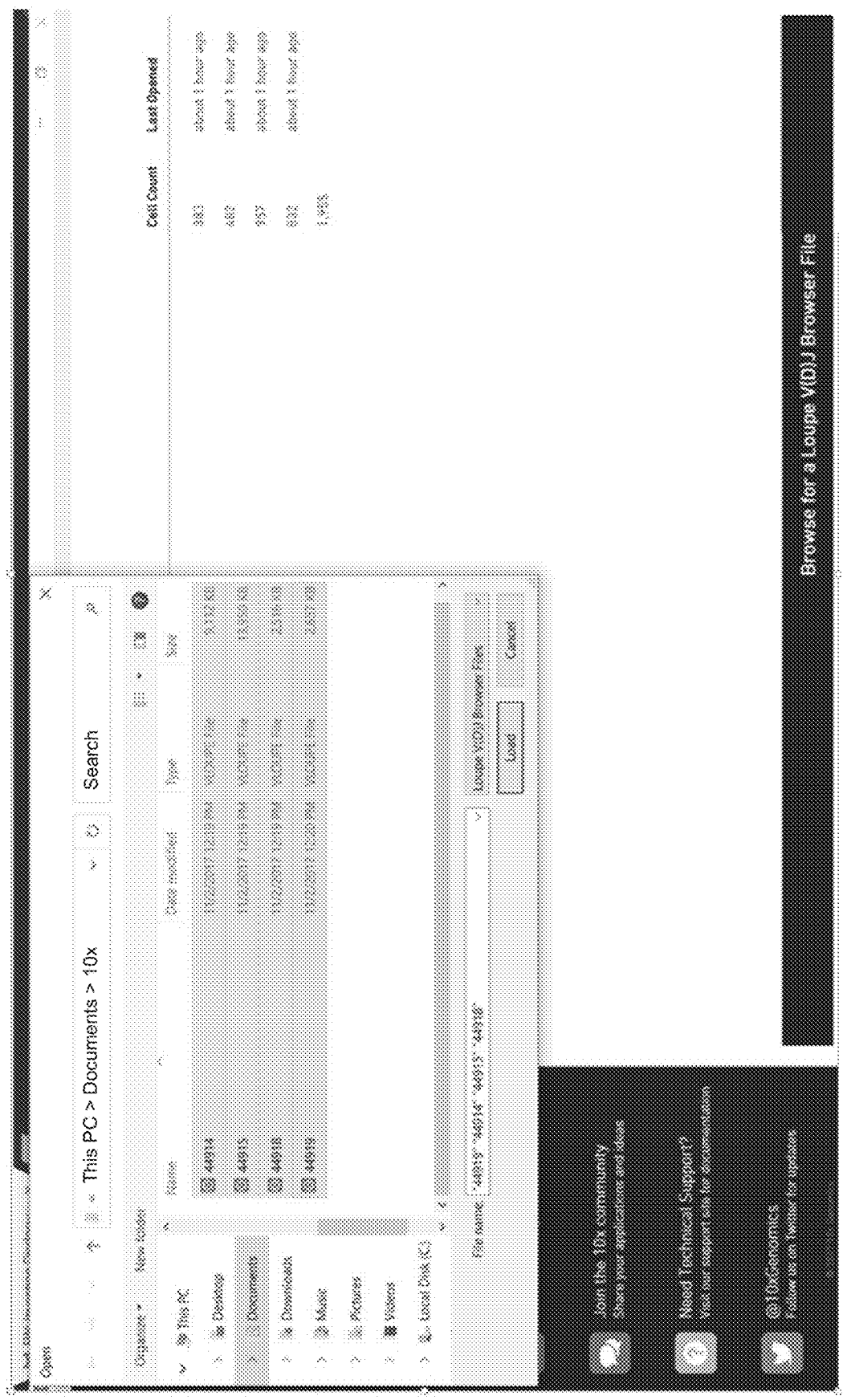
FIG. 24 illustrates how multiple clonotype datasets can be concurrently retrieved for comparative analysis in accordance with some embodiments.

Referring to FIG. 24, advantageously, in some embodiments of the present disclosure, the VDJ cell browser 120 is able to compare clonotype distributions from multiple clonotype datasets 122 and from gene expression clusters.

In FIG. 24, four clonotype datasets 122 are loaded into the VDJ cell browser 120 for concurrent analysis. Once loaded, and in accordance with the embodiment of the present disclosure illustrated in FIG. 25, the "Multi-sample Comparison" affordance 2502 is used to enable multi-sample comparison across all open clonotype datasets 122. In some embodiments, two or more, three or more, four or more, five or more, six or more, seven or more or 10 or more clonotype datasets 122, each representing a different biological sample comprising a plurality of cells, are opened by cell browser 120 for concurrent analysis.

Figure 25:
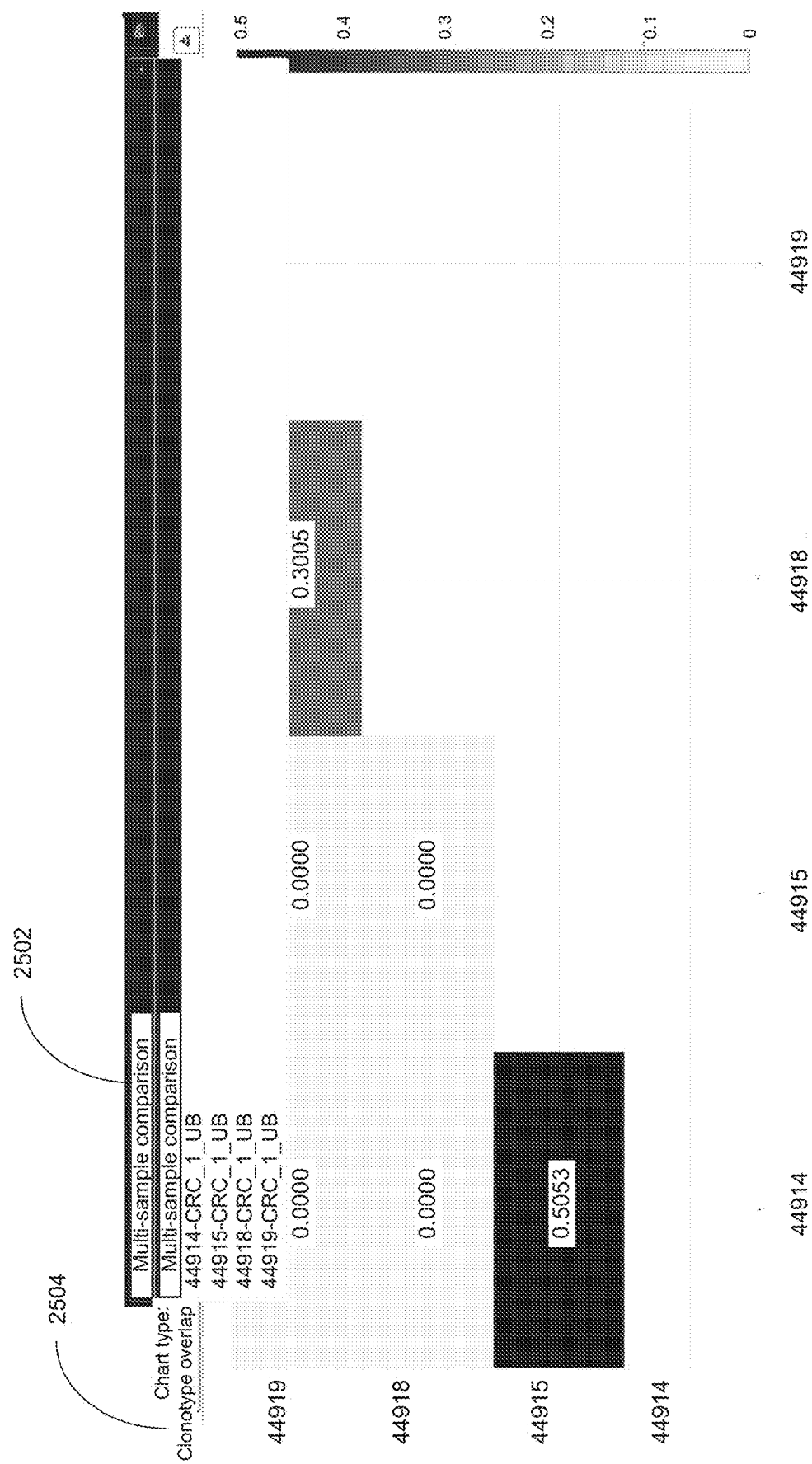
FIG. 25 illustrates how the retrieved clonotype datasets of FIG. 24 can be selected for comparative analysis in accordance with some embodiments.

In FIG. 25, affordance 2504 is used to select which comparison chart to use for the analysis of the open clonotype datasets 122. In FIG. 25, the option "clonotype overlap" is selected.

Figure 26:
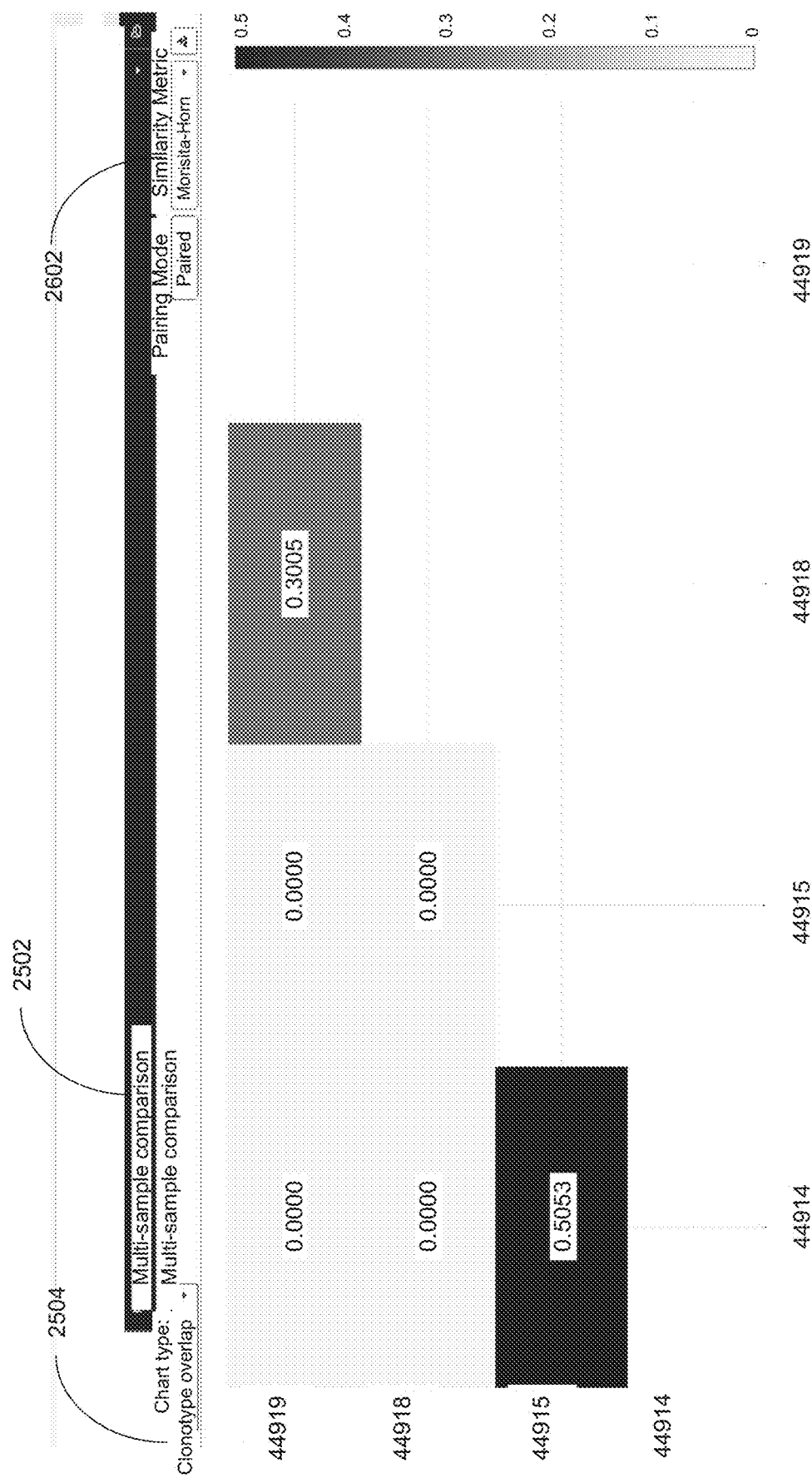
FIG. 26 illustrates the pairwise comparison of the four clonotype datasets of FIG. 25 showing the pairwise clonotype commonality between individual pairs of clonotype datasets among the four clonotype datasets using a Morisita-Horn metric in accordance with some embodiments.

FIG. 26 illustrates the pairwise comparison of the four clonotype datasets opened using the interface of FIG. 24 and the selection mechanism of FIG. 25 and with the chart type selected in FIG. 25. In FIG. 26, the pairwise clonotype commonality between individual pairs of clonotype datasets 122 among the four clonotype datasets selected in FIG. 25 is illustrated using a Morisita-Horn metric, which was selected using affordance 2602. As used in the present disclosure, the Morisita-Horn metric provides a value between 0 and 1 that weights the level of clonotype 124 overlap between the two samples that are respectively represented by two clonotype datasets 122. The Morisita-Horn metric favors paired clonotype datasets 122 that have their most frequent clonotypes 124 in common, as opposed to clonotype datasets 122 that have more overlap in the long tail distribution of clonotypes (e.g., the less frequently occurring clonotypes in the respective clonotype datasets).

Advantageously, the comparison is done at the paired-clonotype, single-cell level. That is, as noted above in conjunction with FIG. 1, each contig 128 for a given clonotype 124 represents a unique single cell. Each clonotype dataset 122 represents a different biological sample, and each clonotype 124 identified in the biological sample is associated with one or more contigs 128, each such contig representing a unique different cell within the biological sample represented by the clonotype dataset 122 (e.g., when the contig is supported by at least two unique molecular identifiers 132 that each are supported by sequence reads 134 in the data set 122). Thus, the comparison illustrated in FIG. 26 is unique and advantageous because the clonotype overlap evaluates the number of cells with a given clonotype 124 in one clonotype dataset 122 that match the clonotype of cells with the same clonotype 124 in the other clonotype dataset 122. Such a comparison is only possible when the clonotype dataset 122 indicates how many cells in the biological sample represented by the respective clonotype dataset 122 were determined to have a given clonotype 124. Thus, for each pair of clonotype datasets 122 (A, B), FIG. 26 calculates and displays a metric that shows the pairwise commonality between the two biological samples represented by the pair of clonotype datasets 122. Advantageously, because the comparison of clonotypes between the two datasets is based on single cell data, comparison metrics such as Morisita's overlap index can be used to perform the pairwise comparison of clonotype datasets 122.

Morisita's overlap index is a statistical measure of dispersion of individuals (e.g. clonotypes) in a population (e.g., in a biological sample comprising cells). It is used to compare overlap among samples. This formula is based on the assumption that increasing the size of the samples will increase the diversity because it will include different clonotypes. The Morisita formula is:

$$C_D = \frac{2\sum_{i=1}^{S} x_i y_i}{(D_x + D_y)XY}$$

where,

X is the number of cells represented by the first clonotype dataset 122 of the pairwise comparison, Y is the number of cells represented by the second clonotype dataset 122 of the pairwise comparison, $x_i$ is the number cells having clonotype i in the first clonotype dataset 122, $y_i$ is the number of cells having clonotype i in the second clonotype dataset 122, $D_x$ and $D_y$ are the Simpson's index values for the x and y clonotype datasets 122 respectively, and S is the number of unique clonotypes 124 across the two clonotype datasets 122 being compared.

Here, CD=0 if the two clonotype datasets 122 do not overlap in terms of clonotypes 124, and CD=1 if the clonotypes 124 occur in the same proportions of cells in both clonotype datasets 122. Horn's modification of the index, which is used as the basis for each pairwise clonotype dataset 122 comparison in FIG. 26 is:

$$C_H = \frac{2\sum_{i=1}^{S} x_i y_i}{\left(\frac{\sum_{i=1}^{S} x_i^2}{X^2} + \frac{\sum_{i=1}^{S} y_i^2}{Y^2}\right)XY}.$$

as set forth in Horn, 1966, 'Measurement of "Overlap" in comparative ecological studies,' The American Naturalist 100, pp. 419-424, which is hereby incorporated by reference.

Figure 27:
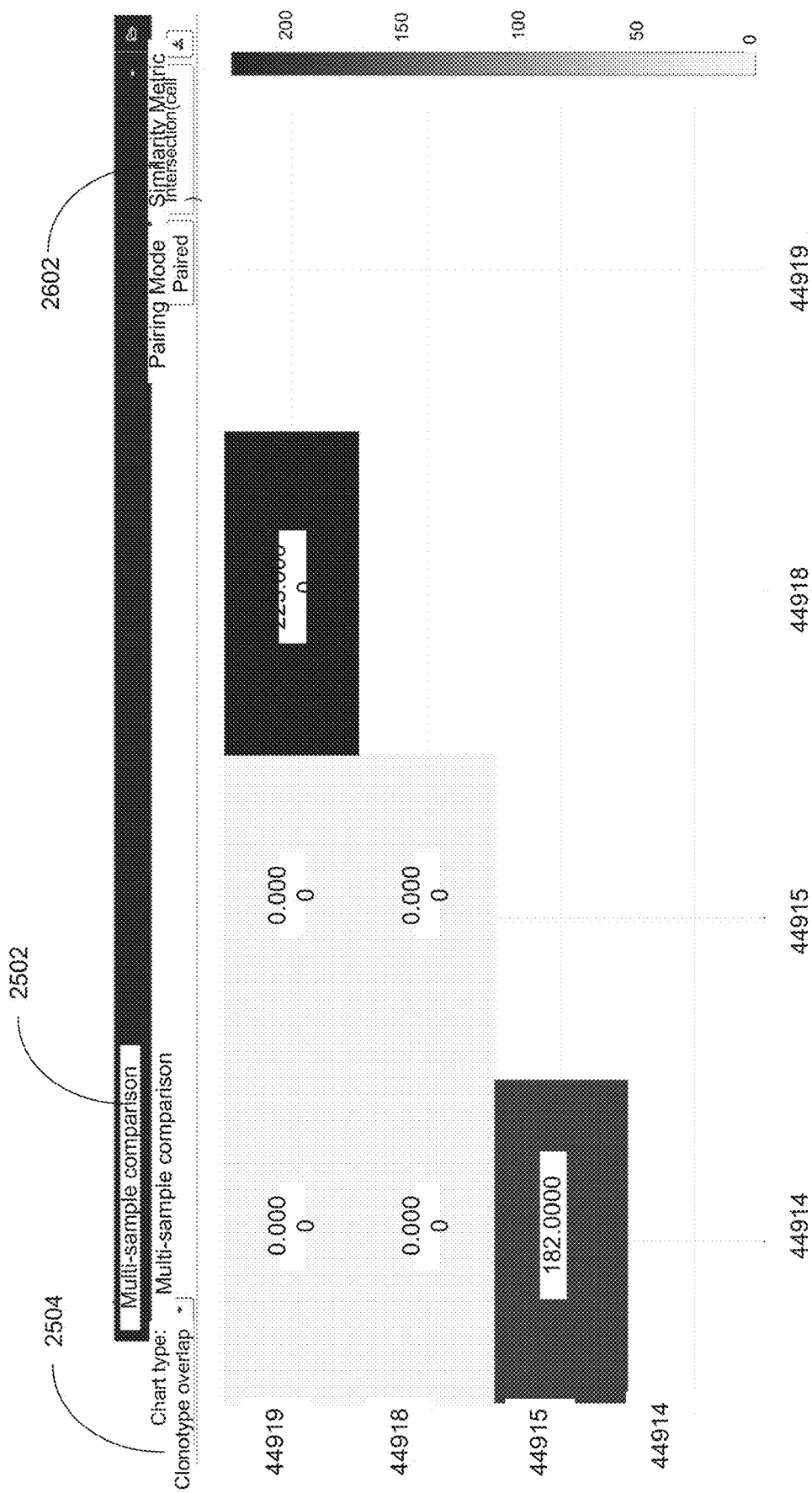
FIG. 27 illustrates the pairwise comparison of the four clonotype datasets of FIG. 25 showing the pairwise clonotype commonality between individual pairs of clonotype datasets among the four clonotype datasets using an intersection cell metric in accordance with some embodiments.

Referring to FIG. 27, the VDJ cell browser 120 provides for the pairwise comparison of the four clonotype datasets of FIG. 25 showing the pairwise clonotype commonality between individual pairs of clonotype datasets among the four clonotype datasets using an intersection cell metric selected by affordance 2602 in accordance with some embodiments. The intersection cell metric is the number of cells, for each respective comparison of two clonotype datasets 122, which belong to clonotypes 124 is present in both the clonotype datasets 122 being compared. Thus, referring to FIG. 27, there are 182 cells that have a clonotype present in both the "44915" and "44914" clonotype datasets 122 whereas there are no cells that are present in both the "44918" and 44914" clonotype datasets 122.

Figure 28:
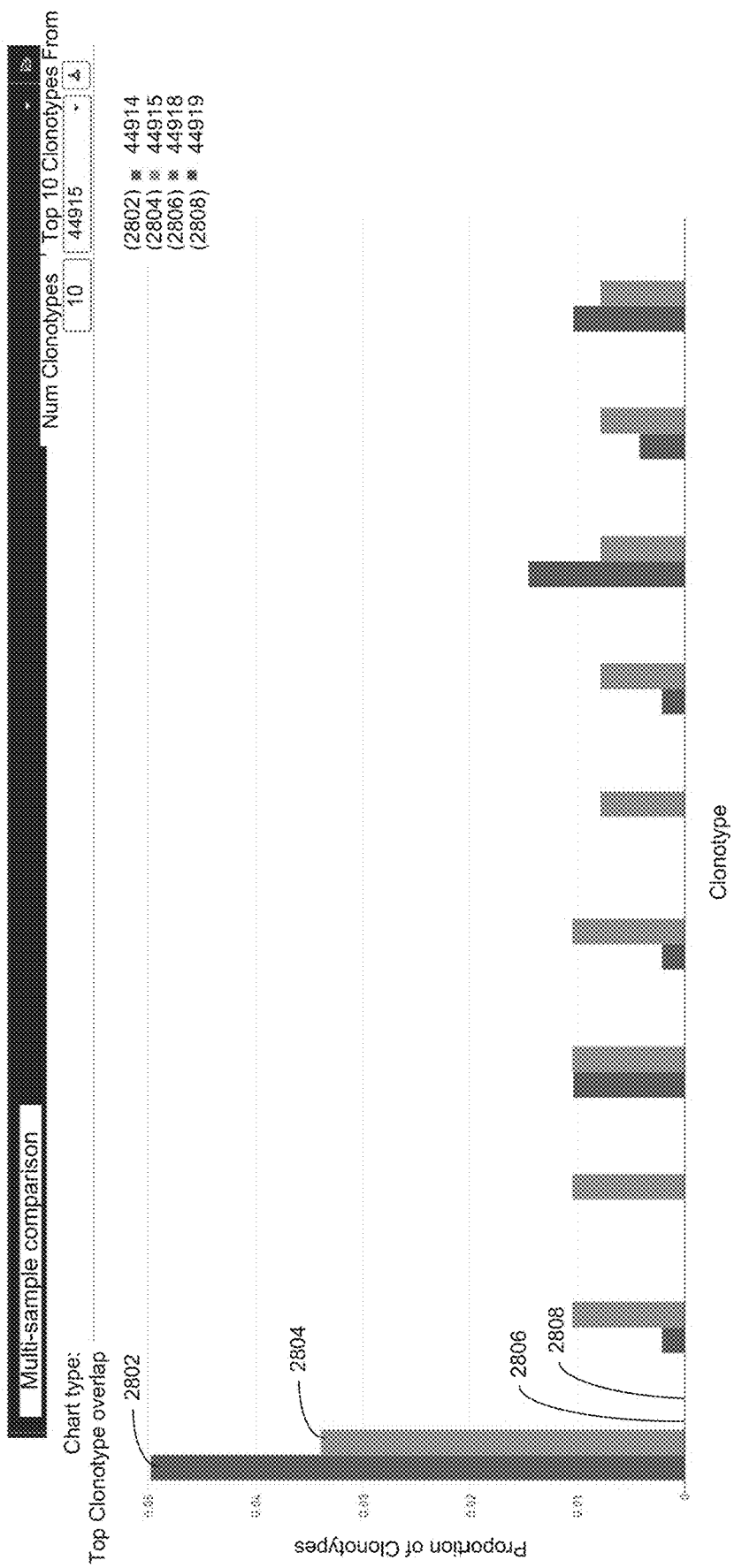
FIG. 28 illustrates, for a reference clonotype dataset (44914) among the four clonotype datasets of FIG. 25, the proportion of each respective clonotype in the top N represented clonotypes in the reference clonotype dataset and the corresponding proportion of each of these top clonotypes in the other clonotype datasets of FIG. 25 in accordance with some embodiments.

Referring to FIG. 28, in some embodiments, the VDJ cell browser 120 provides for each respective clonotype 124 in the top N clonotypes 124, by frequency in a first clonotype dataset 122 (where N is by default 10 in the embodiment illustrated in FIG. 28, but selectable), the frequencies of the respective clonotype in the other loaded clonotype datasets 122 is provided. For instance, referring to FIG. 28, the top clonotype 124 in the "44914" clonotype dataset 122 has a relative proportion of 0.05 in the "44914" clonotype dataset 122, 0.035 in the "44915" clonotype dataset 122, and is essentially not represented in the respective "44918" and "44919" clonotype datasets 122. This means, that the "44914" clonotype dataset 122, five percent of the cells represented by the "44914" dataset have the top represented clonotype 124 in that dataset, whereas 3.5 percent of the cells represented by the "44915" dataset have this same clonotype. The comparison of FIG. 28 is made possible by the fact that the disclosed clonotype datasets 122 are built upon single cell sequencing methods and the datasets 122 individually track the cells in the biological samples used to construct such datasets as disclosed above.

Figure 29:
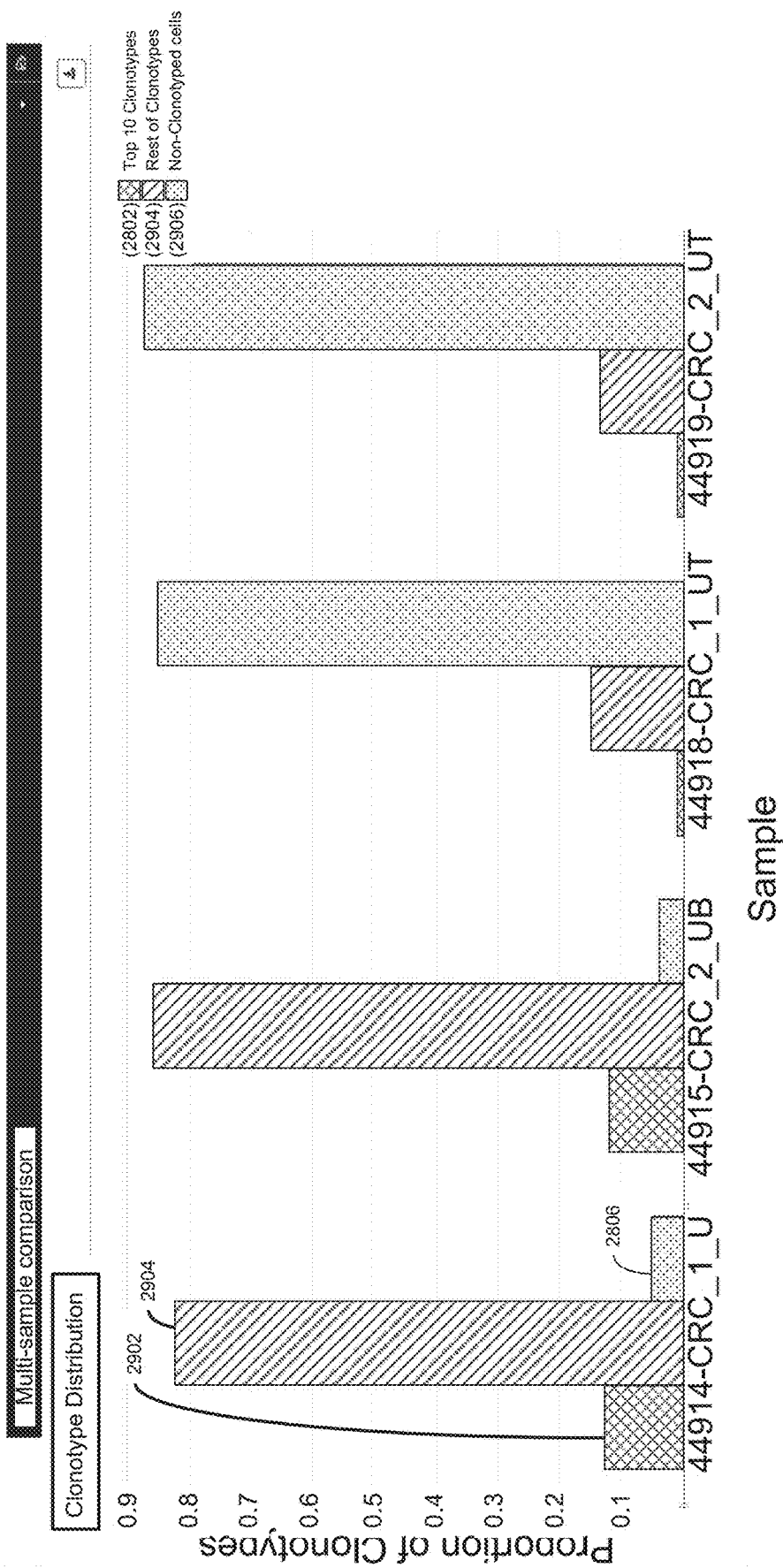
FIG. 29 illustrates, for each of the four clonotype datasets of FIG. 25, the proportion of clonotypes in the top 10 represented clonotypes in each respective clonotype dataset, the proportion of clonotypes outside the top 10 represented clonotypes in each respective clonotype dataset, and the proportion of cells that are non-clonotyped in each respective clonotype dataset in accordance with some embodiments.
Figure 30:
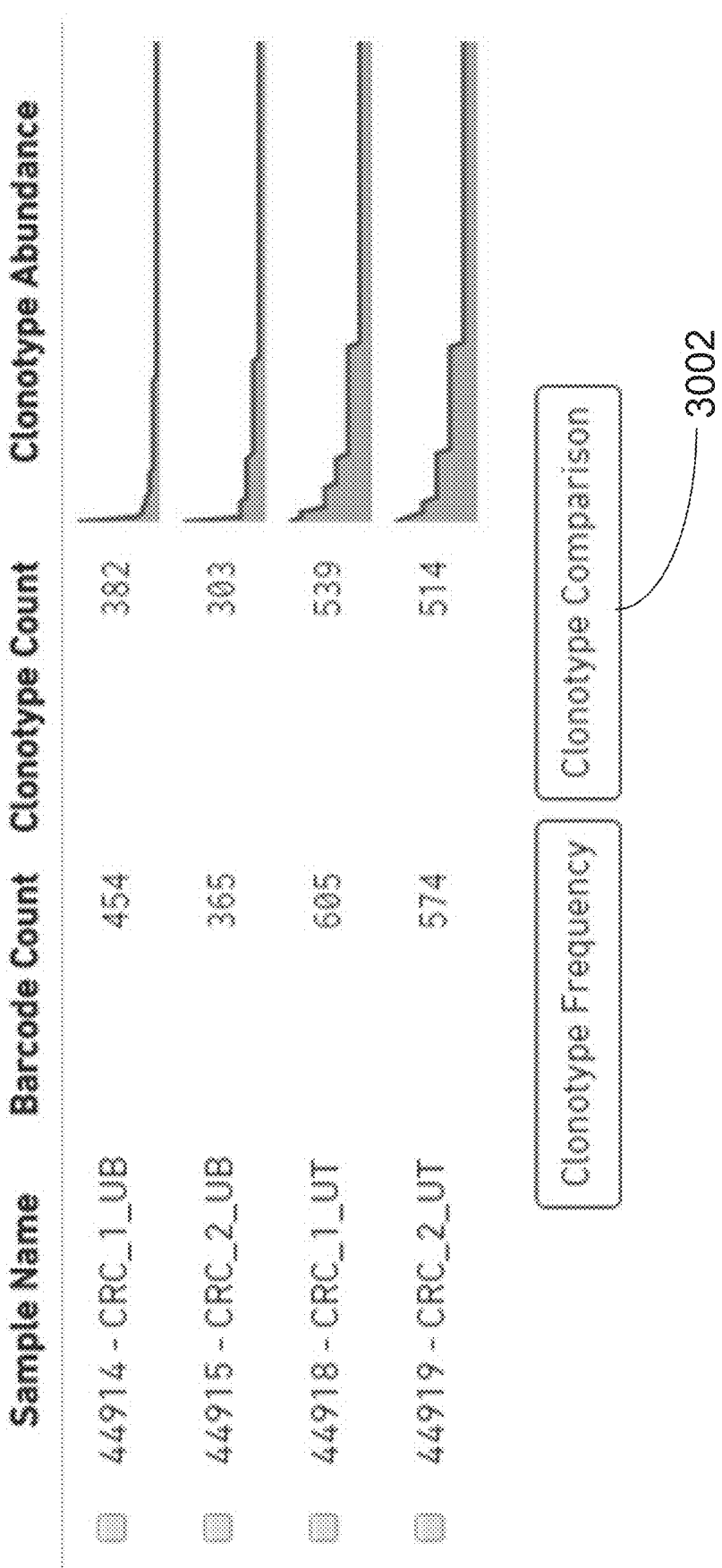
FIG. 30 illustrates how a user can select two of the four clonotype datasets of FIG. 25 for further clonotype comparison analysis in accordance with some embodiments.

In some embodiments, the VDJ cell browser 120 provides an indication of clonotype distribution in the open clonotype datasets 122. For example, referring to FIG. 29, in some embodiments VDJ cell browser 120 plots, for each of the four clonotype datasets of FIG. 25, the proportion of clonotypes in the top 10 represented clonotypes in each respective clonotype dataset, the proportion of clonotypes outside the top 10 represented clonotypes in each respective clonotype dataset, and the proportion of cells that are non-clonotyped in each respective clonotype dataset in accordance with some embodiments. The comparison of FIG. 29 is made possible by the fact that the disclosed clonotype datasets 122 are built upon single cell sequencing methods and the datasets 122 individually track the cells in the biological samples used to construct such datasets as disclosed above.

Figure 31:
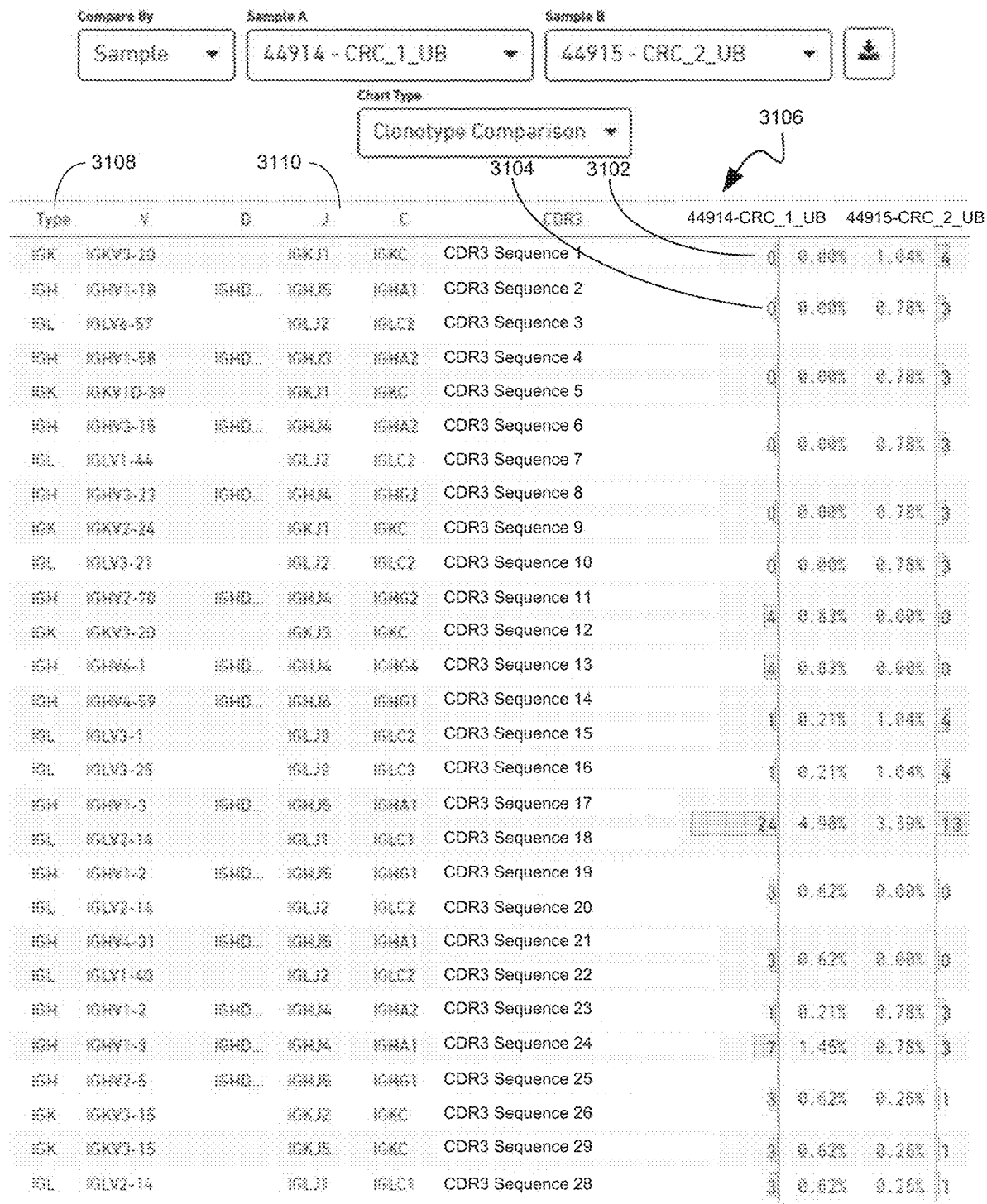
FIG. 31 illustrates a side by side clonotype cell count for the two clonotype datasets of FIG. 30, in tabular format in terms of raw cell counts and percentage cell count, across the clonotypes represented in the two clonotype datasets in accordance with some embodiments.

In some embodiments, the VDJ cell browser 120 provides a sample table 3106 that provides a comparison of the statistics of two selected clonotype datasets 122 that have been read by the VDJ cell browser 120. For example, referring to FIG. 30, in some embodiments the VDJ cell browser 120 allows a user to select two of the loaded clonotype datasets 122 for clonotype comparison analysis in accordance with some embodiments. Upon user selection of the "44914-CRC-1_UB" and "44915-CRC_2_UB" clonotype datasets 122 and selection of the "Clonotype Comparison" affordance 3002 of FIG. 30, the clonotypes are listed in table 3106 ordered by p-value (between the two clonotype datasets being compared) as computed by Fisher's exact test, and the list is filtered to cases where there are at least three cells of a particular clonotype in one of the samples. For instance, in the clonotype of set 3102 of table 3106, there are a total of four cells in the "44915-CRC_2_UB" clonotype dataset that have this clonotype and this accounts for 1.04% of the cells represented by the "44915-CRC_2_UB" clonotype dataset 122. By contrast, the "44914-CRC_2_UB" clonotype dataset 122 has no such clonotype 124. As another example, in clonotype 3104 of table 3106, the "44915-CRC_2_UB" clonotype dataset 122 has a total of three cells, accounting for 0.78% of the cells represented by the dataset, with the clonotype 3104. By contrast, the "44914-CRC_2_UB" clonotype dataset 122 again has no such clonotype 124. For each clonotype represented by table 3106, the cell type 3108, and an identity of the "V," "D," "J," and "C," regions and the sequence of the CDR3 region 3110 of each respective listed clonotype 124 is provided. The comparison of FIG. 31 is made possible by the fact that the disclosed clonotype datasets 122 are built upon single cell sequencing methods and the datasets 122 individually track the cells in the biological samples used to construct such datasets as disclosed above.

In some embodiments, the VDJ cell browser 120 provides a graph 3202 that provides a comparison of the frequency of occurrence of clonotypes within two selected clonotype datasets 122 that have been read by the VDJ cell browser 120. For example, referring to FIG. 30, in some embodiments the VDJ cell browser 120 allows a user to select two of the loaded clonotype datasets 122 for clonotype comparison analysis in accordance with some embodiments. Upon user selection of the "44914-CRC_1_UB" and "44915-CRC_2_UB" clonotype datasets 122 and selection of the "Clonotype Frequency" affordance 30004 of FIG. 30, VDJ cell browser 120 provides the clonotype frequency comparison graph 3206 of FIG. 32.

Figure 32:
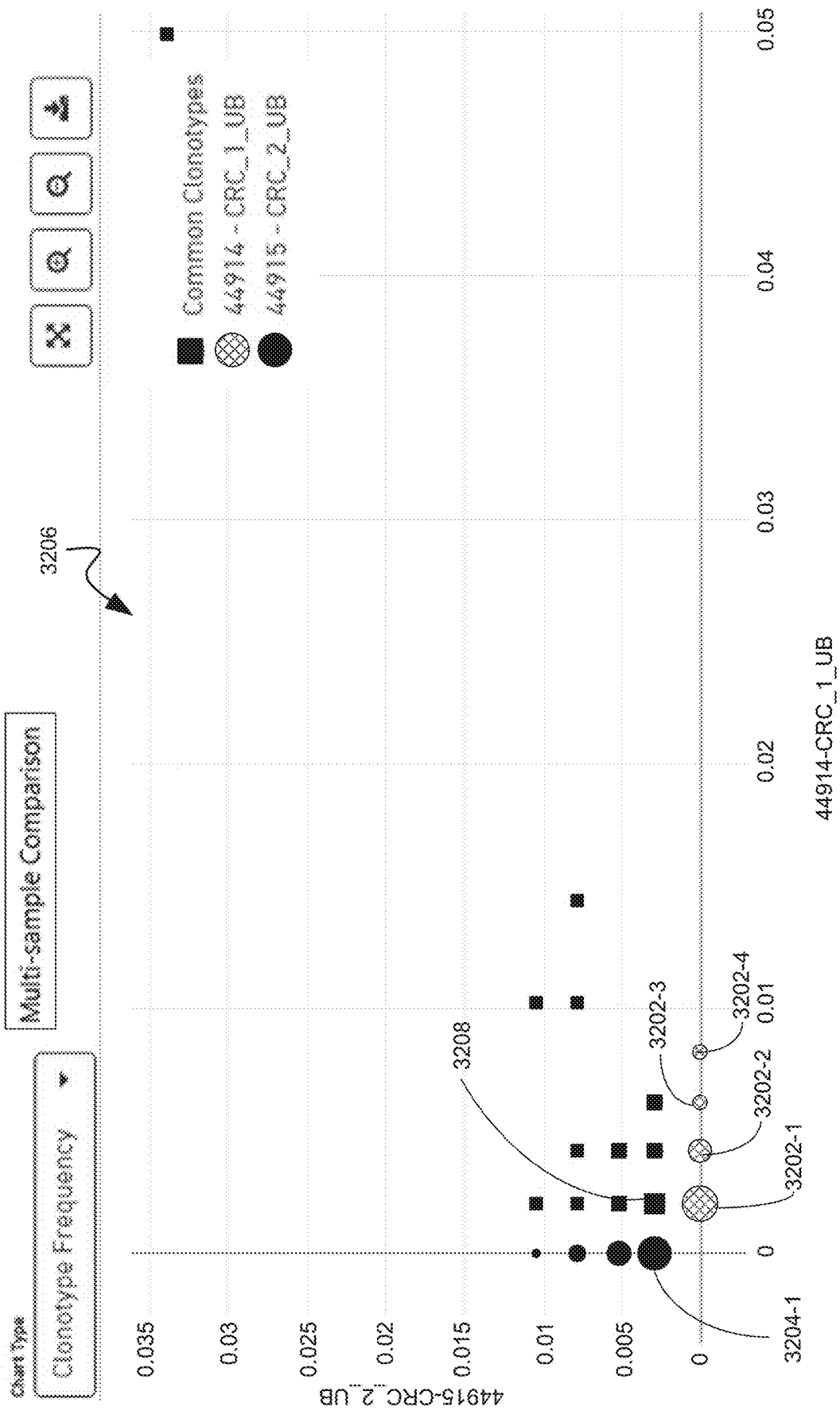
FIG. 32 illustrates the commonality in clonotypes between two clonotype datasets of FIG. 30, in a graphical proportional format, across the clonotypes represented in the two clonotype datasets in accordance with some embodiments.

In FIG. 32, the proportion of cells having respective clonotypes 124 represented by the "44914-CRC_1_UB" clonotype dataset 122 at a given frequency are arranged along the "X" axis as a function of this frequency of occurrence. Thus, on the "X" axis, the clonotypes 124 that appear with a frequency of "1" divided by the total number cells represented by the "44914-CRC_1_UB" dataset 122 (e.g., in the case of FIG. 32, $1/454$ or 0.00220) but do not appear in the "44915-CRC_2_UB" dataset 122 are represented by icon 3202-1. Although not shown in FIG. 32, when a user hovers their pointer device over icon 3202-1, the number of clonotypes that appear with a frequency of $1/454$ in the first clonotype dataset "44914-CRC_1_UB" and that are not found in the second clonotype dataset "44915-CRC_2_UB" are displayed. In this instance, there are 321 such clonotypes, which in this case means that 321 clonotypes in the "44914-CRC_1_ UB" are each uniquely represented by a single cell in the "44914-CRC_1_UB" dataset and are not found in any of the cells of the "44915-CRC_2_UB" dataset.

The clonotypes 124 that appear with a frequency of "2" divided by the total number cells represented by the "44914-CRC_1_UB" dataset 122 ($2/454$ or 0.00440) but do not appear in the "44915-CRC_2_UB" dataset 122 are represented by icon 3202-2. Although not shown in FIG. 32, when a user hovers their pointer device over icon 3202-2, the number of clonotypes that appear with a frequency of $2/454$ in the first clonotype dataset "44914-CRC_1_UB" and are not found in the second clonotype dataset "44915-CRC_2_UB" are displayed. In this instance, there are 10 such clonotypes, which in this case means that each of the 10 clonotypes is uniquely represented by two different cells in the "44914-CRC_1_UB" dataset and that none of these clonotypes are found in the "44915-CRC_2_UB" dataset.

The clonotypes 124 that appear with a frequency of "3" divided by the total number cells represented by the "44914-CRC_1_UB" dataset 122 ($3/454$ or 0.00660) but do not appear in the "44915-CRC_2_UB" dataset 122 are represented by icon 3202-3. Although not shown in FIG. 32, when a user hovers their pointer device over icon 3202-2, the number of clonotypes that appear with a frequency of $3/454$ in the first clonotype dataset "44914-CRC_1_UB" and are not represented in the second clonotype dataset "44915-CRC_2_UB" are displayed. In this instance, there are two such clonotypes, which in this case means that each of these two clonotypes is uniquely represented by three different cells in the "44914-CRC_1_UB" dataset and that none of these clonotypes are found in the "44915-CRC_2_UB" dataset.

In FIG. 32, the proportion of cells having respective clonotypes 124 represented by the "44915-CRC_2_UB" clonotype dataset 122 at a given frequency are arranged along the "Y" axis as a function of this frequency of occurrence. Thus, on the "Y" axis, the clonotypes 124 that appear with a frequency of "1" divided by the total number cells represented by the "44915-CRC_2_UB" dataset 122 ($1/365$ or 0.00270) but do not appear in the "44915-CRC_2_UB" dataset 122 are represented by icon 3204-1. Although not shown in FIG. 32, when a user hovers their pointer device over icon 3402-1, the number of clonotypes that appear with a frequency of $1/365$ in the second clonotype dataset "44915-CRC_2_UB" but are not found in the first clonotype dataset "44914-CRC_1_UB" are displayed. In this instance, there are 237 such clonotypes, which in this case means that 237 cells in the "44915-CRC_2_UB" have a unique clonotype that is not represented by any other cells in the "44915-CRC_2_UB" dataset and are not found in any of the cells of the "44914-CRC_1_UB" dataset.

Icon 3208 is the frequency intersection between icons 3202-1 and 3204-1. As such, icon 3208 represents the number of clonotypes that appear with a frequency of $1/454$ in the "44914-CRC_1_UB" dataset (1/total cells in the first dataset) and a frequency of $1/365$ in the "44915-CRC_2_UB" dataset (1/total cells in the second dataset). Although not shown in FIG. 32, when a user hovers their pointer device over icon 3208, the number clonotype that appear with a frequency of $1/365$ in the second clonotype dataset "44915-CRC_2_UB" and a frequency of $1/454$ in the first clonotype dataset "44914-CRC_1_UB" are displayed. In this instance, there are 24 such clonotypes, which in this case means that there are 24 clonotype that are each represented by a single unique cell in the "44915-CRC_2_UB" dataset and the "44914-CRC_1_UB" dataset.

FIG. 32 provides a visual basis for determining the similarity in the frequency of clonotype occurrence between the two clonotype datasets. The comparison of FIG. 32 is made possible by the fact that the disclosed clonotype datasets 122 are built upon single cell sequencing methods and the datasets 122 individually track the cells in the biological samples used to construct such datasets as disclosed above.

Turning to FIGS. 33 through 36, in some embodiments the VDJ cell browser can be used to display the relative proportion of specific V, D, J, and C genes across all the clonotype datasets that have been selected or opened by the browser.

Figure 33:
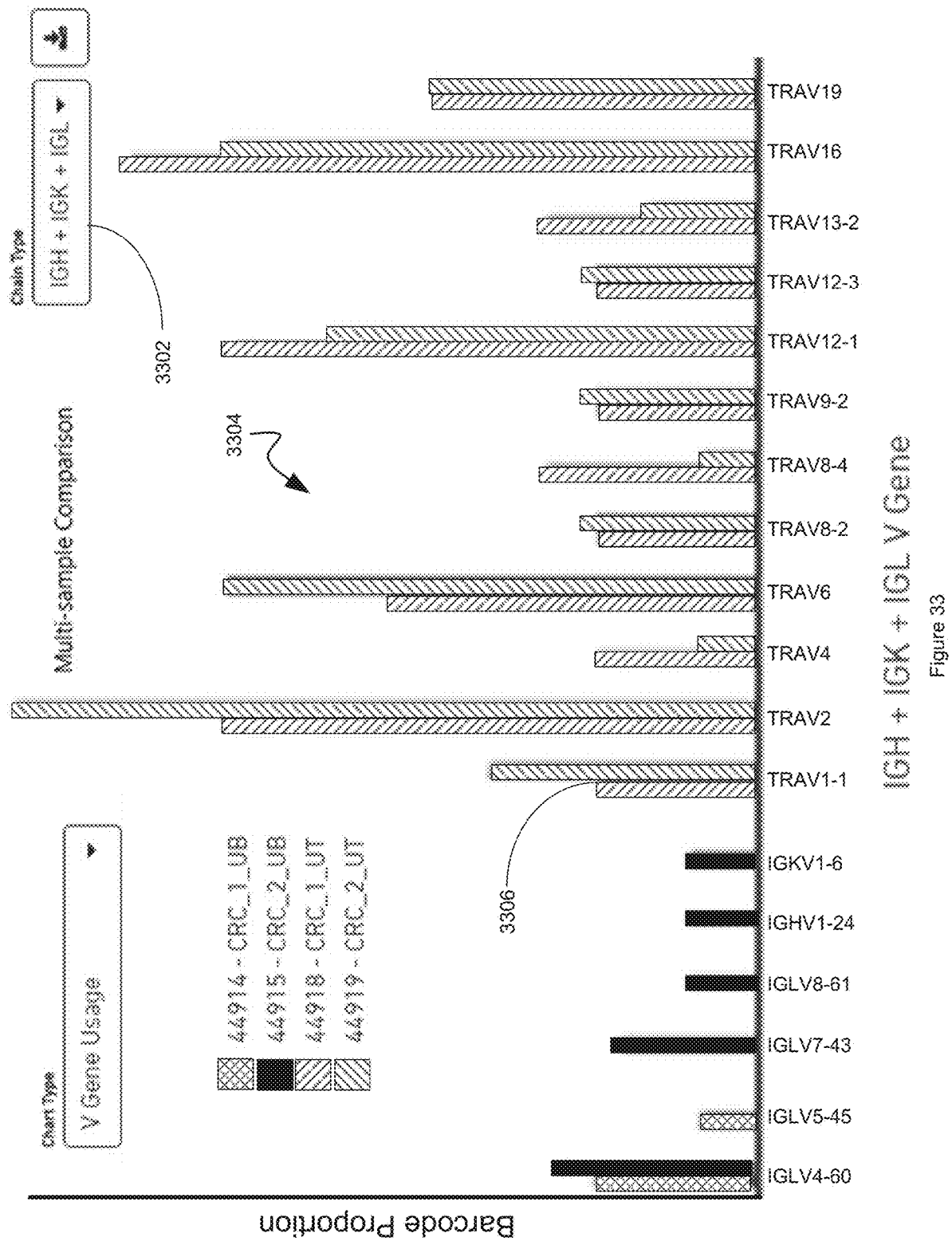
FIG. 33 illustrates, for each of the four clonotype datasets of FIG. 25, the relative frequency of respective D gene across each respective clonotype dataset, in accordance with some embodiments.

Thus, turning to FIG. 33, V gene usage across the cells of the four biological samples used to construct the four clonotype datasets 122 loaded in the manner illustrated in FIG. 24 are displayed. The V gene usage is the annotated V region counted for each of the clonotypes 124 in the respective datasets. In other words, V gene usage is an aggregate of all V gene usage of each of the possible different human V genes (e.g., IGLV4-60, IGLV45-45, IGLV7-43, IGLV8-61, etc.) plotted by frequency (barcode proportion), on a clonotype dataset 122 by clonotype dataset 122 basis, regardless of which chain the represented V genes occur in. Thus, in the case of the V gene TRAV1-1, a barcode count of each instance of this V gene, regardless of chain type occurrence is provided in FIG. 33 for each of the four clonotype datasets 122 being compared. Although not shown in FIG. 33, when a user moves their pointer device over a set of graph bars that represent a specific V-gene in the Figure, the barcode proportions for that specific V gene are displayed. For instance, if the user hovers their pointing device over the graph bars corresponding to the V gene "Trav1-1" in FIG. 33, the barcode proportions in each of the four clonotype datasets being compared (if present in the clonotype datasets) is provided. In the case of the datasets being compared in FIG. 33, hovering over the set of bars 3306 reveals that the TRAV1-1 V gene has a barcode proportion of 0.006195787 in the "44919-CRC_2_UT" dataset, a proportion of 0.00365408 in the "44918-CRC-1_UT" dataset, and no presence in the two other datasets represented by chart 3304. Moreover, affordance 3302 can be used to select the chain type that is analyzed for V gene barcode proportion. In the case where clonotype datasets comprising T cells are being compared, this would be the α chain only, β chain only, or both α chain and β chain. In the case illustrated in FIG. 33, where clonotype datasets 122 comprising B cells are being compared, affordance 3302 is used to select heavy chain only (IGH), kappa chain (light chain) only (IGK), lamba chain (light chain) only (IGL) or the combination of all three (IGH, IGHK, and IGL). For instance, if affordance 3302 is changed to IGH, graph 3304 only displays the barcode frequency of occurrence of each V gene type, on a clonotype dataset 122 by clonotype dataset 122 basis, across the IGH that occur in each of the loaded clonotype datasets 122.

Figure 34:
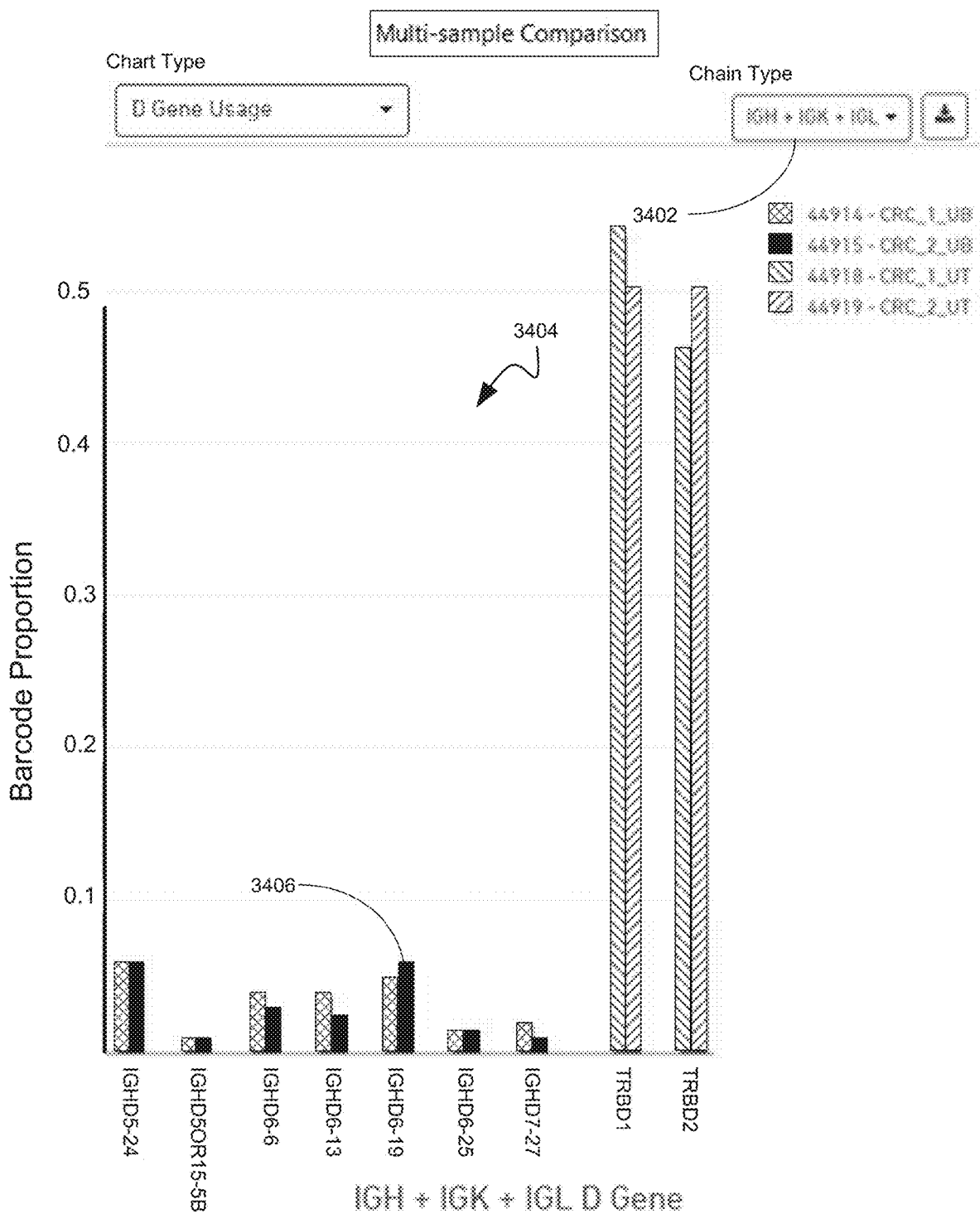
FIG. 34 illustrates, for each of the four clonotype datasets of FIG. 25, the relative frequency of respective D gene across each respective clonotype dataset, in accordance with some embodiments.

Turning to FIG. 34, D gene usage across the cells of the four biological samples used to construct the four clonotype datasets 122 loaded in the manner illustrated in FIG. 24 are displayed. The D gene usage is the annotated D region counted for each of the clonotypes 124 in the respective datasets. In other words, D gene usage is an aggregate of all D gene usage of each of the possible different human D genes (e.g., IGHD5-24, IGHD50R15-5B, IGHD6-6, IGHD6-13, IGHD6-19, etc.) plotted by frequency (barcode proportion), on a clonotype dataset 122 by clonotype dataset 122 basis, regardless of which chain the represented D genes occur in. Thus, in the case of the D gene IGHD6-19, a barcode count of each instance of this D gene, regardless of chain type occurrence is provided in FIG. 34 for each of the four clonotype datasets 122 being compared. Although not shown in FIG. 34, when a user moves their pointer device over a set of graph bars that represent a specific D gene in the FIG. 34, the barcode proportions for that specific D gene are displayed. For instance, if the user hovers their pointing device over the graph bars corresponding to the D gene "IGHD6-19" in FIG. 34, the barcode proportions in each of the four clonotype datasets being compared (if present in the clonotype datasets) is provided. In the case of the datasets being compared in FIG. 34, hovering over the set of bars 3406 reveals that the IGHD6-19 D gene has a barcode proportion of 0.04597701 in the "44914-CRC_1_UB" dataset, a proportion of 0.0569395 in the "44915-CRC-2_UB" dataset, and no presence in the two other datasets represented by chart 3404. Moreover, affordance 3402 can be used to select the chain type that is analyzed for D gene barcode proportion. In the case where clonotype datasets comprising T cells are being compared, this would be the α chain only, β chain only, or both α chain and β chain. In the case illustrated in FIG. 34, where clonotype datasets 122 comprising B cells are being compared, affordance 3402 is used to select heavy chain only (IGH), kappa chain (light chain) only (IGK), lamba chain (light chain) only (IGL) or the combination of all three (IGH, IGHK, and IGL). For instance, if affordance 3402 is changed to IGH, graph 3404 only displays the barcode frequency of occurrence of each D gene type, on a clonotype dataset 122 by clonotype dataset 122 basis, across the IGH that occur in each of the loaded clonotype datasets 122.

Figure 35:
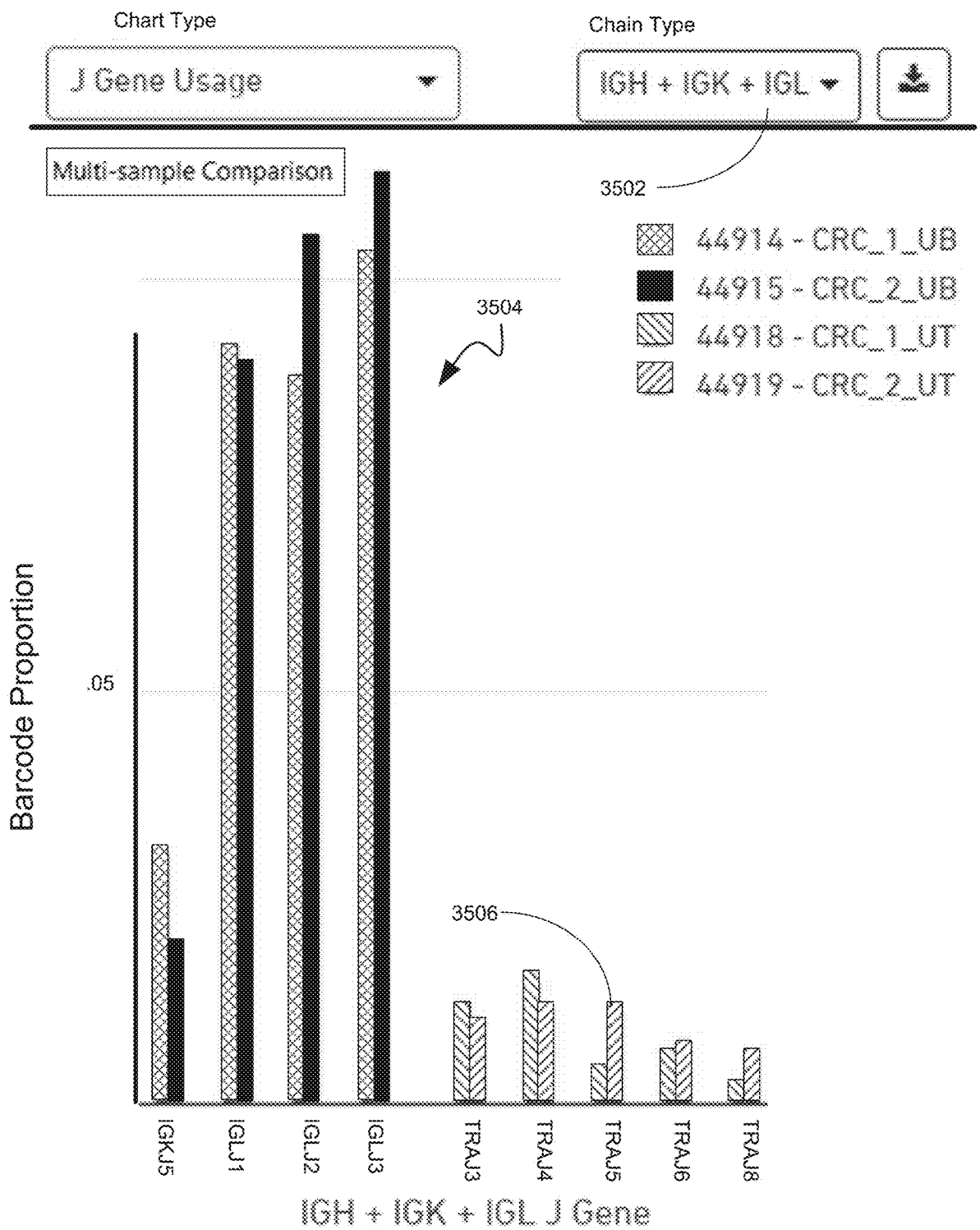
FIG. 35 illustrates, for each of the four clonotype datasets of FIG. 25, the relative frequency of respective J gene across each respective clonotype dataset, in accordance with some embodiments.

Turning to FIG. 35, J gene usage across the cells of the four biological samples used to construct the four clonotype datasets 122 loaded in the manner illustrated in FIG. 24 are displayed. The J gene usage is the annotated J region counted for each of the clonotypes 124 in the respective datasets. In other words, J gene usage is an aggregate of all J gene usage of each of the possible different human J genes (e.g., IGKJ5, IGLJ1, IGLJ2, IGLJ3, TRAJ3, TRAJ4, TRAJ5, TRAJ6, TRAJ8, etc.) plotted by frequency (barcode proportion), on a clonotype dataset 122 by clonotype dataset 122 basis, regardless of which chain the represented J genes occur in. Thus, in the case of the J gene TRAJ5, a barcode count of each instance of this J gene, regardless of chain type occurrence is provided in FIG. 35 for each of the four clonotype datasets 122 being compared. Although not shown in FIG. 35, when a user moves their pointer device over a set of graph bars that represent a specific J gene in the FIG. 35, the barcode proportions for that specific J gene are displayed. For instance, if the user hovers their pointing device over the graph bars corresponding to the J gene "TRAJ5" in FIG. 35, the barcode proportions in each of the four clonotype datasets being compared (if present in the clonotype datasets) is provided. In the case of the datasets being compared in FIG. 35, hovering over the set of bars 3506 reveals that the TRAJ5 J gene has a barcode proportion of 0.01115242 in the "44919-CRC_2_UT" dataset, a proportion of 0.00365408 in the "44918-CRC-1_UT" dataset, and no presence in the two other datasets represented by chart 3504. Moreover, affordance 3502 can be used to select the chain type that is analyzed for J gene barcode proportion across the multi-sample comparison. In the case where clonotype datasets 122 comprising T cells are being compared, this would be the α chain only, β chain only, or both α chain and β chain. In the case illustrated in FIG. 35, where clonotype datasets 122 comprising B cells are being compared, affordance 3502 is used to select heavy chain only (IGH), kappa chain (light chain) only (IGK), lamba chain (light chain) only (IGL) or the combination of all three (IGH, IGHK, and IGL). For instance, if affordance 3502 is changed to IGH, graph 3504 only displays the barcode frequency of occurrence of each J gene type, on a clonotype dataset 122 by clonotype dataset 122 basis, across the IGH that occur in each of the loaded clonotype datasets 122.

Figure 36:
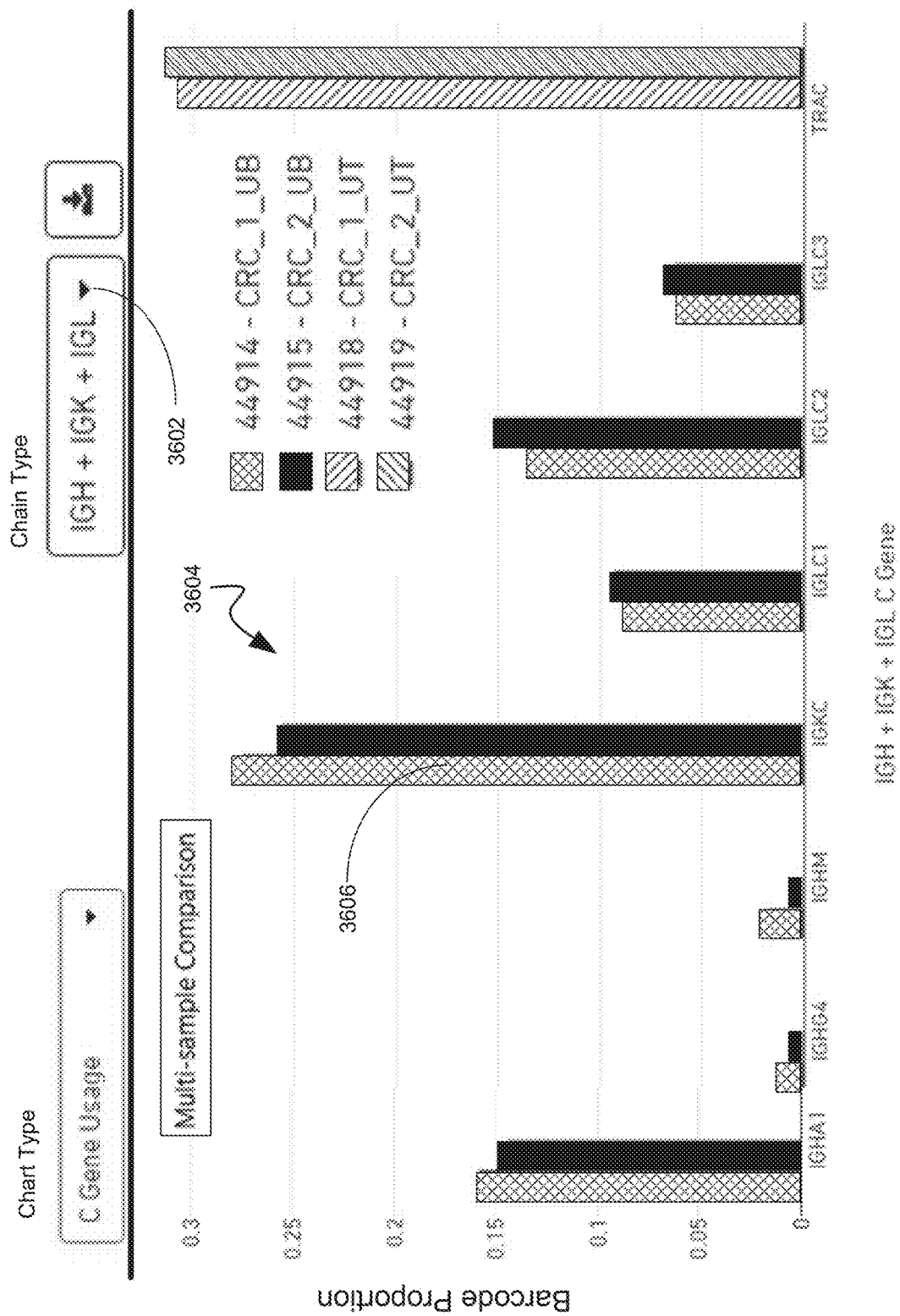
FIG. 36 illustrates, for each of the four clonotype datasets of FIG. 25, the relative frequency of respective C gene across each respective clonotype dataset, in accordance with some embodiments.

Turning to FIG. 36, C gene usage across the cells of the four biological samples used to construct the four clonotype datasets 122 loaded in the manner illustrated in FIG. 24 are displayed. The C gene usage is the annotated C region counted for each of the clonotypes 124 in the respective datasets. In other words, C gene usage is an aggregate of all C gene usage of each of the possible different human C genes (e.g., IGHA1, IGHG4, IGHM, IGKC, IGLC1, IGLC2, IGLC3, TRAC, etc.) plotted by frequency (barcode proportion), on a clonotype dataset 122 by clonotype dataset 122 basis, regardless of which chain the represented C genes occur in. Thus, in the case of the C gene IGKC, a barcode count of each instance of this C gene, regardless of chain type occurrence is provided in FIG. 36 for each of the four clonotype datasets 122 being compared. Although not shown in FIG. 36, when a user moves their pointer device over a set of graph bars that represent a specific C gene in the FIG. 36, the barcode proportions for that specific C gene are displayed. For instance, if the user hovers their pointing device over the graph bars corresponding to the C gene "IGKC" in FIG. 36, the barcode proportions in each of the four clonotype datasets being compared is provided. In the case of the datasets being compared in FIG. 36, hovering over the set of bars 3606 reveals that the IGKC gene has a barcode proportion of 0.2756005 in the "44914-CRC_1_UB" clonotype dataset 122, a proportion of 0.255814 in the "44915-CRC_2_UB" dataset, and no presence in the two other datasets represented by chart 3604. Moreover, affordance 3602 can be used to select the chain type that is analyzed for C gene barcode proportion across the multi-sample comparison. In the case where clonotype datasets 122 comprising T cells are being compared, this would be the α chain only, β chain only, or both α chain and β chain. In the case illustrated in FIG. 36, where clonotype datasets 122 comprising B cells are being compared, affordance 3602 is used to select heavy chain only (IGH), kappa chain (light chain) only (IGK), lamba chain (light chain) only (IGL) or the combination of all three (IGH, IGHK, and IGL). For instance, if affordance 3602 is changed to IGH, graph 3604 only displays the barcode frequency of occurrence of each Cgene type, on a clonotype dataset 122 by clonotype dataset 122 basis, across the IGH that occur in each of the loaded clonotype datasets 122.

The comparison of FIGS. 33-36 is made possible by the fact that the disclosed clonotype datasets 122 are built upon single cell sequencing methods and the clonotype datasets 122 individually track the cells in the biological samples used to construct such datasets as disclosed above.

Figure 37:
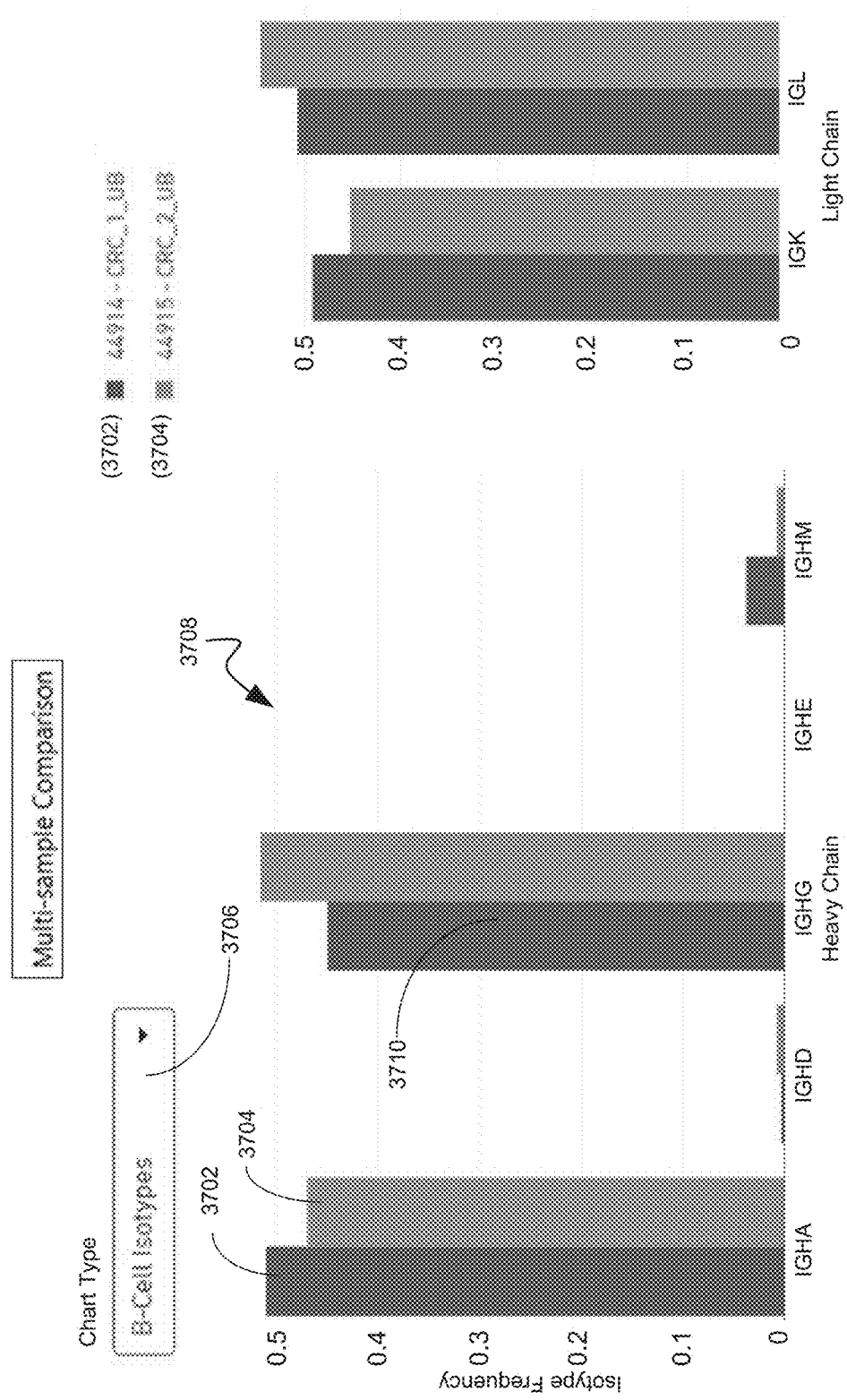
FIG. 37 illustrates, for two selected clonotype datasets, the relative distribution of heavy and light chain isotypes across the two selected clonotype datasets, in accordance with some embodiments.

Referring to FIG. 37, toggling affordance 3706 to select the "B-Cell Isotypes" chart type when clonotype datasets based upon the single cell sequencing of B-cells have been loaded by the VDJ cell browser 120 results in the display by the VDJ cell browser 120 of graph 3708. Graph 3708 shows the isotype frequency of the heavy chain isotypes (e.g., IGHA, IGHD, IGHG, IGHE, and IGHM) and the isotype frequency of the light chain isotypes (e.g., IGK, IGL) across all loaded clonotype datasets 122. Although not shown in FIG. 37, when a user moves their pointer device over a set of graph bars that represent a specific chain type in the figure, the respective isotype frequency for that specific chain type in each respective clonotype dataset (if present in the clonotype datasets) is displayed. For instance, if the user hovers their pointing device over the graph bars corresponding to the IGHG heavy chain in FIG. 37, the isotype frequency of the IGHG heavy chain in the two clonotype datasets that include B cells is provided (e.g., 0.5160142 in the "44915-CRC_1_UB" dataset and 0.4498567 in the "44914-CRC_1_UB" dataset). The comparison of FIG. 37 is made possible by the fact that the disclosed clonotype datasets 122 are built upon single cell sequencing methods and the clonotype datasets 122 individually track the cells in the biological samples used to construct such datasets as disclosed above.

B-Cell Paired Isotypes.

Figure 38:
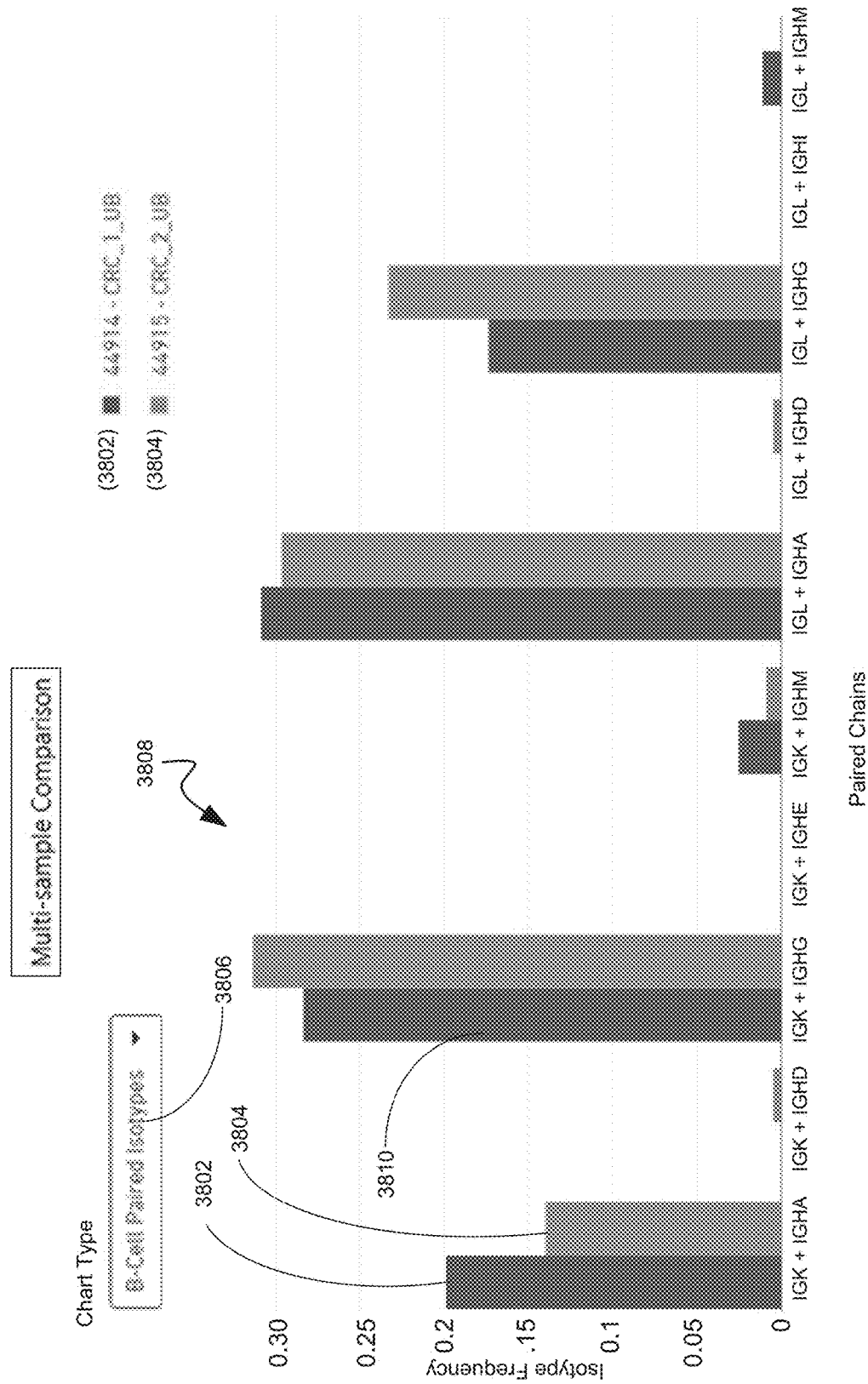
FIG. 38 illustrates, for two selected clonotype datasets, the relative distribution of heavy plus light chain paired combinations across the two selected clonotype datasets, in accordance with some embodiments.

The relative distribution of heavy+light chain combinations for all loaded B-cell samples is illustrated in FIG. 38. Thus, referring to FIG. 38, toggling affordance 3806 to select the "B-Cell Paired Isotypes" chart type when clonotype datasets based upon the single cell sequencing of B-cells have been loaded by the VDJ cell browser 120 results in the display by the VDJ cell browser 120 of graph 3808. Graph 3808 shows the relative distribution of heavy+light chain combinations for all loaded B-cell samples on a clonotype dataset 122 by clonotype dataset 122 basis (e.g., IGK+IGHA, IGK+IGHD, IGK_IGHG, etc.). Although not shown in FIG. 38, when a user moves their pointer device over a set of graph bars that represent a specific chain type pair in the figure, the respective frequency of the chain type pair in each respective clonotype dataset (if present in the clonotype datasets) is displayed. For instance, if the user hovers their pointing device over the graph bars corresponding to the IGK+IGHG chain combination in FIG. 38, the isotype frequency of this chain type pair in the two clonotype datasets that include B cells is provided (e.g., 0.3135593 in the "44915-CRC_1_UB" dataset and 0.2836879 in the "44914-CRC_1_UB" dataset). The comparison of FIG. 38 is made possible by the fact that the disclosed clonotype datasets 122 are built upon single cell sequencing methods and the clonotype datasets 122 individually track the cells in the biological samples used to construct such datasets as disclosed above.

Figure 39:
FIG. 39 illustrates, for two selected clonotype datasets upon selecting the "Clonotype Comparison" affordance of FIG. 30, a clonotype-level comparison between the two selected clonotype datasets in tabular format indicating the number and proportion of cells in each of the two selected clonotype datasets that have each clonotype and indicating, for each such respective clonotype, the identity of the V, D, J, and C genes and the amino acid sequence of the CDR3 region for the respective clonotype in accordance with some embodiments.

Referring to FIG. 39, selecting the "Clonotype Comparison" chart type using affordance 3902 causes VDJ cell browser 120 to provide a clonotype-level comparison between two selected clonotype datasets (Sample A and Sample B) in the form of table 3904. Each set of lines in table 3904 represents a clonotype 124 that is present in at least one of the two clonotype datasets 122 being compared. For each clonotype 124 listed in table 3904, chain type, and designation of the V gene, D gene, J gene, and C gene, and the amino acid sequence of the CDR3 region is provided. Furthermore, the number of cells having this respective clonotype in each of the two selected clonotype datasets is provided along with a designation of what percent of the cells in each of the selected clonotype datasets have this respective clonotype. In the embodiment illustrated in FIG. 39, the clonotypes are ordered by p-value (between the two clonotype datasets being compared) as computed by Fisher's exact test, and the list is filtered to cases where there are at least three cells of a particular clonotype in one of the samples. Table 3904 shows a comparison of paired single-cell clonotype frequencies between two clonotype datasets 122. The comparison of FIG. 39 is made possible by the fact that the disclosed clonotype datasets 122 are built upon single cell sequencing methods and the clonotype datasets 122 individually track the cells in the biological samples used to construct such datasets as disclosed above.

Integration of Gene Expression Data.

Figure 40:
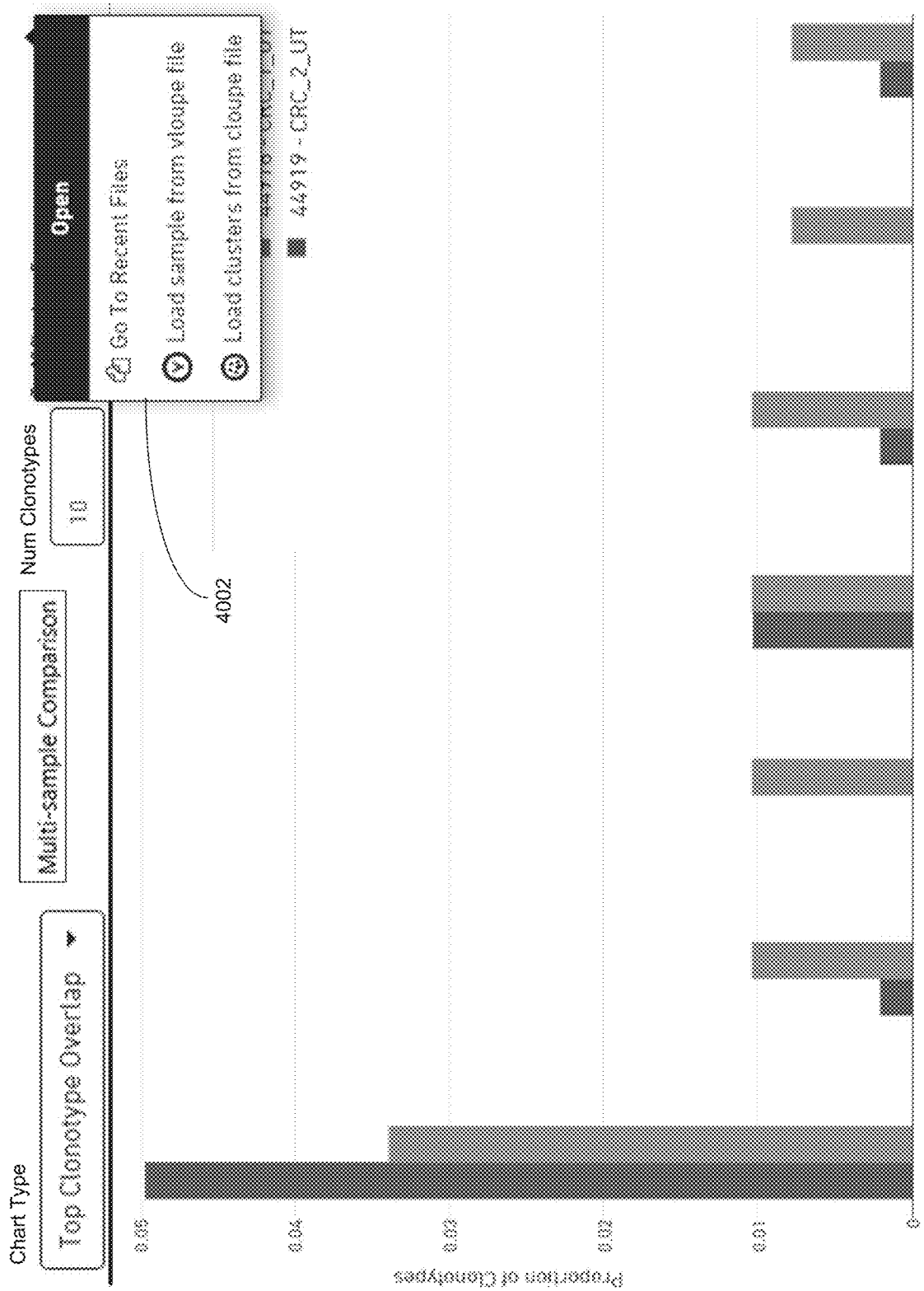
FIG. 40 illustrates how clusters from a clustered dataset can be loaded while multiple clonotype datasets are open and concurrently being analyzed in accordance with some embodiments.
Figure 41:
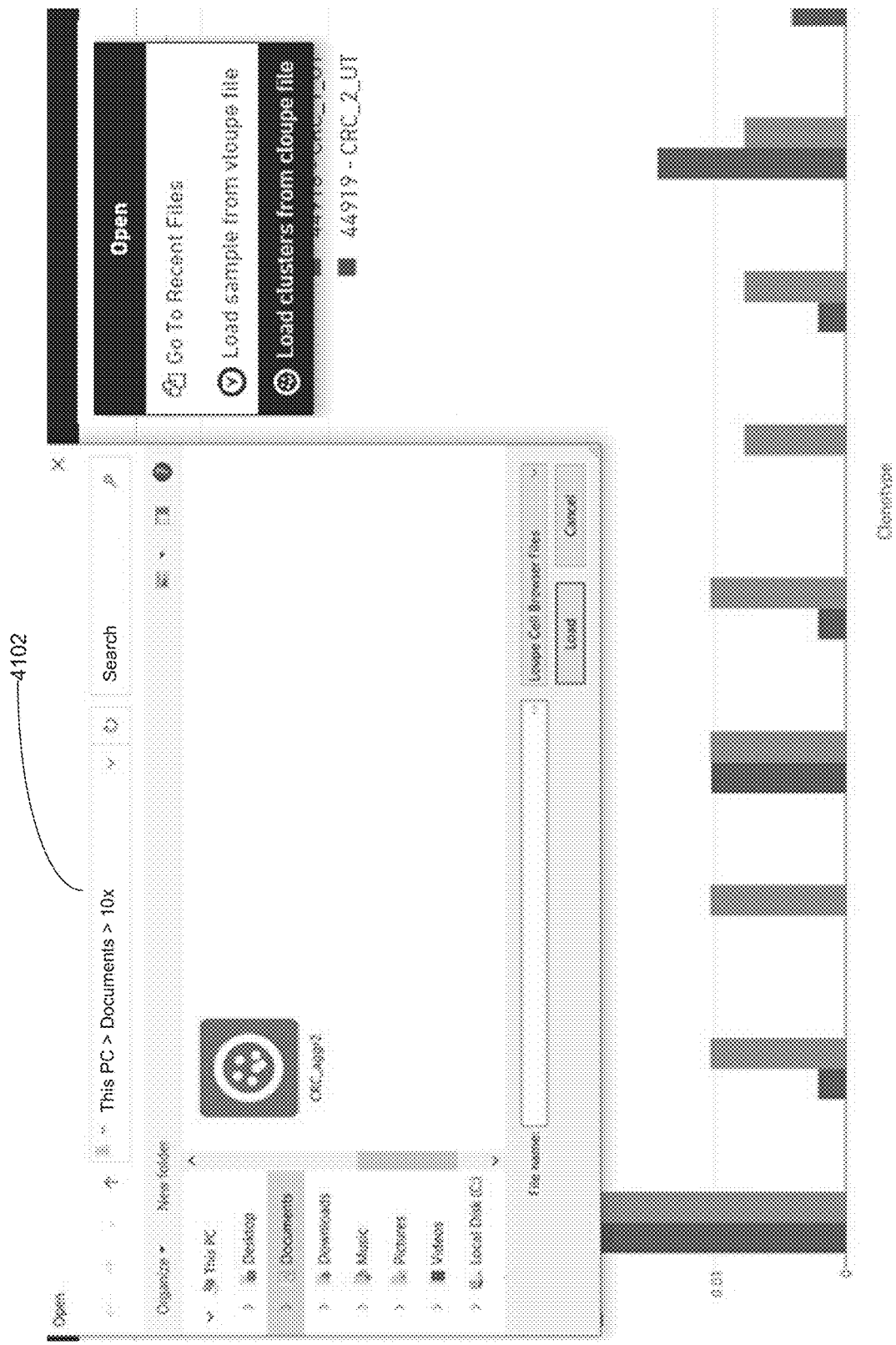
FIG. 41 illustrates the selection of a clustered dataset for loading while multiple clonotype datasets are open and concurrently being analyzed in accordance with some embodiments.

Referring to FIGS. 40 and 41, advantageously, in addition to loading clonotype datasets 122, VDJ cell browser can load one or more of the clustered datasets 180 having the format described in U.S. patent application Ser. No. 15/891,607, entitled "Systems and Methods for Visualizing a Pattern in a Dataset," filed Feb. 8, 2018, which is hereby incorporated by reference. As described in U.S. patent application Ser. No. 15/891,607, a discrete attribute value dataset is obtained. The discrete attribute value dataset comprises, for each respective second entity (e.g., cell) in a plurality of second entities (e.g., a plurality of cells), a discrete attribute value (e.g., count of transcript reads mapped to a single gene) for each first entity (e.g. gene) in a plurality of first entities (e.g., genes). In some embodiments, each first entity in the plurality of first entities for a given second entity is a respective gene in a plurality of genes. Each discrete attribute value is a count of transcript reads within the second entity that map to a respective gene in the plurality of genes. In such embodiments, each second entity 126 is a single cell. The discrete attribute value dataset represents a whole transcriptome shotgun sequencing experiment that quantifies gene expression from a single cell in counts of transcript reads mapped to the genes.

In some embodiments mRNA from a single cell is amplified and barcoded with the same barcode. In some such embodiments, discrete attribute values are measured from single cells, and microfluidic partitions are used to capture such individual cells within respective microfluidic droplets and then pools of single barcodes within each of those droplets are used to tag all of the contents (e.g., mRNA corresponding to genes) of a given cell. For example, in some embodiments, a pool (e.g., of ~750,000 barcodes) is sampled to separately index each second entities' transcriptome by partitioning thousands of second entities into nanoliter-scale Gel Bead-In-EMulsions (GEMs), where all generated cDNA share a common barcode. In some embodiments, each respective droplet (GEM) is assigned its own barcode and all the contents (e.g., first entities) in a respective droplet are tagged with the barcode unique to the respective droplet. In some embodiments, such droplets are formed as described in Zheng et al., 2016, Nat Biotchnol. 34(3): 303-311; in the Chromium, Single Cell 3' Reagent Kits v2. User Guide, 2017, 10× Genomics, Pleasanton, California, Rev. B, or the Chromium Single Cell V(D)J Reagent Kits User Guide, 2017, 10× Genomics, Pleasanton, California, each of which is hereby incorporated by reference.

The amplified DNA from such mRNA, now barcoded, is pooled across the population of cells in a test sample (e.g. a tumor biopsy, etc.) and then divided into two or more aliquots, three or more aliquots, four or more aliquots, ten or more aliquots, etc. Each such respective aliquot includes one or more barcoded cDNA constructs, for each of the mRNA in each cell in the original sample. That is, each respective aliquot fully represents the relative expression of each expressed gene from each cell in the original sample. Moreover, because the expressed gene (e.g., in the form of mRNA) was barcoded upon amplification to cDNA, it is possible to identify a cDNA from one of the aliquots as being from the same gene as the cDNA from the other aliquots, because they will have matching barcodes. As such, one of the respective aliquots is applied to the general V(D)J transcript library construction and selection protocol described above thereby populating the clonotype dataset 122, and another of the aliquots follows a 5' gene expression library construction protocol, such as that described in the section entitled "Discrete attribute value pipeline" in U.S. Patent Application No. 62/572,544, entitled "Systems and Methods for Visualizing a Pattern in a Dataset," filed Oct. 15, 2017, thereby populating the discrete attribute values for each gene for each cell in the test sample in a discrete attribute value dataset. In some embodiments, the test sample comprise 10 or more second entities, 100 or more second entities, or 1000 or more second entities. In some embodiments, the test sample is a biopsy from a subject, such as a human subject. In some embodiments, the sample is a biopsy of a tumor and contains several different cell types.

As such, barcoded sequence reads from each library generated using the original barcoded amplified cDNA that share the same barcode will most likely have come from the same cell. Moreover, as further discussed below, other aliquots in the plurality of aliquots can be subjected to other forms of single cell sequence or expression analysis and data derived from such pipelines can be indexed to individual cells in the discrete attribute value dataset based on common barcodes.

Thus, in a joint gene expression/targeted V(D)J experiment, users will create the above-described libraries (e.g., first and second aliquot described above) and run the respective analysis pipeline for each library, such as the pipeline disclosed the section entitled "Discrete attribute value pipeline," in U.S. Patent Application No. 62/572,544, entitled "Systems and Methods for Visualizing a Pattern in a Dataset," filed Oct. 15, 2017, as well as the pipeline disclosed in the present disclosure that forms a clonotype dataset 122 thereby respectively populating the discrete attribute value dataset and the clonotype dataset 122. In other words, once the analysis pipelines have completed, the discrete attribute value (e.g., gene expression) pipeline will yield a discrete attribute value dataset (e.g., a Loupe Cell Browser (cloupe) file, as disclosed in U.S. Provisional Patent Application No. 62/572,544, filed Oct. 15, 2017 entitled "Systems and Methods for Visualizing a Pattern in a Dataset." The targeted VDJ pipeline will yield a clonotype dataset 122 (e.g., Loupe VDJ Browser (vloupe) file, as disclosed herein. The discrete attribute value dataset and the clonotype dataset 122 share common barcodes because they are derived from the same cells in the same biological sample under study, the VDJ browser 120 is able to import the clustered dataset 180 derived from the discrete attribute set into the clonotype dataset 122 workspace of the corresponding clonotype dataset 122. The discrete attribute values 120 of the genes of the discrete attribute value dataset are directly traceable to single corresponding single cells in both the discrete attribute value dataset and the corresponding clonotype dataset 122. This feature advantageously provides an example of integrated single cell genomic analysis, where a worker can combine information about the same cells arising from two or more different data processing pipelines (e.g., the clonotype dataset 122 and the discrete attribute value dataset) in order to provide new, multi-faceted information about those cells. In addition, such embodiments of the VDJ cell browser 120 that can access both the clonotype dataset 122 and the discrete attribute value dataset 120 in which genes have been indexed to a single cell and to a clonotype 124 through common barcodes in the clonotype dataset 122 and the corresponding discrete attribute value dataset, enables the review of the discrete attribute values using clonotype as a filter.

The discrete attribute values in the discrete attribute value dataset are used by a clustering module in the cell browser disclosed in U.S. Patent Application 62/572,544 to cluster the cells into clusters in the form of a clustered dataset 180 (equivalent to clustered dataset 128 in U.S. patent application Ser. No. 15/891,607). As such, the clustered dataset 180 identifies the bar codes 130 that map to each cluster. In embodiments where the same biological sample was used to construct both the clonotype dataset and the discrete attribute set, the cluster information from the clustered dataset derived from the discrete attribute set includes bar codes that map onto the bar codes in the clonotype dataset. Thus, it is possible to use the expression cluster information (e.g., the barcode) of the clustered dataset to identify which cells in the clonotype set belong to which clusters in the clustered dataset.

In typical embodiments, principal component values stored in the discrete attribute value dataset that have been computed by the method of principal component analysis using the discrete attribute values of the genes (first entities) across the plurality of cells (second entities) of the discrete attribute value dataset are used by the clustering module of the cell browser to take the discrete attribute value dataset and cluster the cells into a clustered dataset 180.

Principal component analysis (PCA) is a mathematical procedure that reduces a number of correlated variables into a fewer uncorrelated variables called "principal components." The first principal component is selected such that it accounts for as much of the variability in the data as possible, and each succeeding component accounts for as much of the remaining variability as possible. The purpose of PCA is to discover or to reduce the dimensionality of the dataset, and to identify new meaningful underlying variables. PCA is accomplished by establishing actual data in a covariance matrix or a correlation matrix. The mathematical technique used in PCA is called Eigen analysis: one solves for the eigenvalues and eigenvectors of a square symmetric matrix with sums of squares and cross products. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows (or columns) of this matrix. See, for example, Duda, Hart, and Stork, *Pattern Classification*, Second Edition, John Wiley & Sons, Inc., NY, 2000, pp. 115-116, which is hereby incorporated by reference.

For clustering in accordance with one embodiment of the clustering module of in U.S. Patent Application 62/572,544, consider the case in which each second entity is associated with ten first entities in a discrete attribute value dataset that is to be clustered into a corresponding clustered dataset. In such instances, each second entity can be expressed as a vector:

$$\vec{X}_{10} = \{x_1, x_2, x_3, x_4, x_5, x_6, x_7, x_8, x_9, x_{10}\}$$

where $X_i$ is the discrete attribute value for the first entity i associated with the second entity. Thus, if there are one thousand second entities, 1000 vectors are defined. Those cells that exhibit similar discrete attribute values across the set of genes of the discrete attribute value dataset will tend to cluster together. For instance, in the case where each second entity is an individual cell, the first entities correspond to mRNA mapped to individual genes within such individual cells, and the discrete attribute values are mRNA counts for such mRNA, it is the case in some embodiments that the discrete attribute value dataset includes mRNA data from one or more cell types (e.g., diseased state and non-diseased state), two or more cell types, three or more cell types. In such instances, it is expected that cells of like type will tend to have like values for mRNA across the set of first entities (mRNA) and therefor cluster together. For instance, if the discrete attribute value dataset includes class a: cells from subjects that have a disease, and class b: cells from subjects that do not have a disease, an ideal clustering classifier will cluster the discrete attribute value dataset into two groups, with one cluster group uniquely representing class a and the other cluster group uniquely representing class b.

For clustering in accordance with another embodiment of the clustering module of U.S. Patent Application 62/572,544, consider the case in which each second entity is associated with ten principal component values that collectively represent the variation in the discrete attribute values of a large number of first entities of a given second entity with respect to the discrete attribute values of corresponding first entities of other second entities in the dataset. In such instances, each second entity can be expressed as a vector:

$$\vec{X}_{10} = \{x_1, x_2, x_3, x_4, x_5, x_6, x_7, x_8, x_9, x_{10}\}$$

where $X_i$ is the principal component value i associated with the second entity. Thus, if there are one thousand second entities, one those vectors are defined. Those second entities that exhibit similar discrete attribute values across the set of principal component values will tend to cluster together. For instance, in the case where each second entity is an individual cell, the first entities correspond to mRNA mapped to individual genes within such individual cells, and the discrete attribute values are mRNA counts for such mRNA, it is the case in some embodiments that the discrete attribute value dataset includes mRNA data from one or more cell types (e.g., diseased state and non-diseased state), two or more cell types, three or more cell types. In such instances, it is expected that cells of like type will tend to have like values for mRNA across the set of first entities (mRNA) and therefor cluster together. For instance, if the discrete attribute value dataset includes class a: cells from subjects that have a disease, and class b: cells from subjects that have a disease, an ideal clustering classifier will cluster the discrete attribute value dataset into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, Second edition, John Wiley & Sons, Inc. New York, which is hereby incorporated by reference, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (Third Edition), Wiley, New York, N.Y.; and Backer, 1995, *Computer Assisted Reasoning in Cluster Analysis*, Prentice Hall, Upper Saddle River, N.J. Particular exemplary clustering techniques that can be used by the clustering module of U.S. Patent Application 62/572,544 to cluster a plurality of vectors, where each respective vector in the plurality of vectors comprises the discrete attribute values across the first entities of a corresponding second entity (or principal components derived therefrom) includes, but is not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Thus, in some embodiments, the clustering module of U.S. Patent Application 62/572,544 clusters the discrete attribute value dataset using the discrete attribute value for each first entity (e.g., mRNA of genes) in the plurality of first entities for each respective second entity (e.g., cell) in the plurality of second entities (e.g., plurality of cells), or principal component values derived from the discrete attribute values, thereby assigning each respective second entity in the plurality of second entities to a corresponding cluster in a plurality of clusters and thereby assigning a cluster attribute value to each respective second entity in the plurality of second entities.

In some embodiments, the clustering module of U.S. Patent Application No. 62/572,544 makes use of k-means clustering to form a clustered dataset 180. The goal of k-means clustering is to cluster the discrete attribute value dataset based upon the principal components or the discrete attribute values of individual second entities into K partitions. In some embodiments, K is a number between 2 and 50 inclusive. In some embodiments, the number K is set to a predetermined number such as 10. In some embodiments, the number K is optimized for a particular discrete attribute value dataset. In some embodiments, a user sets the number K using the cell browser 150.

As noted in U.S. Patent Application No. 62/572,544, in some embodiments, the discrete attribute value dataset that is clustered includes discrete attribute values for 1000 or more, 3000 or more, 5000 or more, 10,000 or more, or 15,000 or more mRNAs in each cell represented by the dataset. In some such embodiments, the discrete attribute value dataset includes discrete attribute values for the mRNAs of 500 or more cells, 5000 or more cells, 100,000 or more cells, 250,000 or more cells, 500,000 or more cells, 1,000,000 or more cells, 10 million or more cells or 50 million or more cells. In some embodiments, each single cell is a human cell. In some embodiments, each second entity represents a different human cell. In some embodiments, the discrete attribute value dataset includes data for human cells of several different classes (e.g., representing different deceased states and/or wild type states). In such embodiments, the discrete attribute value for a respective mRNA (first entity) in a given cell (second entity) is the number of mRNAs for the respective mRNA that were measured in the given cell. This will either be zero or some positive integer. In some embodiments, the discrete attribute value for a given first entity for a given second entity is a number in the set $\{0, 1, \ldots, 100\}$. In some embodiments, the discrete attribute value for a given first entity for a given second entity is a number in the set $\{0, 1, \ldots, 50\}$. In some embodiments, the discrete attribute value for a given first entity for a given second entity is a number in the set $\{0, 1, \ldots, 30\}$. In some embodiments, the discrete attribute value for a given first entity for a given second entity is a number in the set $\{0, 1, \ldots, N\}$, where N is a positive integer.

Figure 50A:
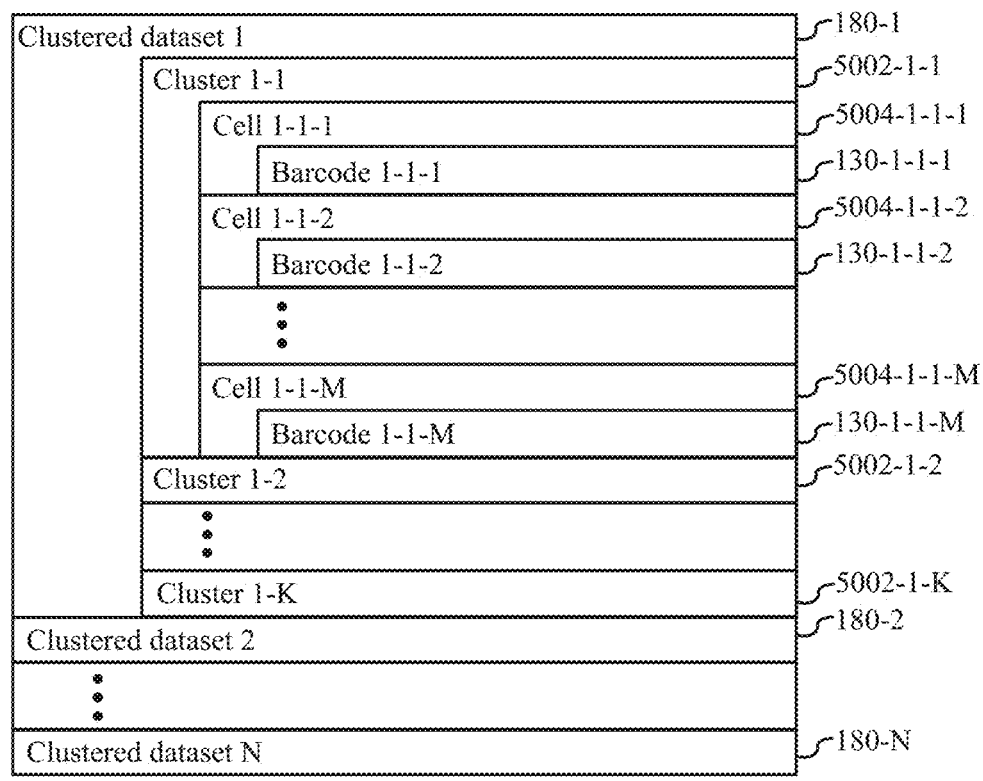
FIG. 50A illustrates the architecture of a clustered dataset in accordance to an embodiment of the present disclosure.

Referring to FIG. 50A, a clustered dataset 180 comprises a plurality of clusters 5002. As discussed above, each cluster 5002 comprises a plurality of cells 5004 that have been clustered together based upon the expression pattern of the mRNA within their cells. Moreover, as discussed above, the barcodes 130 that are uniquely associated with the cells of each cluster can be mapped onto barcodes 130 that support clonotypes 124 in a clonotype dataset 122 when the clonotype dataset 122 is derived from a common sample of barcoded amplified cDNA that was used to form the discrete attribute value dataset that forms the basis of the clustered dataset 180.

Figure 50B:
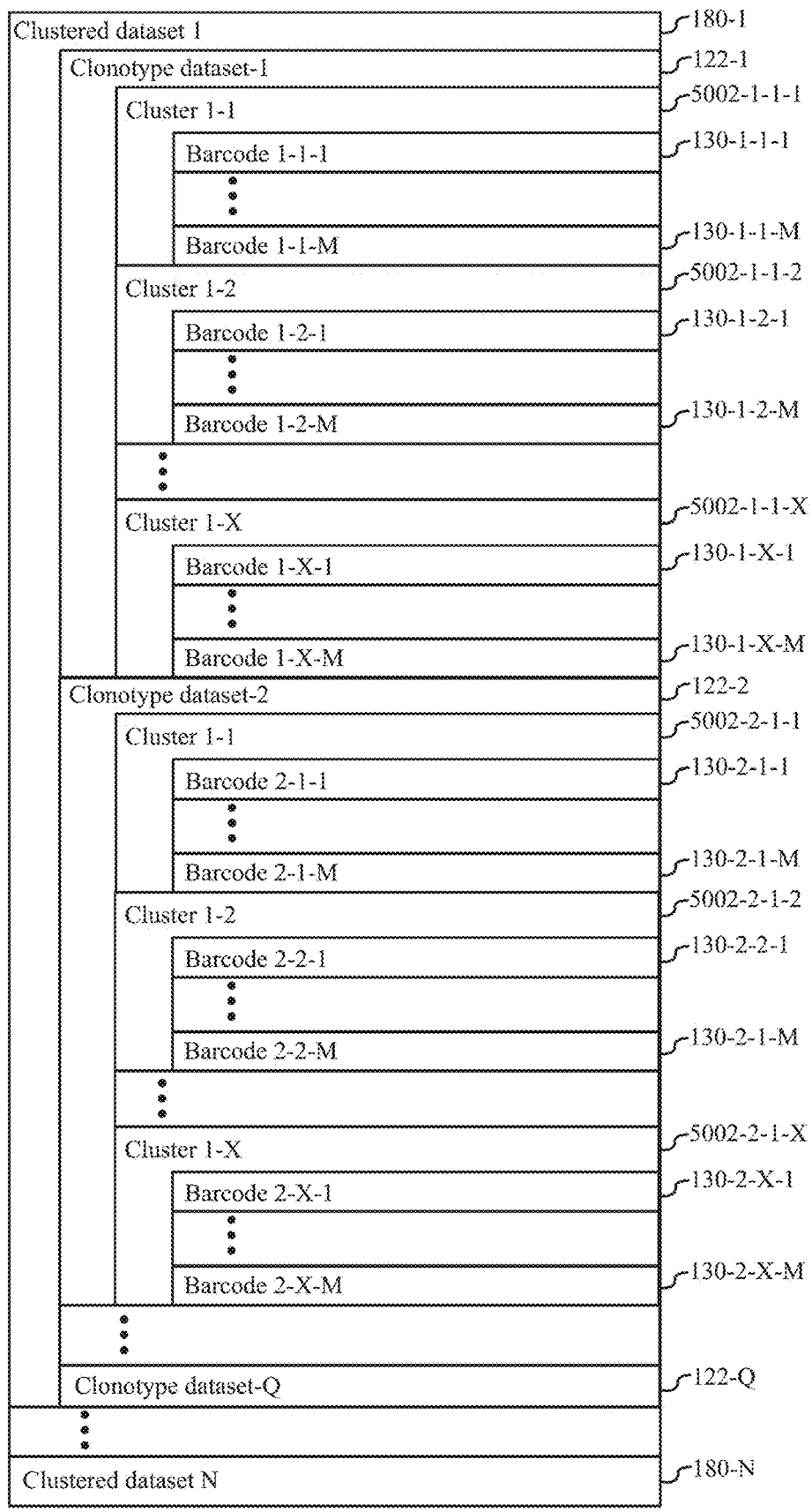
FIG. 50B illustrates the relationship between a clustered dataset and one or more clonotype datasets when such datasets have been built using single cell sequencing methods using a common pool of barcoded cDNA constructs from the same biological sample in accordance to an embodiment of the present disclosure.

In the case where the VDJ cell browser 120 has opened one or more clonotype datasets 122 as well as a clustered dataset 180 that were formed using a common sample of barcoded amplified cDNA, the relation between the gene expression barcodes 130 of the clustered dataset 180 and the barcodes 130 of the clonotype dataset 122 is tracked by the VDJ cell browser 120 using the exemplary data structure disclosed in FIG. 50B. As illustrated in FIG. 50B, for each loaded clustered dataset 180, there are a plurality of clusters 5002. Each such cluster 5002 includes a plurality of second entities. Each such cell is supported by one or more barcodes 130. In some embodiments, a cell is supported by a barcode 130 when the barcode 130 is unique to the cell. As such, there is a list of barcodes that support a given cluster 5002 in the clustered dataset 180. In the data structure illustrated in FIG. 50B, for each respective clustered dataset 180 that is loaded, the entire set of clonotype datasets 122 that have been loaded is represented. In each such clonotype dataset 122 for a given clustered dataset 180, each of the clusters 5002 of the clustered dataset 180 is represented. In each such represented cluster 5002, those bar codes 130 that are common to both the cluster 5002 of the corresponding clustered dataset 180 and that are also found in the respective clonotype dataset 122 are listed. In this way, it is possible to identify which cells in a given clonotype dataset 122 are also in which clusters 5002 in the clustered dataset 180.

Thus, referring to FIG. 40, one or more clustered datasets of the type described in U.S. Patent Application No. 62/572, 544 can be loaded into the VDJ cell browser 120 by clicking the open menu 4002, and selecting "Load clusters from cloupe file." Upon selection of this option, panel 4102 of FIG. 41 appears with a listing of available clustered datasets 180. Upon user selection of the clustered dataset "CRC_aggr2.cloupe" file from panel 4102, the clustered dataset 180 is loaded into the VDJ cell browser 120. After loading one or more clustered datasets 180, the user is able to apply the clusters 5002 within the clustered dataset 180 in a number of different ways when the clustered dataset 180 and the one or more opened clonotype datasets 122 are formed from aliquots of the same barcoded amplified cDNA from a biological sample and thus have barcodes that are common to each other.

Figure 42:
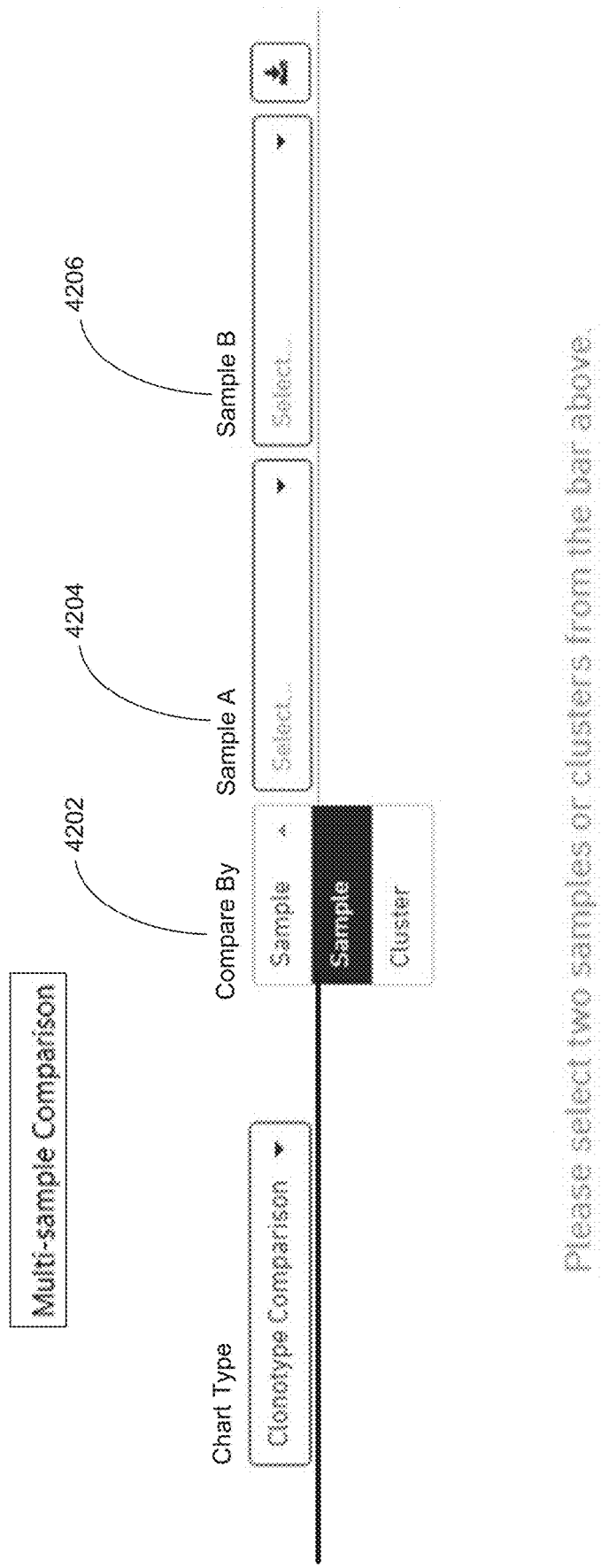
FIG. 42 illustrates obtaining information for a clonotype comparison view for comparing clonotype distributions between gene-expression clusters in accordance with some embodiments.
Figure 43:
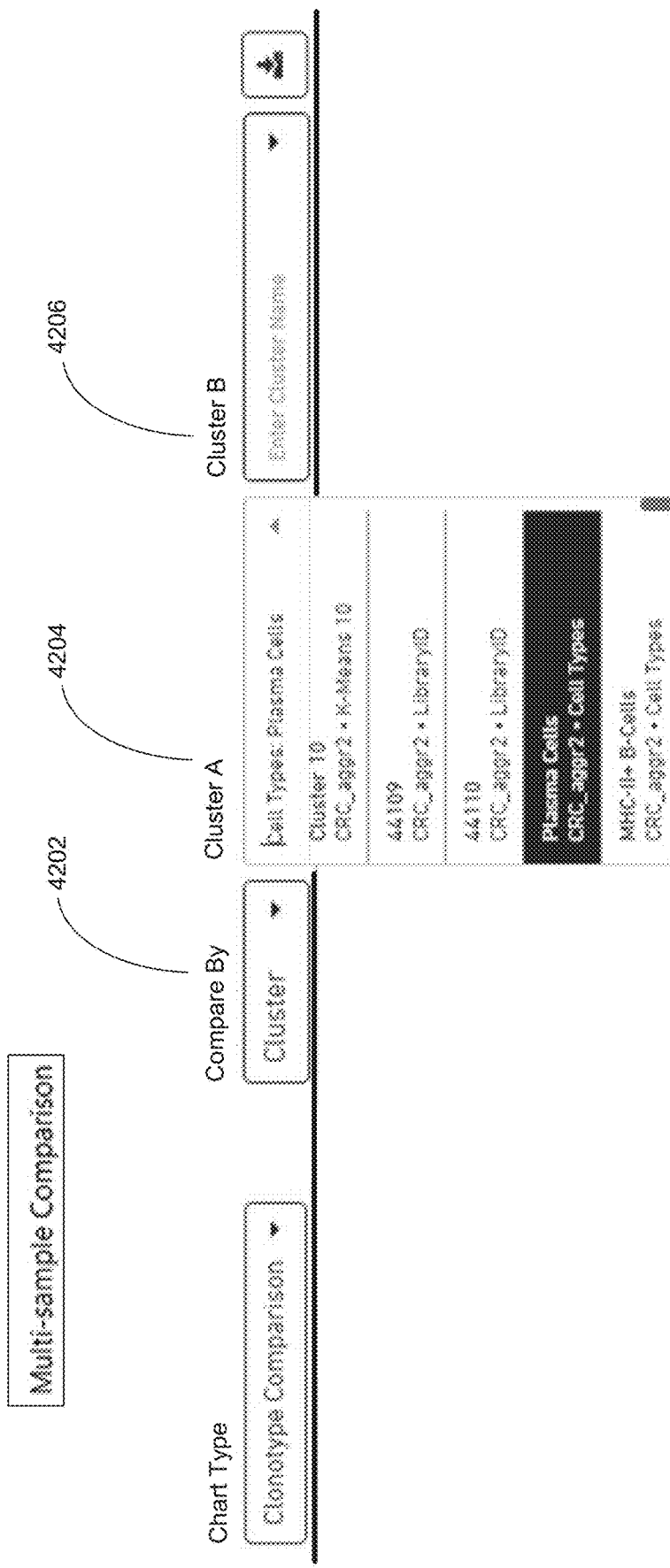
FIG. 43 illustrates selecting gene expression clusters for a clonotype comparison view for comparing clonotype distributions between gene expression clusters in accordance with some embodiments.
Figure 44:
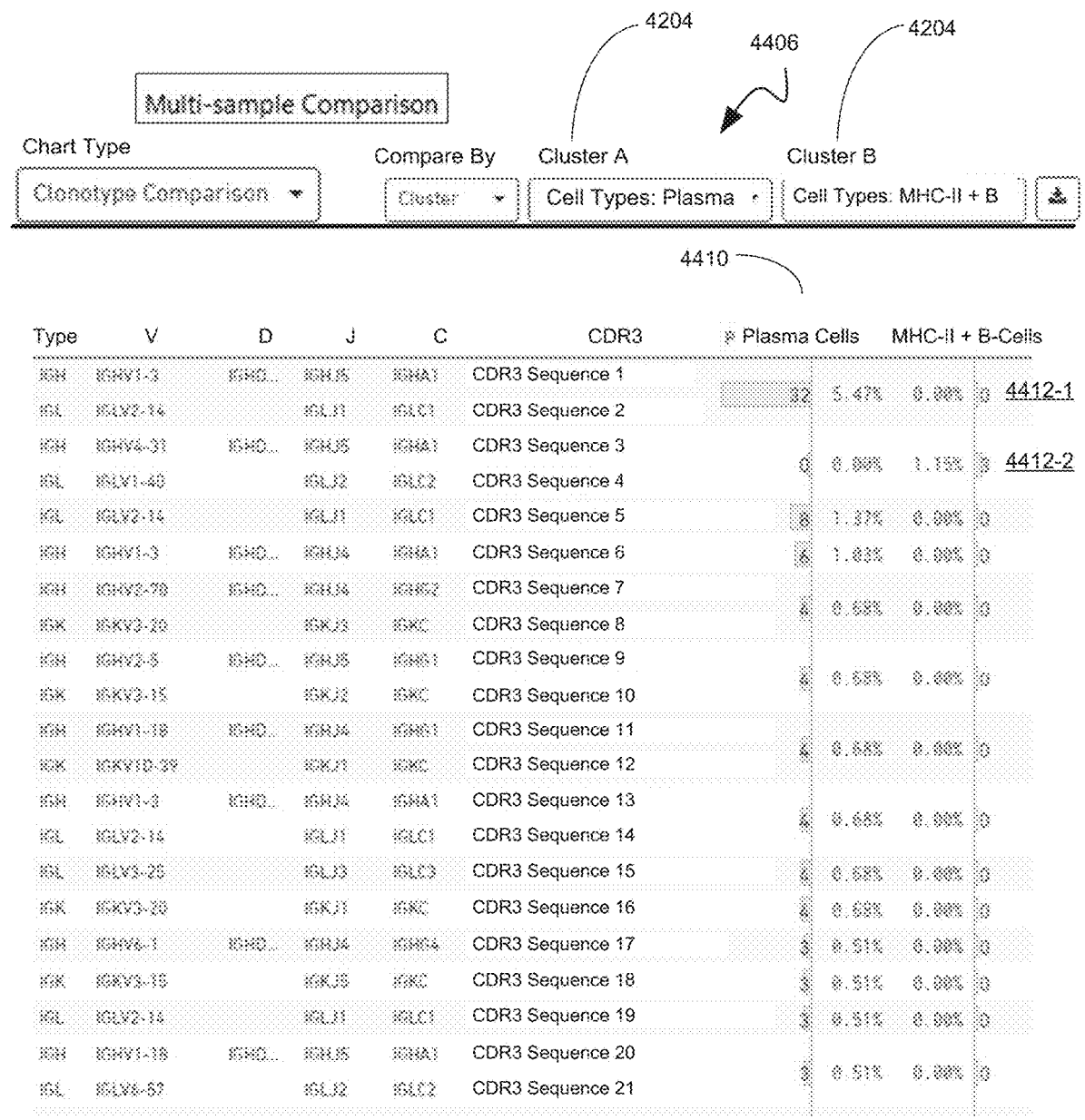
FIG. 44 illustrates the clonotype comparison between the cells in the gene expression clusters selected in FIG. 43 within the CRC_aggr2 clustered dataset spanning the four clonotype datasets of FIG. 25 in accordance with some embodiments.

For instance, referring to FIG. 42, the VDJ cell browser 120 can be used to compare clonotype distributions between gene-expression clusters 5002. To do this, affordance 4202 offered by the VDJ cell browser 120 is switched from 'Sample' to 'Cluster.' The user then selects two clusters 5002 that are present in a loaded clustered dataset 180 using the Cluster A 4204 and Cluster B 4206 affordances as further illustrated in FIG. 43 where the "Plasma Cells" cluster from the CRC_aggr2 clustered dataset is selected using affordance 4204 Cluster A (FIG. 43). Upon further selecting the "MHC-II+B-Cells" cluster 5002 from the CRC_aggr2 clustered dataset 180 using affordance 4206 of FIG. 43, a table 4406 of top clonotype criteria for the two selected clonotype datasets 122 (FIG. 44) is provided that is similar to table 3904 of FIG. 39 with the exception that the data is filtered so that only the data of those cells in the two clonotype datasets 122 that are also in the two selected clusters 5002 of the loaded clustered dataset 180 are compared in the table. Each set of lines in table 4406 represents a clonotype 124 that is present in at least one of the two clonotype datasets 122 being compared from cells that are in either of the two clusters 5002 selected by affordances 4204 and 4204. For each clonotype 124 listed in table 4206, a designation of the chain type, V gene, D gene, J gene, and C gene, and the amino acid sequence of the CDR3 region of the clonotype 124 is provided. Furthermore, the number of cells having this respective clonotype 124 across the combination of the two selected clonotype datasets 122 is provided in column 4210. For instance, for the clonotype represented by the set of lines 4412-1 in table 4410, there are collectively 32 cells across the two clonotype datasets 122 being compared that are also in the "plasma cells" cluster of the loaded clustered dataset, and there are collectively no cells across the two clonotype datasets 122 being compared that are also in the "MHC-II+B-Cells" cluster 5002 of the loaded clustered dataset 180. For the clonotype 124 represented by the set of lines 4412-2 in table 4410, there are collectively no cells across the two clonotype datasets 122 being compared that are also in the "plasma cells" cluster 5002 of the loaded clustered dataset 180, and there are collectively three cells across the two clonotype datasets 122 being compared that are also in the "MHC-II+B-Cells" cluster 5002 of the loaded clustered dataset 180. Each such clonotype table 4410 also provides a designation of what percent of the cells in each of the selected clonotype datasets 122 are represented. In the embodiment illustrated in FIG. 44, the clonotypes 124 are ordered by p-value (between the two clusters 5002 being compared) as computed by Fisher's exact test, and the list is filtered to cases where there are at least three cells of a particular clonotype in one of the clusters. The comparison of FIG. 44 is made possible by the fact that the disclosed clonotype datasets 122 and the applied clustered dataset 180 are built using single cell sequencing methods using a common pool of barcoded cDNA constructs from the same biological sample and thus the clonotype datasets 122 and the clustered datasets individually track the cells in the biological samples used to construct such datasets as disclosed above and it is possible to map cells from a clonotype dataset onto cells in the clustered dataset 180.

Additionally, once a clustered dataset 180 has been loaded, the clusters 5002 can be applied to the single clonotype dataset 122 analyses to thereby filter the view of clonotypes 124 in the single clonotype dataset 122 to those clonotypes 124 from cells that are in a particular cluster 5002 in the clustered dataset 180. For instance, referring to FIG. 45, only clonotype data from the "44914-CRC_1_UB" clonotype dataset 122 is shown. Moreover, affordance 4502 is used to limit the list of clonotypes 124 displayed in the right-hand table to those from cells in the "44914-CRC_1_UB" clonotype dataset 122 that are also in the "Plasma Cells" cluster 5002 from the "CRC_aggr2" clustered dataset 180.

Figure 45:
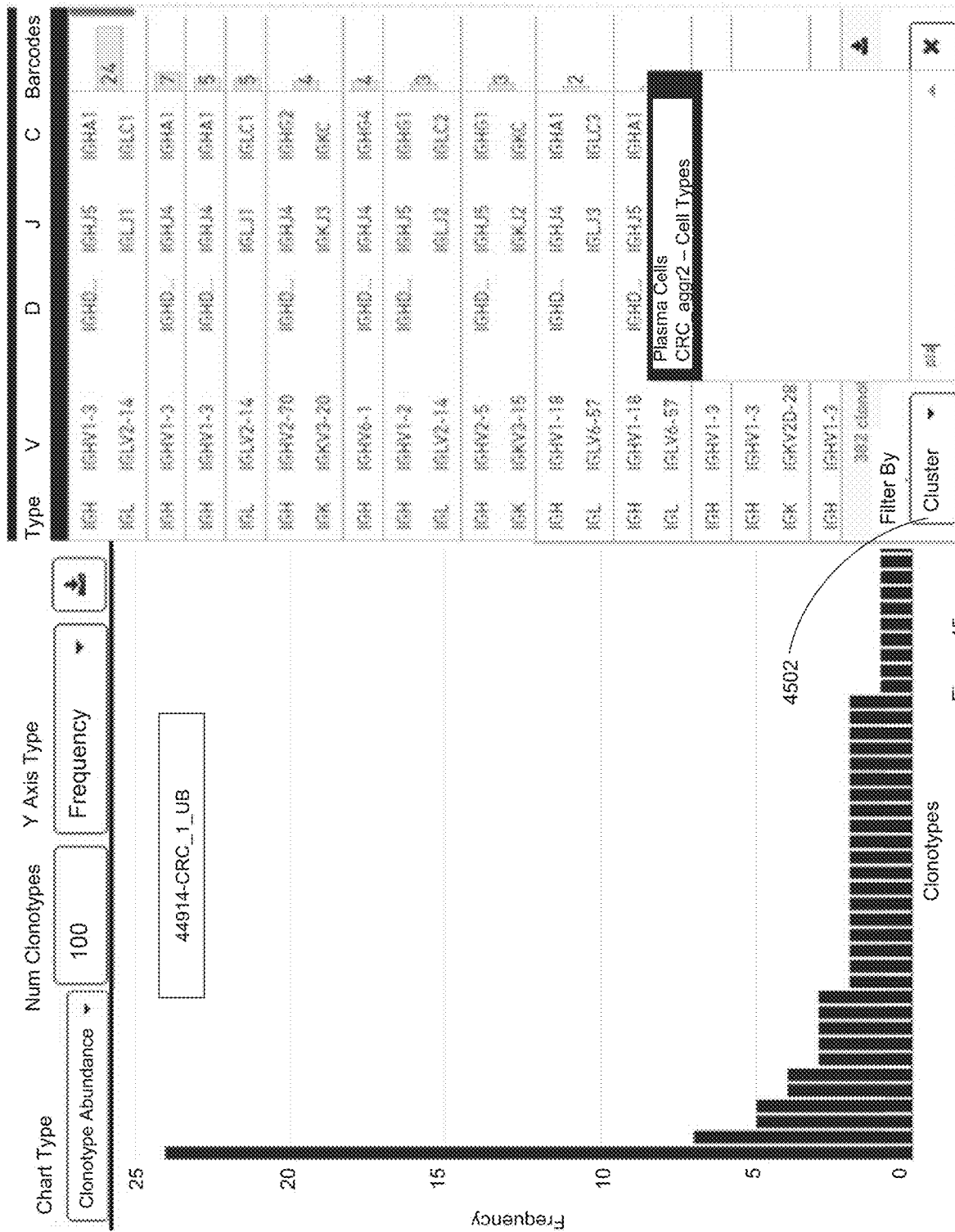
FIG. 45 illustrates, for the single clonotype dataset "44914-CRC_1_UB," filtering the clonotype list by a gene expression cluster from the CRC_aggr2 clustered dataset in accordance with some embodiments.
Figure 46:
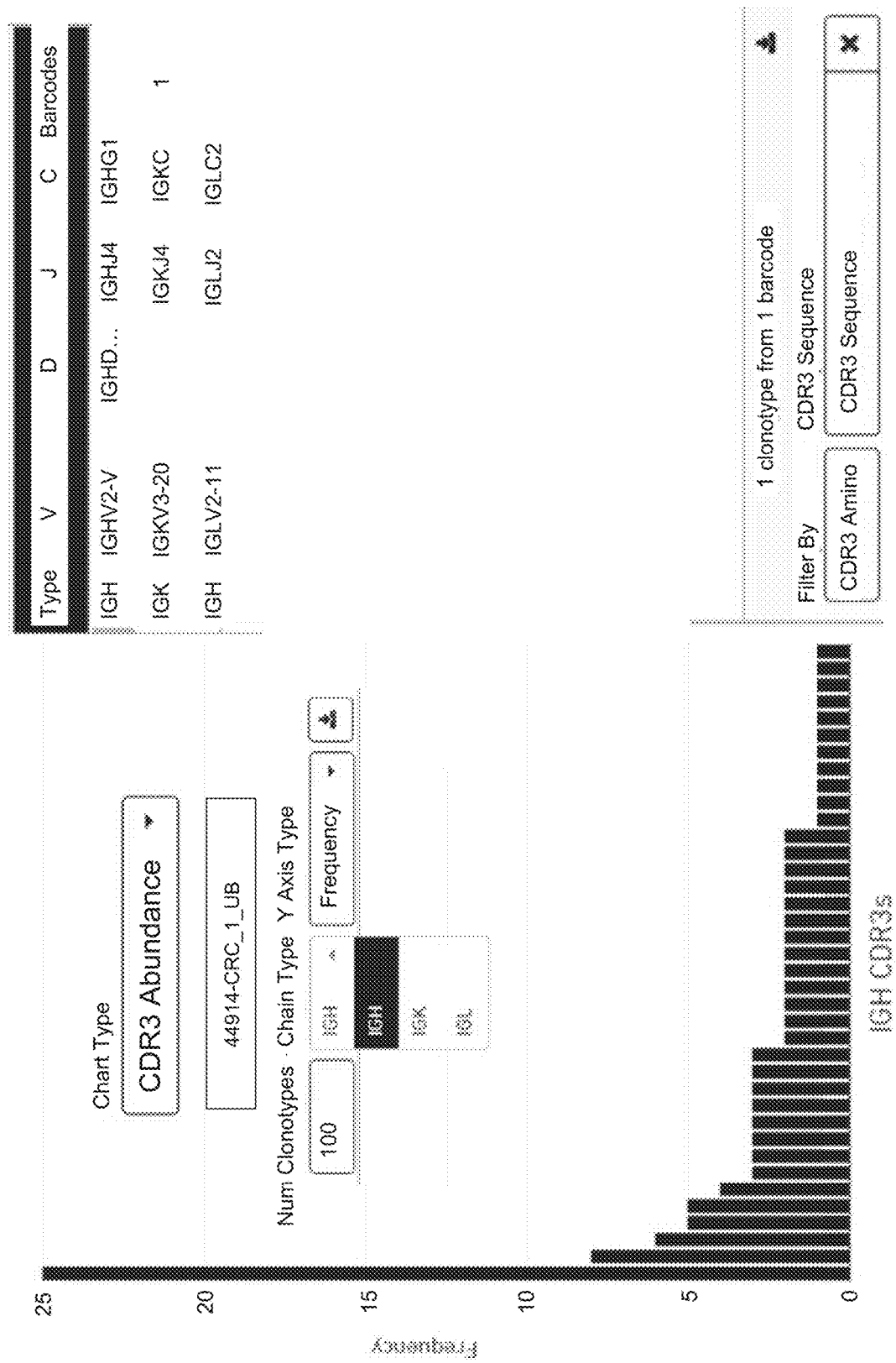
FIG. 46 illustrates a single-chain CDR3 abundance chart with chain type filter within a single selected clonotype dataset in accordance with some embodiments.

The comparison of FIG. 45 is made possible by the fact that the disclosed clonotype datasets 122 and the applied clustered dataset 180 are built using single cell sequencing methods using a common pool of barcoded cDNA constructs from the same biological sample and thus the clonotype datasets 122 and the clustered datasets individually track the cells in the biological samples used to construct such datasets as disclosed above and it is possible to map cells from a clonotype dataset onto cells in the clustered dataset 180.

Single-Sample Charts.

Figure 47:
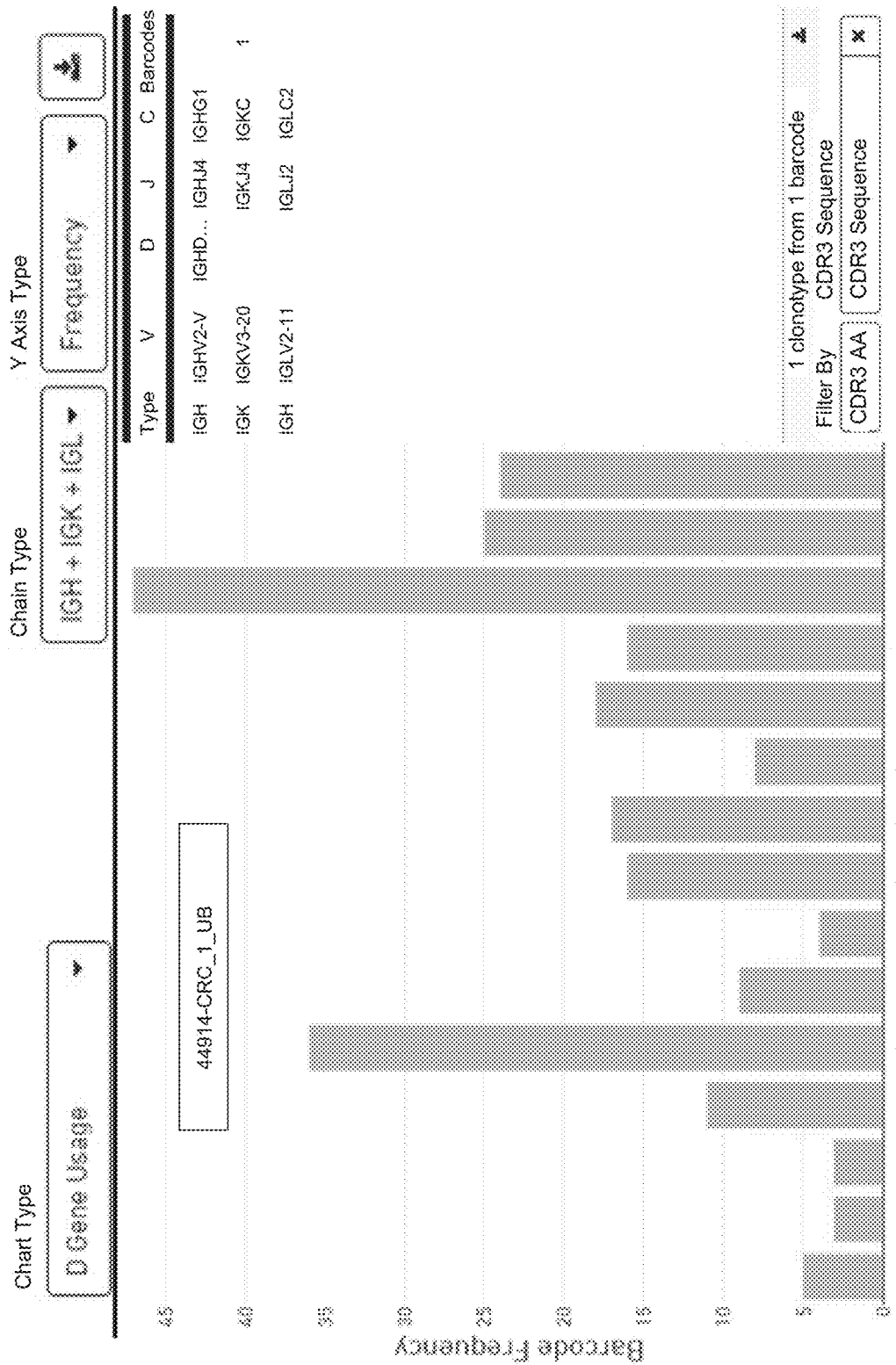
FIG. 47 illustrates a D gene usage chart within a single selected clonotype dataset in accordance with some embodiments.
Figure 48:
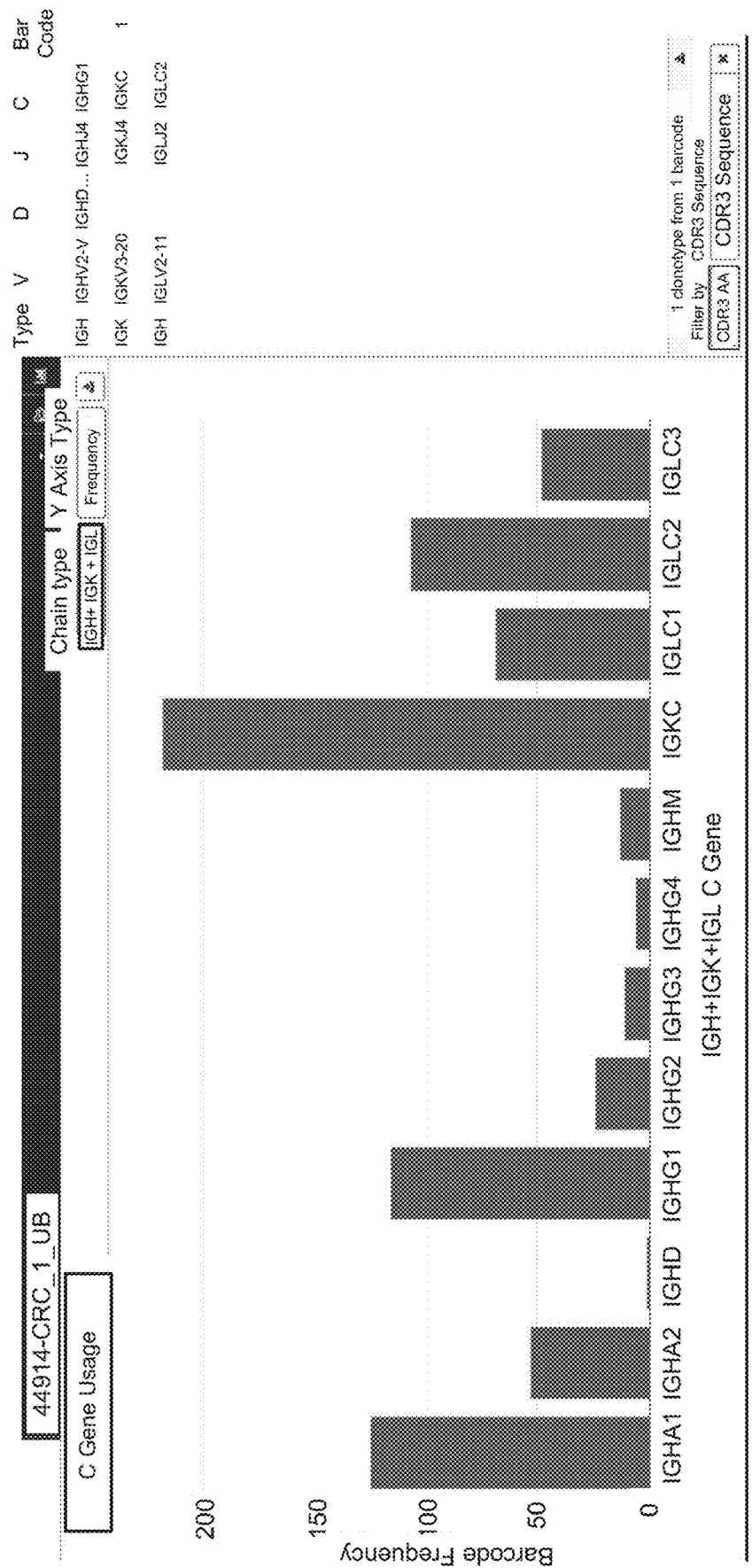
FIG. 48 illustrates a C gene usage chart within a single selected clonotype dataset in accordance with some embodiments.
Figure 49:
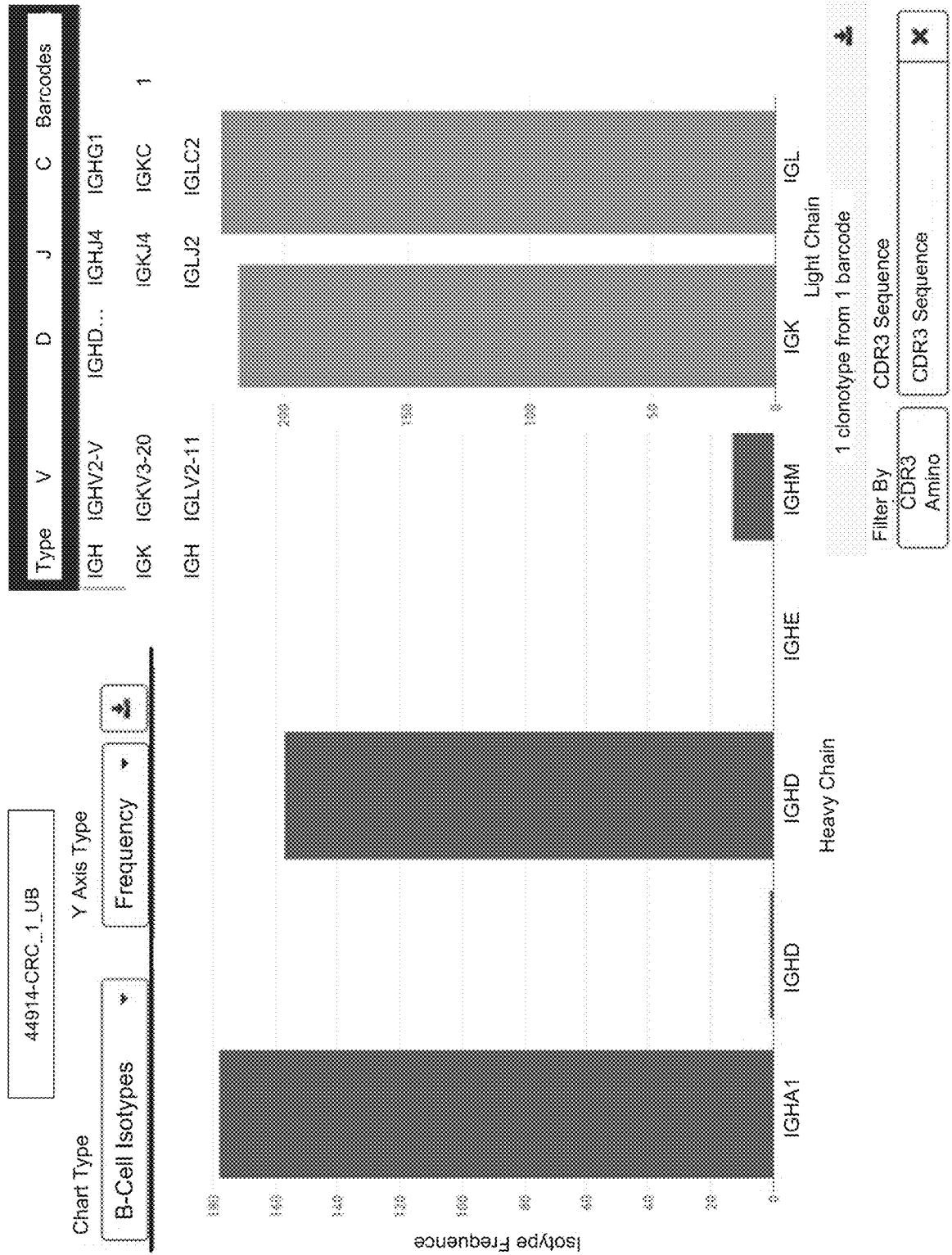
FIG. 49 illustrates B-cell isotype views within a single selected clonotype dataset in accordance with some embodiments.

Referring to FIGS. 47 through 49, VDJ browser 120 provides various single clonotype dataset charts to analyze single clonotype datasets 122 in accordance with some embodiments of the present disclosure. For instance, FIG. 47 illustrates a D gene usage chart within a single selected clonotype dataset 122 in accordance with some embodiments. FIG. 48 illustrates a C gene usage chart within a single selected clonotype dataset 122 in accordance with some embodiments. FIG. 49 illustrates B-cell isotype views within a single selected clonotype dataset 122 in accordance with some embodiments.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A method of screening a plurality of clonotypes, the method comprising:
    at a computer system having one or more processors, and memory storing one or more programs for execution by the one or more processors:
        obtaining, in electronic form, a clonotype dataset formed using a first plurality of sequence reads of nucleic acids in a first aliquot of nucleic acids pooled from a plurality of 100 or more cells from a biological sample of a single subject comprising B cells or T cells, wherein
            each respective sequence read in the first plurality of sequence reads includes a corresponding barcode, from a plurality of barcodes, that indicates which cell in the plurality of cells originated the nucleic acid represented by the respective sequence read,
            the clonotype dataset comprises, for each respective cell in the plurality of cells, a corresponding contig entry in a plurality of contig entries, wherein the plurality of contig entries represents the plurality of clonotypes, and wherein the plurality of clonotypes comprises 25 clonotypes,
            each respective clonotype in the plurality of clonotypes corresponds to one or more contig entries in the clonotype dataset, and
            for each respective cell in the plurality of cells, a corresponding contig entry in the plurality of contig entries:
                (i) corresponds to a T-cell receptor or B-cell receptor from the respective cell in the plurality of cells and (ii) comprises an indication of chain type for the corresponding T-cell receptor or B-cell receptor, a corresponding contig sequence, and a corresponding barcode, from the plurality of barcodes, that identifies the respective cell for the respective contig entry,
                wherein the corresponding contig sequence determined by a subset of sequence reads in the first plurality of sequence reads (i) having the respective barcode for the respective cell and (ii) encoding all or a portion of the corresponding T-cell receptor chain or B-cell receptor chain from the respective cell;
        obtaining, in electronic form, a discrete attribute value dataset formed using a second plurality of sequence reads of nucleic acids in a second aliquot of nucleic acids pooled from the plurality of cells, wherein each respective sequence read in the second plurality of sequence reads includes a corresponding barcode, from the plurality of barcodes, that indicates which cell in the plurality of cells originated the nucleic acid represented by the respective sequence read, and the discrete attribute value data set comprises:
            for each respective cell in the plurality of cells,
                for each respective gene in a plurality of genes, a corresponding discrete attribute value for a count of a number of mRNA mapping to the respective gene in the respective cell determined from a number of sequence reads in the second plurality of sequence reads that map to the respective gene and have the barcode for the respective cell;
        clustering the plurality of cells into a plurality of clusters by (i) computing a plurality of distances using each discrete attribute value of each cell in the plurality of cells for each unique pair of cells in the plurality of cells and (ii) evaluating the plurality of distances with a criterion function, wherein
            the plurality of distances includes a separate distance for each pair of cells in the plurality of cells,
            each respective distance in the plurality of distances represents a different pair of cells in the plurality of cells and quantifies a distance between a respective first vector formed by the discrete attribute values for a respective first cell in the different pair of cells and a respective second vector formed by the discrete attribute values for a respective second cell in the different pair of cells, and
            each respective cluster in the plurality of clusters represents a corresponding subset of cells of the plurality of cells that are clustered together based on evaluation of distances in the plurality of distances representing different pairs of cells within the corresponding subset of cells with the criterion function;
        matching, for each respective cell in a first cluster in the plurality of clusters, the corresponding barcode of the respective cell with a corresponding barcode for a respective contig entry in the plurality of contig entries, thereby obtaining a corresponding contig entry for the respective cell; and
        providing, for each respective clonotype in the plurality of clonotypes represented in the first cluster, a number of cells in the plurality of cells in the clonotype dataset, that represent the respective clonotype that are in the first cluster, based on the corresponding contig entry of each respective cell in the first cluster.

2. The method of claim 1, further comprising ordering respective clonotypes in the first cluster by the number of the plurality of cells that have the respective clonotype in the first cluster.

3. The method of claim 1, wherein more than one cell in the plurality of cells have the same clonotype in the plurality of clonotypes.

4. The method of claim 1, wherein more than ten cells in the plurality of cells have the same clonotype in the plurality of clonotypes.

5. The method of claim 1, wherein the plurality of clonotypes comprises 100 clonotypes.

6. The method of claim 1, wherein the plurality of cells consists of B-cells from the single subject.

7. The method of claim 1, wherein the plurality of cells consists of T-cells from the single subject.

8. The method of claim 1, wherein the single subject is mammalian.

9. The method of claim 1, wherein the single subject is a reptile, avian, amphibian, fish, ungulate, ruminant, bovine, equine, caprine, ovine, swine, camelid, monkey, ape, ursid, poultry, dog, cat, mouse, rat, fish, dolphin, whale or shark.

10. The method of claim 1, wherein the clonotype dataset comprises a file that includes a series of data blocks with a master JSON table of contents at the beginning of the file and a JSON table of contents describing the addresses and structure of each block at the end of the file.

11. The method of claim 10, wherein
a block in the series of data blocks consists of a database,
the database comprises a first table for the plurality of clonotypes, a second table for the plurality of contig entries in the clonotype dataset, and a secondary table that maps a respective barcode in the plurality of barcodes to a respective clonotype in the plurality of clonotypes, and
the database is queried to create a clonotype list, sorted by frequency, for the matching step.

12. The method of claim 1, wherein the plurality of cells comprises 1000 or more cells.

13. A computer system for screening a plurality of clonotypes, the computer system comprising:
one or more processors; and
memory addressable by the one or more processors, the memory storing at least one program for execution by the one or more processors, the at least one program comprising instructions for:
obtaining, in electronic form, a clonotype dataset formed using a first plurality of sequence reads of nucleic acids in a first aliquot of nucleic acids pooled from a plurality of 100 or more cells from a biological sample of a single subject comprising B cells or T cells, wherein
each respective sequence read in the first plurality of sequence reads includes a corresponding barcode, from a plurality of barcodes, that indicates which cell in the plurality of cells originated the nucleic acid represented by the respective sequence read,
the clonotype dataset comprises, for each respective cell in the plurality of cells, a corresponding contig entry in a plurality of contig entries, wherein the plurality of contig entries represents the plurality of clonotypes, and wherein the plurality of clonotypes comprises 25 clonotypes,
each respective clonotype in the plurality of clonotypes corresponds to one or more contig entries in the clonotype dataset, and
for each respective cell in the plurality of cells, a corresponding contig entry in the plurality of contig entries:
(i) corresponds to a T-cell receptor or B-cell receptor from the respective individual cell in the plurality of cells and iii) comprises an indication of chain type for the corresponding T-cell receptor or B-cell receptor, a corresponding contig sequence, and a corresponding barcode, from the plurality of barcodes, that identifies the respective cell for the respective contig entry,
wherein the corresponding contig sequence is determined by a subset of sequence reads in the first plurality of sequence reads (i) having the respective barcode for the respective cell and (ii) encoding all or a portion of the corresponding T-cell receptor chain or B-cell receptor chain from the respective cell;
obtaining, in electronic form, a discrete attribute value dataset formed using a second plurality of sequence reads of nucleic acids in a second aliquot of nucleic acids pooled from the plurality of cells, wherein each respective sequence read in the second plurality of sequence reads includes a corresponding barcode, from the plurality of barcodes, that indicates which cell in the plurality of cells originated the nucleic acid represented by the respective sequence read, and the discrete attribute value data set comprises:
for each respective cell in the plurality of cells,
for each respective gene in a plurality of genes, a corresponding discrete attribute value for a count of a number of mRNA mapping to the respective gene in the respective cell determined from a number of sequence reads in the second plurality of sequence reads that map to the respective gene and have the barcode for the respective cell;
clustering the plurality of cells into a plurality of clusters by (i) computing a plurality of distances using each discrete attribute value of each cell in the plurality of cells for each unique pair of cells in the plurality of cells and (ii) evaluating the plurality of distances with a criterion function, wherein
the plurality of distances includes a separate distance for each pair of cells in the plurality of cells,
each respective distance in the plurality of distances represents a different pair of cells in the plurality of cells and quantifies a distance between a respective first vector formed by the discrete attribute values for a respective first cell in the different pair of cells and a respective second vector formed by the discrete attribute values for a respective second cell in the different pair of cells, and
each respective cluster in the plurality of clusters represents a corresponding subset of cells of the plurality of cells that are clustered together based on evaluation of distances in the plurality of distances representing different pairs of cells within the corresponding subset of cells with the criterion function;
matching, for each respective cell in a first cluster in the plurality of clusters, the corresponding barcode of the respective cell with a corresponding barcode for a respective contig entry in the plurality of contig entries, thereby obtaining a corresponding contig entry for the respective cell; and providing, for each respective clonotype in the plurality of clonotypes represented in the first cluster, a number of cells in the plurality of cells in the clonotype dataset, that represent the respective clonotype that are in the first cluster, based on the corresponding contig entry of each respective cell in the first cluster.

14. A non-transitory computer readable storage medium, wherein the non-transitory computer readable storage medium stores instructions, which when executed by a computer system, cause the computer system to perform a method for screening a plurality of clonotypes, the method comprising:

obtaining, in electronic form, a clonotype dataset formed using a first plurality of sequence reads of nucleic acids in a first aliquot of nucleic acids pooled from plurality of 100 or more cells from a biological sample of a single subject comprising B cells or T cells, wherein each respective sequence read in the first plurality of sequence reads includes a corresponding barcode, from a plurality of barcodes, that indicates which cell in the plurality of cells originated the nucleic acid represented by the respective sequence read, the clonotype dataset comprises, for each respective cell in the plurality of cells, a corresponding contig entry in a plurality of contig entries, wherein the plurality of contig entries represents the plurality of clonotypes, and wherein the plurality of clonotypes comprises 25 clonotypes, each respective clonotype in the plurality of clonotypes corresponds to one or more contig entries in the clonotype dataset, and for each respective cell in the plurality of cells, a corresponding contig entry in the plurality of contig entries:

(i) corresponds to a T-cell receptor or B-cell receptor from the respective cell in the plurality of cells and (ii) comprises an indication of chain type for the corresponding T-cell receptor or B-cell receptor, a corresponding contig sequence, and a corresponding barcode, from the plurality of barcodes, that identifies the respective cell, wherein the corresponding contig sequence is determined by a subset of sequence reads in the first plurality of sequence reads (i) having the respective barcode for the respective cell and (ii) encoding all or a portion of the corresponding T-cell receptor chain or B-cell receptor chain from the respective cell;

obtaining, in electronic form, a discrete attribute value dataset formed using a second plurality of sequence reads of nucleic acids in a second aliquot of nucleic acids pooled from the plurality of cells, wherein each respective sequence read in the second plurality of sequence reads includes a corresponding barcode, from the plurality of barcodes, that indicates which cell in the plurality of cells originated the nucleic acid represented by the respective sequence read, and the discrete attribute value data set comprises:

for each respective cell in the plurality of cells, for each respective gene in a plurality of genes, a corresponding discrete attribute value for a count of a number of mRNA mapping to the respective gene in the respective cell determined from a number of sequence reads in the second plurality of sequence reads that map to the respective gene and have the barcode for the respective cell;

clustering the plurality of cells into a plurality of clusters by (i) computing a plurality of distances using each discrete attribute value of each cell in the plurality of cells for each unique pair of cells in the plurality of cells and (ii) evaluating the plurality of distances with a criterion function, wherein the plurality of distances includes a separate distance for each pair of cells in the plurality of cells, each respective distance in the plurality of distances represents a different pair of cells in the plurality of cells and quantifies a distance between a respective first vector formed by the discrete attribute values for a respective first cell in the different pair of cells and a respective second vector formed by the discrete attribute values for a respective second cell in the different pair of cells, and each respective cluster in the plurality of clusters represents a corresponding subset of cells of the plurality of cells that are clustered together based on evaluation of distances in the plurality of distances representing different pairs of cells within the corresponding subset of cells with the criterion function;

matching, for each respective cell in a first cluster in the plurality of clusters, the corresponding barcode of the respective cell with a corresponding barcode for a respective contig entry in the plurality of contig entries, thereby obtaining a corresponding contig entry for the respective cell; and providing, for each respective clonotype in the plurality of clonotypes represented in the first cluster, a number of cells in the plurality of cells in the clonotype dataset that represent the respective clonotype that are in the first cluster, based on the corresponding contig entry of each respective cell in the first cluster.

\* \* \* \* \*